US012133855B2

(12) United States Patent
Xu et al.

(10) Patent No.: US 12,133,855 B2
(45) Date of Patent: Nov. 5, 2024

(54) LIPID-LIKE NANOCOMPLEXES AND USES THEREOF

(71) Applicant: Trustees of Tufts College, Medford, MA (US)

(72) Inventors: Qiaobing Xu, Lexington, MA (US); Yamin Li, Somerville, MA (US)

(73) Assignee: Trustees of Tufts College, Medford, MA (US)

( * ) Notice: Subject to any disclaimer, the term of this patent is extended or adjusted under 35 U.S.C. 154(b) by 623 days.

(21) Appl. No.: 16/966,368

(22) PCT Filed: Feb. 1, 2019

(86) PCT No.: PCT/US2019/016362
§ 371 (c)(1),
(2) Date: Jul. 30, 2020

(87) PCT Pub. No.: WO2019/152848
PCT Pub. Date: Aug. 8, 2019

(65) Prior Publication Data
US 2020/0368254 A1   Nov. 26, 2020

Related U.S. Application Data

(60) Provisional application No. 62/625,153, filed on Feb. 1, 2018.

(51) Int. Cl.
| | | |
|---|---|---|
| A61K 33/04 | (2006.01) | |
| A61K 9/16 | (2006.01) | |
| A61K 31/22 | (2006.01) | |
| A61K 31/575 | (2006.01) | |
| A61K 47/54 | (2017.01) | |
| C07C 391/00 | (2006.01) | |
| A61K 47/69 | (2017.01) | |
| A61K 48/00 | (2006.01) | |

(52) U.S. Cl.
CPC .......... *A61K 31/575* (2013.01); *A61K 9/1658* (2013.01); *A61K 31/22* (2013.01)

(58) Field of Classification Search
None
See application file for complete search history.

(56) References Cited

U.S. PATENT DOCUMENTS

| | | | | |
|---|---|---|---|---|
| 4,275,236 A | | 6/1981 | Earl et al. | |
| 5,994,317 A | * | 11/1999 | Wheeler | C12N 15/88 424/420 |
| 7,381,416 B2 | * | 6/2008 | Erdelmeir | A61K 31/095 514/23 |
| 8,541,628 B2 | * | 9/2013 | Wheeler | C07K 5/081 568/583 |
| 9,765,022 B2 | * | 9/2017 | Xu | A61K 31/7088 |
| 10,792,328 B2 | * | 10/2020 | Xu | A61K 38/168 |
| 2014/0179854 A1 | | 6/2014 | Liang et al. | |
| 2016/0009643 A1 | * | 1/2016 | Xu | A61K 31/7088 424/490 |
| 2016/0129120 A1 | | 5/2016 | Xu et al. | |
| 2019/0270822 A1 | | 9/2019 | Ayres et al. | |
| 2023/0405022 A1 | | 12/2023 | Xu et al. | |

FOREIGN PATENT DOCUMENTS

| | | |
|---|---|---|
| CN | 103131227 A | 6/2013 |
| DE | 682393 C | 10/1939 |
| JP | 2003-012621 A | 1/2003 |
| WO | WO-2014/186366 A1 | 11/2014 |
| WO | WO-2014/210356 A1 | 12/2014 |
| WO | WO-2016/009643 A1 | 1/2016 |
| WO | WO-2017/176974 A1 | 10/2017 |
| WO | WO-2017/212006 A1 | 12/2017 |
| WO | WO-2019/152848 A1 | 8/2019 |

OTHER PUBLICATIONS

Xu, Huaping, Wei Cao, and Xi Zhang. "Selenium-containing polymers: promising biomaterials for controlled release and enzyme mimics." Accounts of chemical research 46.7 (2013): 1647-1658. (Year: 2013).*
Tong, Rong, et al. "Smart chemistry in polymeric nanomedicine." Chemical Society Reviews 43.20 (2014): 6982-7012. (Year: 2014).*
International Search Report and Written Opinion for International Application No. PCT/US2019/016362 mailed Jun. 7, 2019.
PubChem CID 58329052; Create date Aug. 19, 2012 (7 pages).
PubChem CID 91567364; Create date Mar. 17, 2015 (8 pages).
Extended European Search Report for International Application No. EP 19747806 mailed Jan. 27, 2022.
Partial Supplementary European Search Report for EP Application No. 19747806.8 dated Oct. 15, 2021.
Wang et al., "Combinatorially Designed Lipid-like Nanoparticles for Intracellular Delivery of Cytotoxic Protein for Cancer Therapy," Angewandte Chemie, 126: 2937-2942 (2014).

* cited by examiner

*Primary Examiner* — Bethany P Barham
*Assistant Examiner* — Peter Anthopolos
(74) *Attorney, Agent, or Firm* — Foley Hoag LLP; Dana M. Gordon; Alexander J. Chatterley

(57) ABSTRACT

Disclosed are compounds of formula (I) below:

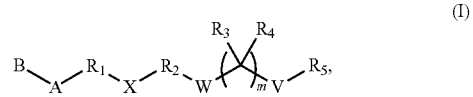

wherein each of the variables A, B, X, W, V, $R_1$-$R_5$, and m is defined herein. Also disclosed are pharmaceutical compositions containing a nanocomplex, wherein the nanocomplex is formed of one of the compounds, and a protein, a nucleic acid, or a small molecule; and methods of treating a medical condition with one of the pharmaceutical compositions.

16 Claims, 28 Drawing Sheets

LIPID-LIKE NANOCOMPLEXES AND USES THEREOF

CROSS-REFERENCE TO RELATED APPLICATION

This application is a U.S. National Stage Application of International Application No. PCT/US2019/016362, filed Feb. 1, 2019; which claims the benefit of priority to U.S. Provisional Patent Application Ser. No. 62/625,153, filed Feb. 1, 2018.

GOVERNMENT SUPPORT

This invention was made with government support under grant 1452122 awarded by the National Science Foundation, grants EB027170 and TR002636 awarded by the National Institutes of Health, and grant N00014-16-1-2550 awarded by the United States Navy. The government has certain rights in the invention.

BACKGROUND

Protein-based therapeutics are used for transient and accurate manipulation of cell functions because of their high specificities and low off-target effects. For example, clustered regularly interspaced short palindromic repeat associated protein 9, i.e., CRISPR/Cas9, demonstrates high flexibility and specificity for genome editing either via gene deletion, insertion, activation, and repression or via epigenetic modification. CRISPR/Cas9 facilitates disease modeling and identification of new treatments for various genetic disorders and infectious diseases.

A protein such as CRISPR/Cas9 must be delivered to its target site, i.e., an intracellular target, to achieve therapeutic effects. Yet, it has been a long-standing challenge to develop safe and efficient carriers for intracellular delivery of therapeutic proteins.

Conventional methods for delivering proteins include mechanical/physical techniques (e.g., microinjection, electroporation, and hydrodynamic injection) and carrier-based biochemical modifications (e.g., nuclear localization signal peptides, lipid or lipid-like nanocomplexes, and polymeric assemblies). The mechanical/physical techniques, although not requiring carriers, turn out to be invasive, raising practical issues for in vivo application. On the other hand, carriers used in biochemical modifications, while capable of delivering proteins intracellularly, exhibit significant limitations, e.g., low transfection efficiency and high cytotoxicity.

There is a need to develop a new carrier without the above-mentioned limitations for delivering a protein to its target site.

SUMMARY

The present invention relates to certain lipophilic compounds for forming lipid-like nanocomplexes that can be used for delivering a protein, e.g., CRISPR/Cas9, to its target site. Unexpectedly, these lipid-like nanocomplexes demonstrate higher transfection efficiency and lower cytotoxicity than Lipofectamine 2000 (Lpf2k), a commonly used commercial agent for delivering proteins.

In one aspect of this invention, it covers two sets of lipid-like compounds of formula (I) below:

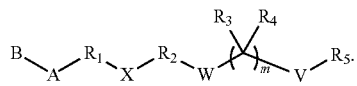

(I)

In one set, referring to formula (I), A is a hydrophilic head selected from

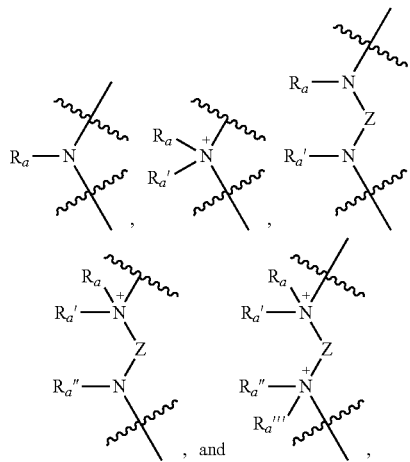

, and , in which each of $R_a$, $R_a'$, $R_a''$, and $R_a'''$, independently, is H, $C_1$-$C_{20}$ alkyl, $C_2$-$C_{20}$ alkenyl, $C_2$-$C_{20}$ alkynyl, $C_3$-$C_{20}$ cycloalkyl, $C_1$-$C_{20}$ heteroalkyl, $C_1$-$C_{20}$ heterocycloalkyl, aryl, or heteroaryl; and Z is a $C_1$-$C_{20}$ bivalent aliphatic radical, a $C_1$-$C_{20}$ bivalent heteroaliphatic radical, a bivalent aryl radical, or a bivalent heteroaryl radical; B is $C_1$-$C_{24}$ alkyl, $C_2$-$C_{24}$ alkenyl, $C_2$-$C_{24}$ alkynyl, $C_3$-$C_{24}$ cycloalkyl, $C_1$-$C_{24}$ heteroalkyl, $C_1$-$C_{24}$ heterocycloalkyl, aryl, or heteroaryl, or

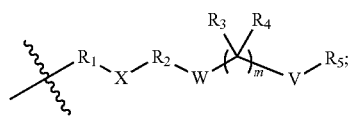

each of $R_1$ and $R_2$, independently, is a $C_1$-$C_{20}$ bivalent aliphatic radical; each of $R_3$ and $R_4$, independently, is H or $C_1$-$C_{10}$ alkyl, or $R_3$ and $R_4$, together with the atom to which they are attached, form $C_3$-$C_{10}$ cycloalkyl; $R_5$ is $C_1$-$C_{24}$ alkyl, $C_2$-$C_{24}$ alkenyl, $C_2$-$C_{24}$ alkynyl, $C_3$-$C_{24}$ cycloalkyl, $C_1$-$C_{24}$ heteroalkyl, $C_1$-$C_{24}$ heterocycloalkyl, aryl, or heteroaryl; W is O, S, or Se; V is a bond, O, S, or Se; X, a linker, is

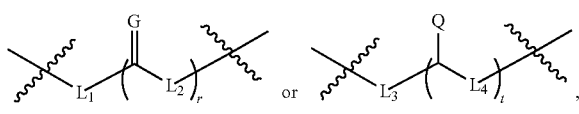

in which each of $L_1$, $L_2$, $L_3$, and $L_4$, independently, is a bond, O, S, or $NR_c$; G is O, S, or $NR_d$; Q is $OR_f$, $SR_g$, or $NR_hR_i$; and each of r and t, independently, is 1-6, each of $R_e$, $R_d$, $R_f$, $R_g$, $R_h$, and $R_i$, independently, being H, $C_1$-$C_{10}$ alkyl, $C_1$-$C_{10}$ heteroalkyl, aryl, or heteroaryl; and m is 0 or 1, provided that m is 1 when V is S.

In the other set, referring to formula (I) again, A is a hydrophilic head selected from

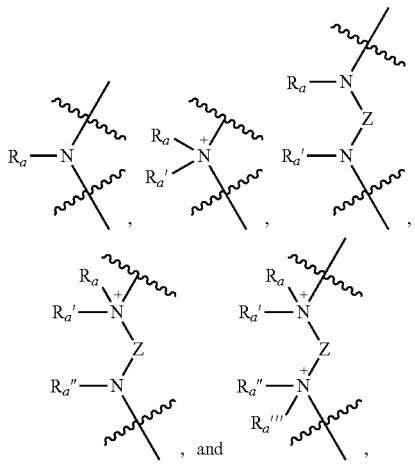

, and

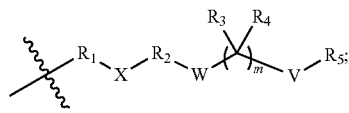

, in which each of $R_a$, $R_a'$, $R_a''$, and $R_a'''$, independently, is H, $C_1$-$C_{20}$ alkyl, $C_2$-$C_{20}$ alkenyl, $C_2$-$C_{20}$ alkynyl, $C_3$-$C_{20}$ cycloalkyl, $C_1$-$C_{20}$ heteroalkyl, $C_1$-$C_{20}$ heterocycloalkyl, aryl, or heteroaryl; and Z is a $C_1$-$C_{20}$ bivalent aliphatic radical, a $C_1$-$C_{20}$ bivalent heteroaliphatic radical, a bivalent aryl radical, or a bivalent heteroaryl radical; B is $C_1$-$C_{24}$ alkyl, $C_2$-$C_{24}$ alkenyl, $C_2$-$C_{24}$ alkynyl, $C_3$-$C_{24}$ cycloalkyl, $C_1$-$C_{24}$ heteroalkyl, $C_1$-$C_{24}$ heterocycloalkyl, aryl, or heteroaryl, or

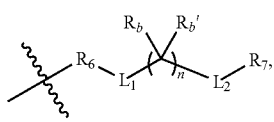

$R_1$ is a $C_1$-$C_{20}$ bivalent aliphatic radical; $R_2$ is a bond or $C_1$-$C_{20}$ bivalent aliphatic radical; each of $R_3$ and $R_4$, independently, is H or $C_1$-$C_{10}$ alkyl, or $R_3$ and $R_4$, together with the atom to which they are attached, form $C_3$-$C_{10}$ cycloalkyl; $R_5$ is

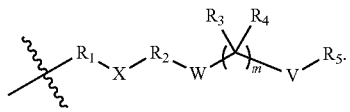

in which $R_6$ is a bond or $C_1$-$C_{20}$ bivalent aliphatic radical; each of $R_b$ and $R_b'$ is F or, $R_b$ and $R_b'$, together with the atom to which they are attached, form C=O; $R_7$ is F or an aliphatic lipid moiety; each of $L_1$ and $L_2$, independently, is a bond, O, S, or $NR_c$, $R_c$ being H, $C_1$-$C_{10}$ alkyl, $C_1$-$C_{10}$ heteroalkyl, aryl, or heteroaryl; and n is 1 to 20; each of W and V, independently, is a bond, O, S, or Se; X, a linker, is

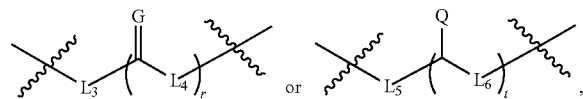

in which each of $L_3$, $L_4$, $L_5$, and $L_6$, independently, is a bond, O, S, or $NR_c$; G is O, S, or $NR_d$; Q is $OR_f$, $SR_g$, or $NR_hR_i$; and each of r and t, independently, is 1-6, each of $R_c$, $R_d$, $R_e$, $R_f$, $R_g$, $R_h$, and $R_i$, independently, being H, $C_1$-$C_{10}$ alkyl, $C_1$-$C_{10}$ heteroalkyl, aryl, or heteroaryl; and m is 0 or 1.

Typically, the above-described lipid-like compounds have variable A as either

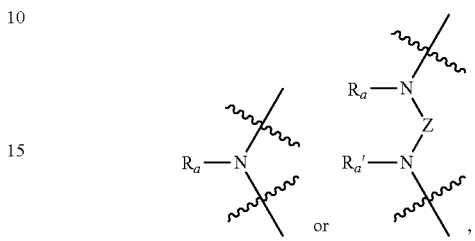

each of $R_a$ and $R_a'$, independently, being a $C_1$-$C_{10}$ monovalent aliphatic radical, a $C_1$-$C_{10}$ monovalent heteroaliphatic radical, a monovalent aryl radical, or a monovalent heteroaryl radical; and Z being a $C_1$-$C_{10}$ bivalent aliphatic radical, a $C_1$-$C_{10}$ bivalent heteroaliphatic radical, a bivalent aryl radical, or a bivalent heteroaryl radical. These compounds preferably have variable B as

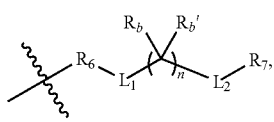

The term "lipid-like compounds" herein refers to compounds that contain one or more hydrophilic (or polar) amine-containing head groups and one or more hydrophobic (or nonpolar) hydrocarbon-containing tails. See, e.g., Love et al., PNAS, 2010, 107(5), 1864-1869. The term "lipid-like nanocomplexes" refers to nanocomplexes that contain one of lipid-like compounds. See, e.g., Wang et al., Angew. Chem. Int. Ed., 2014, 53(11), 2893-2898.

The term "aliphatic" herein refers to a saturated or unsaturated, linear or branched, acyclic, cyclic, or polycyclic hydrocarbon moiety. Examples include, but are not limited to, alkyl, alkylene, alkenyl, alkenylene, alkynyl, alkynylene, cycloalkyl, cycloalkylene, cycloalkenyl, cycloalkenylene, cycloalkynyl, and cycloalkynylene moieties.

The term "aliphatic lipid moiety" herein refers to a hydrophobic moiety that contains long-chain, saturated or unsaturated, linear or branched, acyclic, cyclic, or polycyclic hydrocarbons, alcohols, aldehydes, or carboxylic acids. Examples include, but are not limited to, cholesterol, desmosterol, and lanosterol.

The term "alkyl" or "alkylene" refers to a saturated, linear or branched hydrocarbon moiety, such as methyl, methylene, ethyl, ethylene, propyl, propylene, butyl, butylenes, pentyl, pentylene, hexyl, hexylene, heptyl, heptylene, octyl, octylene, nonyl, nonylene, decyl, decylene, undecyl, undecylene, dodecyl, dodecylene, tridecyl, tridecylene, tetradecyl, tetradecylene, pentadecyl, pentadecylene, hexadecyl, hexadecylene, heptadecyl, heptadecylene, octadecyl, octadecylene, nonadecyl, nonadecylene, icosyl, icosylene, triacontyl, and triacotylene. The term "alkenyl" or "alkenylene" refers to a linear or branched hydrocarbon moiety that contains at least one double bond, such as —CH=CH—$CH_3$ and —CH=CH—$CH_2$—. The term "alkynyl" or "alkynylene" refers to a linear or branched hydrocarbon moiety that contains at least one triple bond, such as —C≡C—$CH_3$ and —C≡C—$CH_2$—. The term "cycloalkyl" or "cycloalkylene" refers to a saturated, cyclic hydrocarbon moiety, such as cyclohexyl and cyclohexylene. The term "cycloalkenyl" or "cycloalkenylene" refers to a non-aromatic, cyclic hydrocarbon moiety that contains at least one double bond, such as cyclohexenyl cyclohexenylene. The term "cycloalkynyl" or "cycloalkynylene" refers to a non-aromatic, cyclic hydrocarbon moiety that contains at least one triple bond, cyclooctynyl and cyclooctynylene.

The term "heteroaliphatic" herein refers to an aliphatic moiety containing at least one heteroatom selected from N, O, P, B, S, Si, Sb, Al, Sn, As, Se, and Ge.

The term "alkoxy" herein refers to an —O-alkyl. Examples of alkoxy include methoxy, ethoxy, n-propoxy, isopropoxy, n-butoxy, iso-butoxy, sec-butoxy, and tert-butoxy.

The term "aryl" herein refers to a $C_6$ monocyclic, $C_{10}$ bicyclic, $C_{14}$ tricyclic, $C_{20}$ tetracyclic, or $C_{24}$ pentacyclic aromatic ring system. Examples of aryl groups include phenyl, phenylene, naphthyl, naphthylene, anthracenyl, anthracenylene, pyrenyl, and pyrenylene. The term "heteroaryl" herein refers to an aromatic 5-8 membered monocyclic, 8-12 membered bicyclic, 11-14 membered tricyclic, and 15-20 membered tetracyclic ring system having one or more heteroatoms (such as O, N, S, or Se). Examples of heteroaryl groups include furyl, furylene, fluorenyl, fluorenylene, pyrrolyl, pyrrolylene, thienyl, thienylene, oxazolyl, oxazolylene, imidazolyl, imidazolylene, benzimidazolyl, benzimidazolylene, thiazolyl, thiazolylene, pyridyl, pyridylene, pyrimidinyl, pyrimidinylene, quinazolinyl, quinazolinylene, quinolinyl, quinolinylene, isoquinolyl, isoquinolylene, indolyl, and indolylene.

Unless specified otherwise, aliphatic, heteroaliphatic, alkoxy, alkyl, alkylene, alkenyl, alkenylene, alkynyl, alkynylene, cycloalkyl, cycloalkylene, cycloalkenyl, cycloalkenylene, cycloalkynyl, cycloalkynylene, heterocycloalkyl, heterocycloalkylene, heterocycloalkenyl, heterocycloalkenylene, aryl, and heteroaryl mentioned herein include both substituted and unsubstituted moieties. Possible substituents on cycloalkyl, cycloalkylene, cycloalkenyl, cycloalkenylene, cycloalkynyl, cycloalkynylene, heterocycloalkyl, heterocycloalkylene, heterocycloalkenyl, heterocycloalkenylene, aryl, and heteroaryl include, but are not limited to, $C_1$-$C_{10}$ alkyl, $C_2$-$C_{10}$ alkenyl, $C_2$-$C_{10}$ alkynyl, $C_1$-$C_{20}$ alkoxy, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_2$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on aliphatic, heteroaliphatic, alkyl, alkylene, alkenyl, alkenylene, alkynyl, and alkynylene include all of the above-recited substituents except $C_1$-$C_{10}$ alkyl. Cycloalkyl, cycloalkylene, cycloalkenyl, cycloalkenylene, heterocycloalkyl, heterocycloalkylene, heterocycloalkenyl, heterocycloalkenylene, aryl, and heteroaryl can also be fused with each other.

The lipid-like compounds described above include the compounds themselves, as well as their salts and solvates, if applicable. A salt, for example, can be formed between an anion and a positively charged group (e.g., amino) on a lipid-like compound. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a lipid-like compound. Suitable cations include sodium ion, potassium ion, magnesium ion, calcium ion, and an ammonium cation such as tetramethylammonium ion. The lipid-like compounds also include those salts containing quaternary nitrogen atoms. A solvate refers to a complex formed between a lipid-like compound and a pharmaceutically acceptable solvent. Examples of pharmaceutically acceptable solvents include water, ethanol, isopropanol, ethyl acetate, acetic acid, and ethanolamine.

Another aspect of this invention relates to a pharmaceutical composition containing a nanocomplex formed of a lipid-like compound described above and a protein or a nucleic acid. In this composition, the nanocomplex has a particle size of 50 to 1000 nm (e.g., 50 to 500 nm, 50 to 300 nm, and 50 to 180 nm). The lipid-like compound binds to the protein or nucleic acid via a non-covalent interaction, a covalent bond, or both.

The term "protein" refers to a polymer of natural or non-natural amino acids linked together by amide bonds and having a molecular weight of 800 Dalton or higher. The term "nucleic acid" refers to a polymer of nucleotides linked together by phosphodiester bonds, having a molecular weight of 800 Dalton or higher. Both of these polymers can be chemically modified. Examples of protein modification include PEGylation and carboxylation of amine groups in lysine residues contained therein. More specifically, carboxylation of proteins or peptides can be achieved by using cis-aconitic anhydride. See Lee et al., Angew. Chem. Int. Ed., 2009, 48, 5309-5312; Lee et al., Angew. Chem. Int. Ed., 2010, 49, 2552-2555; and Maier et al., Journal of the American Chemical Society, 2012, 134, 10169-10173.

The term "non-covalent interaction" refers to any non-covalent binding, which includes ionic interaction, hydrogen bonding, van der Waals interaction, and hydrophobic interaction.

The pharmaceutical composition typically contains a pharmaceutically acceptable carrier. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active glycoside compound. Examples of other carriers include colloidal silicon oxide, magnesium stearate, cellulose, sodium lauryl sulfate, and D&C Yellow #10.

Further covered by this invention is a method of treating a medical condition, e.g., a lung disease. The method includes a step of administering to a subject in need thereof an effective amount of an above-described pharmaceutical composition.

The details of the invention are set forth in the description below. Other features, objects, and advantages of the invention will be apparent from the following drawings and detailed description of several embodiments, and also from the appending claims.

BRIEF DESCRIPTION OF THE DRAWINGS

FIG. 28 is a bar graph showing the percentage of GFP+ cells as a function of the lipidoid (derived from lipids synthesized from different cyclic amine analogues) used for protein delivery for.

DETAILED DESCRIPTION

Figure 1:
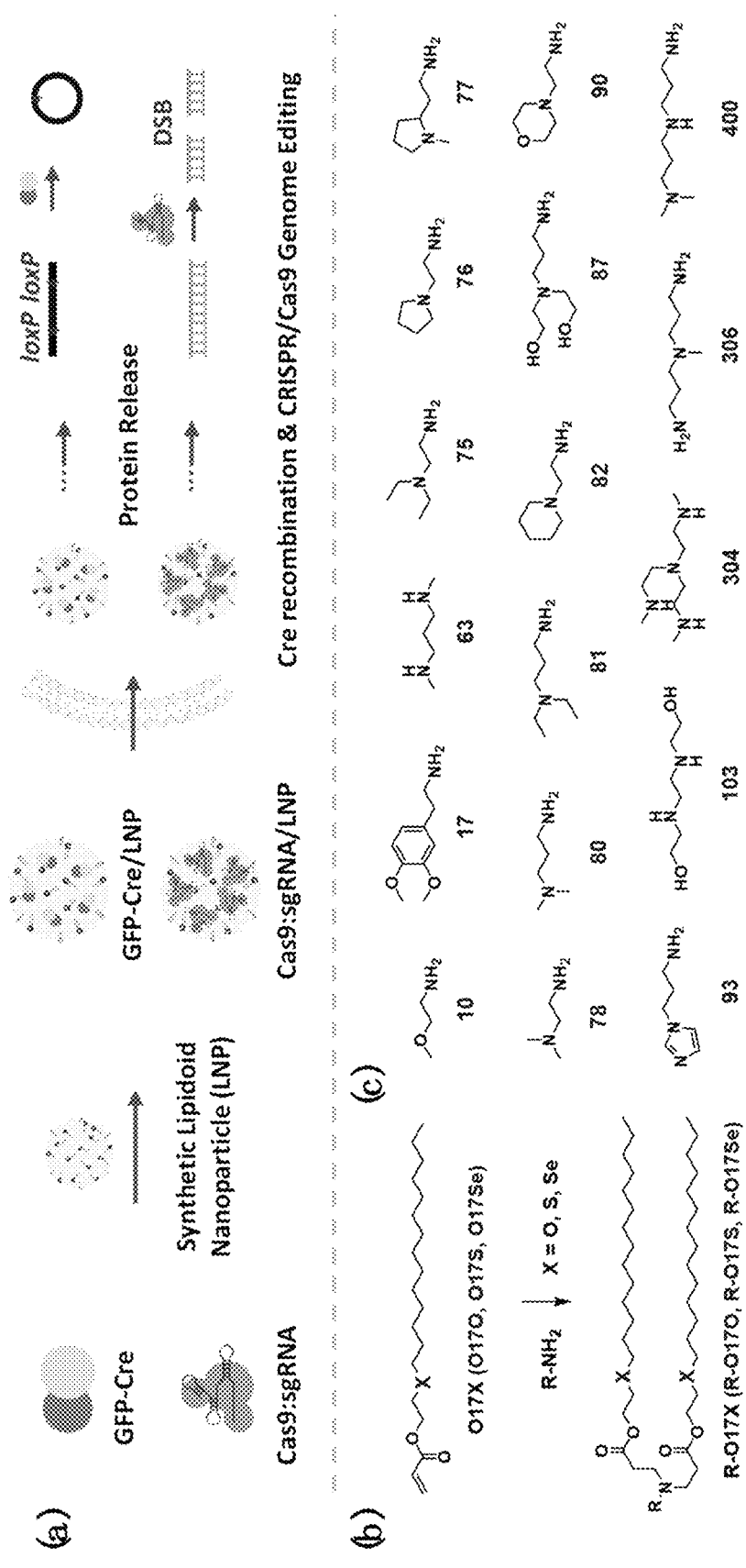
FIG. 1 is a schematic depiction of synthesis of lipid-like compounds (lipidoids) and encapsulation of proteins into lipidoid nanoparticles. (a) Encapsulation of negatively charged GFP-Cre and Cas9:sgRNA into synthetic cationic lipidoid nanoparticles (LNPs) for intracellular protein delivery and genome editing. (b) Synthetic route and lipidoids nomenclature. (c) Chemical structures of amine heads for lipidoids synthesis.

Disclosed in detail herein are lipid-like compounds of the present invention. More specifically, two embodiments are described in order below.

In the first embodiment, referring to formula (I) shown above, A is a hydrophilic head selected from

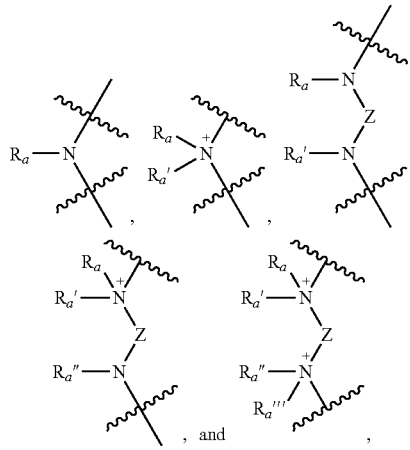

in which each of $R_a$, $R_a'$, $R_a''$, and $R_a'''$, independently, is H, $C_1$-$C_{20}$ alkyl, $C_2$-$C_{20}$ alkenyl, $C_2$-$C_{20}$ alkynyl, $C_3$-$C_{20}$ cycloalkyl, $C_1$-$C_{20}$ heteroalkyl, $C_1$-$C_{20}$ heterocycloalkyl, aryl, or heteroaryl; and Z is a $C_1$-$C_{20}$ bivalent aliphatic radical, a $C_1$-$C_{20}$ bivalent heteroaliphatic radical, a bivalent aryl radical, or a bivalent heteroaryl radical; B is $C_1$-$C_{24}$ alkyl, $C_2$-$C_{24}$ alkenyl, $C_2$-$C_{24}$ alkynyl, $C_3$-$C_{24}$ cycloalkyl, $C_1$-$C_{24}$ heteroalkyl, $C_1$-$C_{24}$ heterocycloalkyl, aryl, or heteroaryl, or

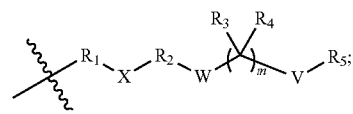

each of $R_1$ and $R_2$, independently, is a $C_1$-$C_{20}$ bivalent aliphatic radical; each of $R_3$ and $R_4$, independently, is H or $C_1$-$C_{10}$ alkyl, or $R_3$ and $R_4$, together with the atom to which they are attached, form $C_3$-$C_{10}$ cycloalkyl; $R_5$ is $C_1$-$C_{24}$ alkyl, $C_2$-$C_{24}$ alkenyl, $C_2$-$C_{24}$ alkynyl, $C_3$-$C_{24}$ cycloalkyl, $C_1$-$C_{24}$ heteroalkyl, $C_1$-$C_{24}$ heterocycloalkyl, aryl, or heteroaryl; W is O, S, or Se; V is a bond, O, S, or Se; X, a linker, is

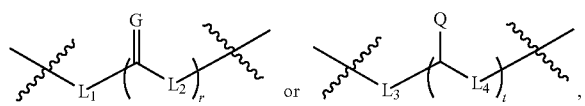

in which each of $L_1$, $L_2$, $L_3$, and $L_4$, independently, is a bond, O, S, or $NR_c$; G is O, S, or $NR_d$; Q is $OR_f$, $SR_g$, or $NR_hR_i$; and each of r and t, independently, is 1-6, each of $R_c$, $R_d$, $R_f$, $R_g$, $R_h$, and $R_i$, independently, being H, $C_1$-$C_{10}$ alkyl, $C_1$-$C_{10}$ heteroalkyl, aryl, or heteroaryl; and m is 0 or 1, provided that m is 1 when V is S.

This embodiment preferably includes compounds that typically have variable A as

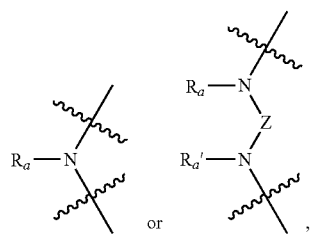

and variable B as

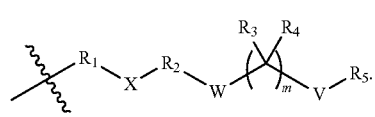

Exemplary compounds have variables A, B, and $R_1$-$R_5$ as follows: A is

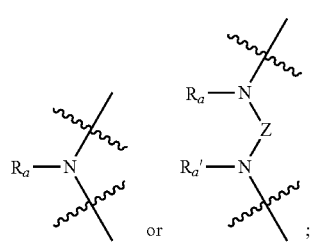

B is

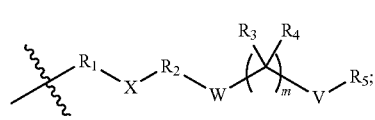

each of $R_1$ and $R_2$, independently, is a $C_1$-$C_4$ bivalent aliphatic radical; each of $R_3$ and $R_4$, independently, is H or $C_1$-$C_4$ alkyl; and $R_5$ is $C_1$-$C_{20}$ alkyl.

Preferably, A is an amino moiety formed from one of the following amines:

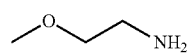 10

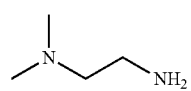 78

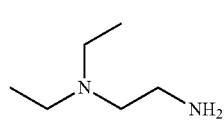 75

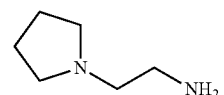 76

-continued

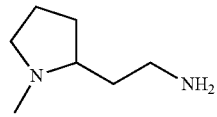 77

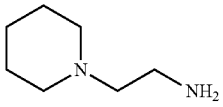 82

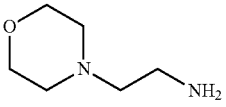 90

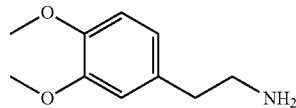 17

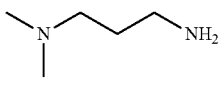 80

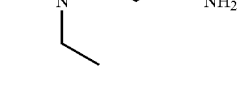 81

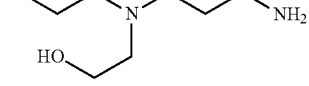 87

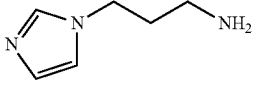 93

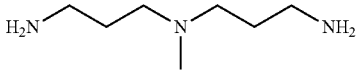 306

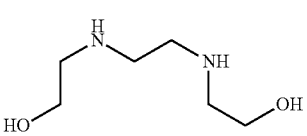 103

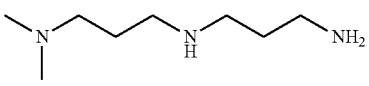 400

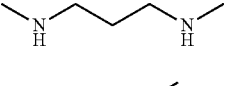 63

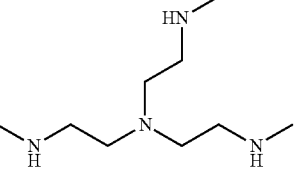 304

As described above, X is a linker. Examples of X include, but are not limited to,

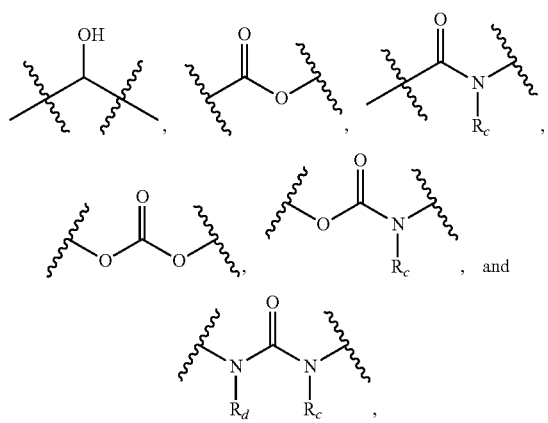

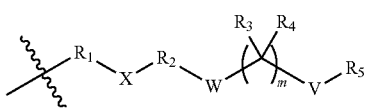

moiety formed from one of the following molecules:

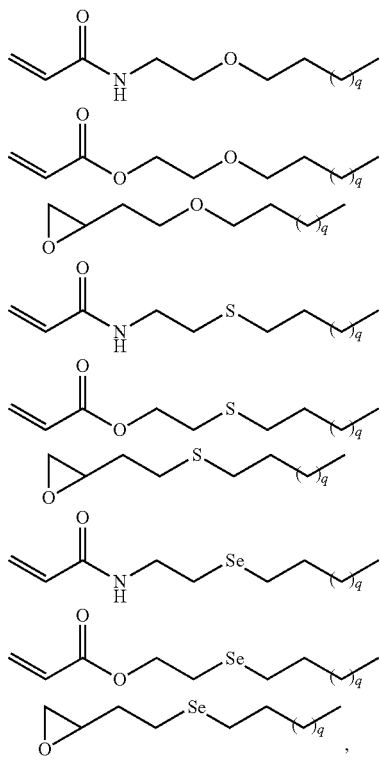

each of $R_c$ and $R_d$, independently, being H or $C_1$-$C_{10}$ alkyl. These compounds preferably have each of $R_1$ and $R_2$, independently, as a $C_1$-$C_4$ bivalent aliphatic radical; each of $R_3$ and $R_4$, independently, as H or $C_1$-$C_4$ alkyl; and $R_5$ as $C_1$-$C_{20}$ alkyl.

Turning to variables W, V, and m, this embodiment can include, based on these three variables, the following three subsets of compounds.

Subset (i) includes the compounds of formula (I), in which each of W and V, independently, is O or Se; and m is 0.

This subset of compounds can have their

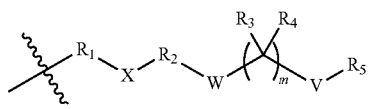

moiety formed from one of the following molecules:

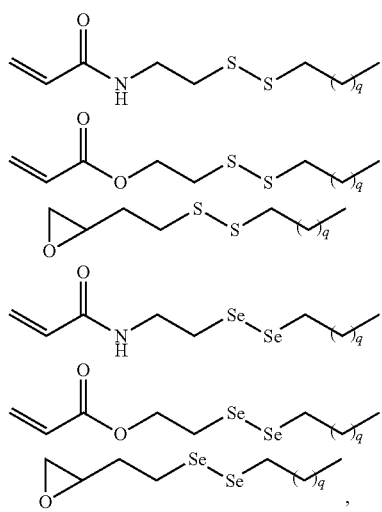

in which q is an integer of 8-12.

Subset (ii) includes the compounds of formula (I), in which W is O, S, or Se; V is a bond; and m is 0 or 1.

in which q is an integer of 8-12.

Subset (iii) includes the compounds of formula (I), in which each of W and V is O, or S and m is 1.

This subset of compounds can have their

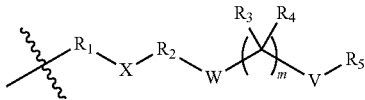

moiety formed from one of the following molecules:

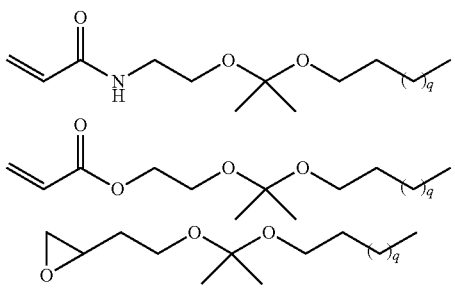

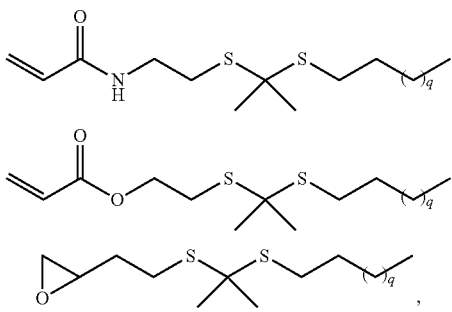

in which q is an integer of 8-12.

Alternatively, this subset of compounds can have their

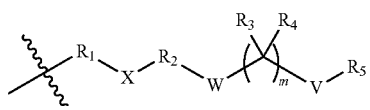

moiety formed from one of the following molecules:

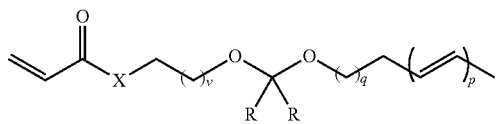

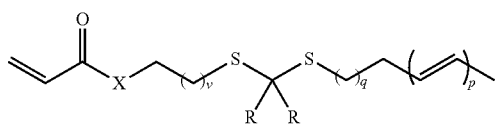

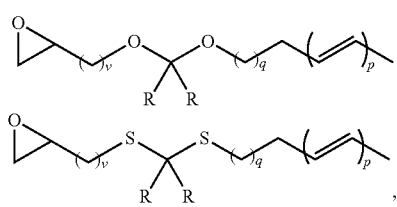

in which X is O, S, or NH; R is H or Me; p is an integer of 0-3; q is an integer of 1-16; and v is an integer of 1-10.

In the second embodiment, referring to the above formula (I) again, A is a hydrophilic head selected from

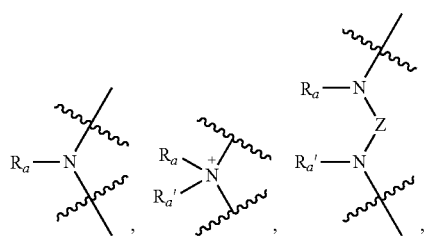

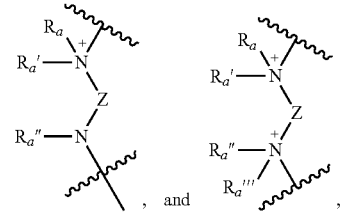

in which each of $R_a$, $R_a'$, $R_a''$, and $R_a'''$, independently, is H, $C_1$-$C_{20}$ alkyl, $C_2$-$C_{20}$ alkenyl, $C_2$-$C_{20}$ alkynyl, $C_3$-$C_{20}$ cycloalkyl, $C_1$-$C_{20}$ heteroalkyl, $C_1$-$C_{20}$ heterocycloalkyl, aryl, or heteroaryl; and Z is a $C_1$-$C_{20}$ bivalent aliphatic radical, a $C_1$-$C_{20}$ bivalent heteroaliphatic radical, a bivalent aryl radical, or a bivalent heteroaryl radical; B is $C_1$-$C_{24}$ alkyl, $C_2$-$C_{24}$ alkenyl, $C_2$-$C_{24}$ alkynyl, $C_3$-$C_{24}$ cycloalkyl, $C_1$-$C_{24}$ heteroalkyl, $C_1$-$C_{24}$ heterocycloalkyl, aryl, or heteroaryl, or

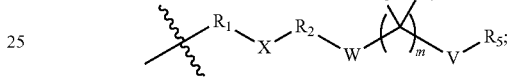

$R_1$ is a $C_1$-$C_{20}$ bivalent aliphatic radical; $R_2$ is a bond or $C_1$-$C_{20}$ bivalent aliphatic radical; each of $R_3$ and $R_4$, independently, is H or $C_1$-$C_{10}$ alkyl, or $R_3$ and $R_4$, together with the atom to which they are attached, form $C_3$-$C_{10}$ cycloalkyl; $R_5$ is

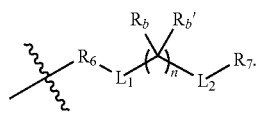

in which $R_6$ is a bond or $C_1$-$C_{20}$ bivalent aliphatic radical; each of $R_b$ and $R_b'$ is F or, $R_b$ and $R_b'$, together with the atom to which they are attached, form C=O; $R_7$ is F or an aliphatic lipid moiety; each of $L_1$ and $L_2$, independently, is a bond, O, S, or $NR_c$, $R_c$ being H, $C_1$-$C_{10}$ alkyl, $C_1$-$C_{10}$ heteroalkyl, aryl, or heteroaryl; and n is 1 to 20; each of W and V independently, is a bond, O, S, or Se; X, a linker, is

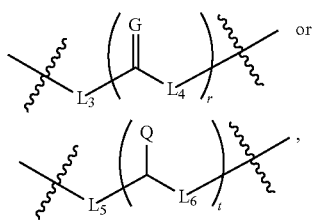

in which each of $L_3$, $L_4$, $L_5$, and $L_6$, independently, is a bond, O, S, or $NR_e$; G is O, S, or $NR_d$; Q is $OR_f$, $SR_g$, or $NR_hR_i$; and each of r and t, independently, is 1-6, each of $R_c$, $R_d$, $R_e$, $R_f$, $R_g$, $R_h$, and $R_i$, independently, being H, $C_1$-$C_{10}$ alkyl, $C_1$-$C_{10}$ heteroalkyl, aryl, or heteroaryl; and m is 0 or 1.

Like the first embodiment, the second embodiment can also include compounds having variable A as

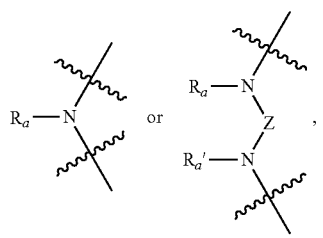
and variable B as
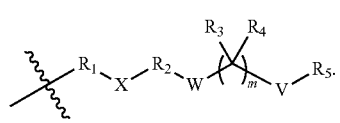
An exemplary compound of this embodiment has variables A, B, and $R_1$-$R_4$ as follows: A is
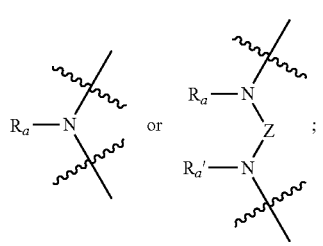
B is
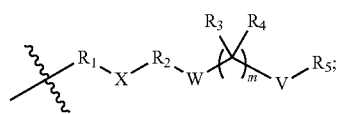
each of $R_1$ and $R_2$, independently, is a $C_1$-$C_4$ bivalent aliphatic radical; and each of $R_3$ and $R_4$, independently, is H or $C_1$-$C_4$ alkyl.
Again, A can be an amino moiety formed from one of the following amines:
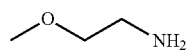
10
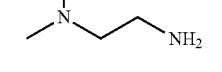
78
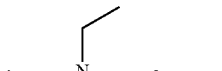
75
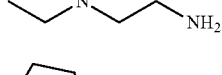
76
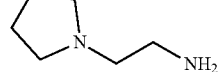
65
-continued
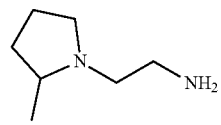
77
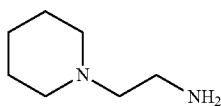
82
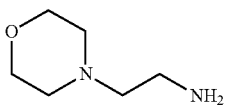
90
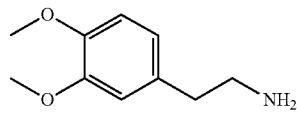
17
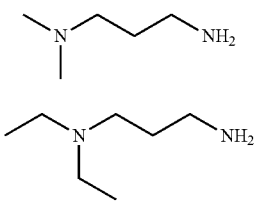
80
81
87
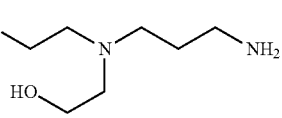
93
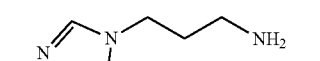
306
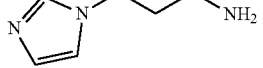
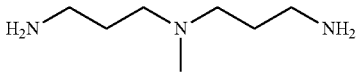
103
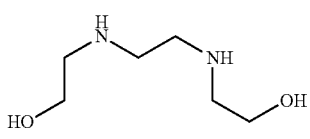
400
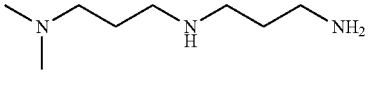
63
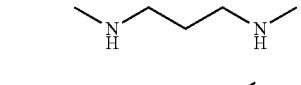
304
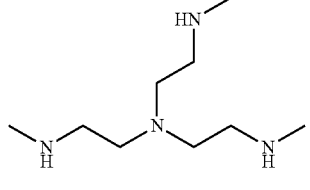
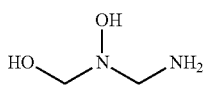
22

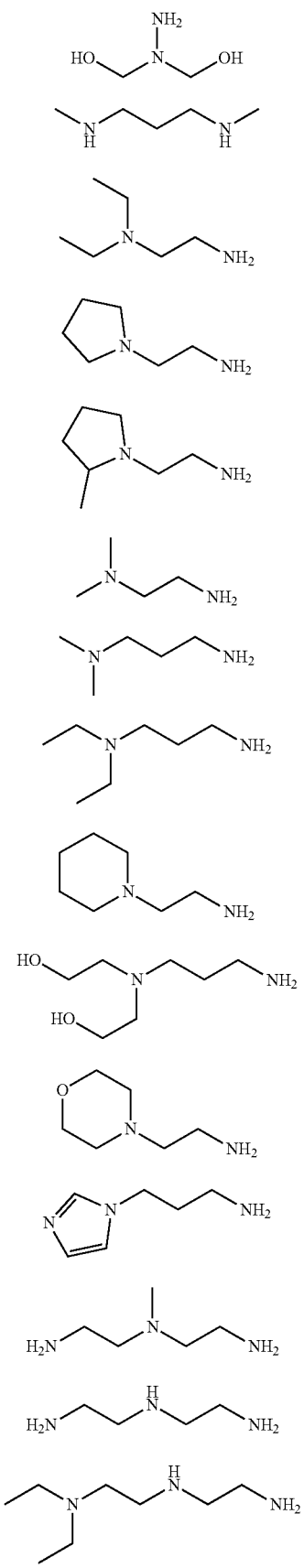
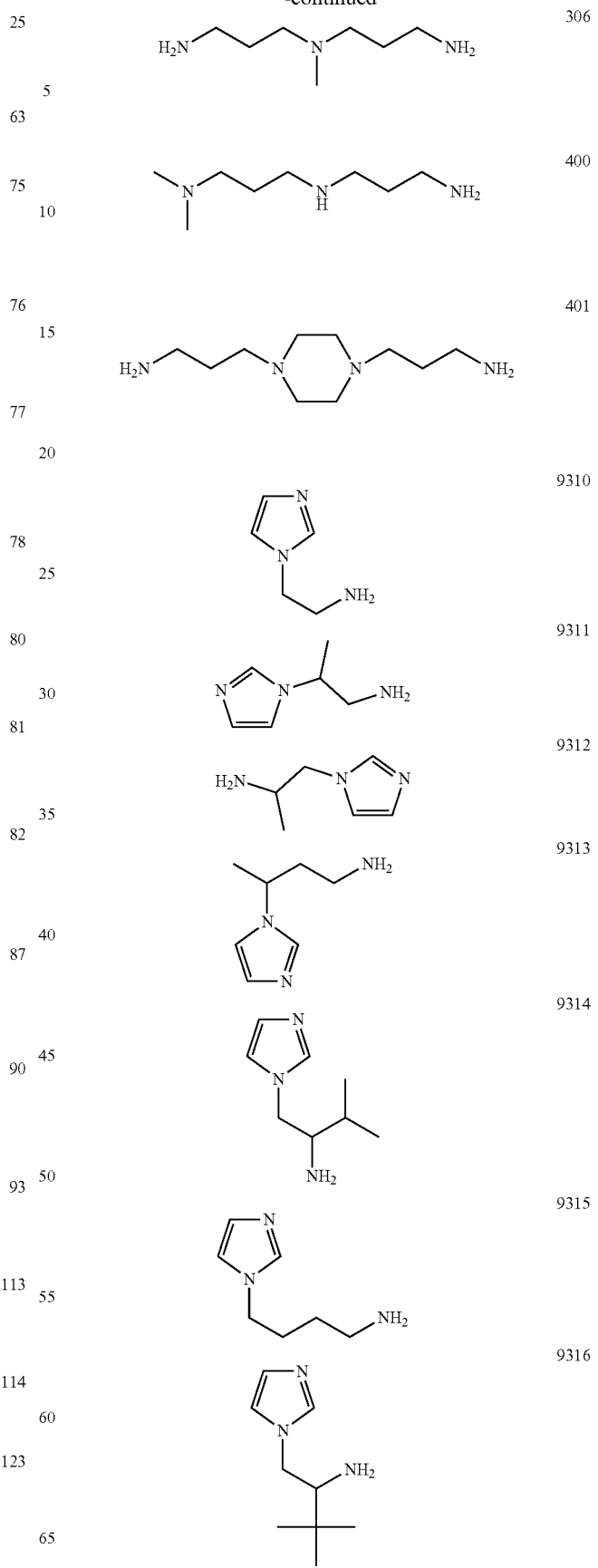

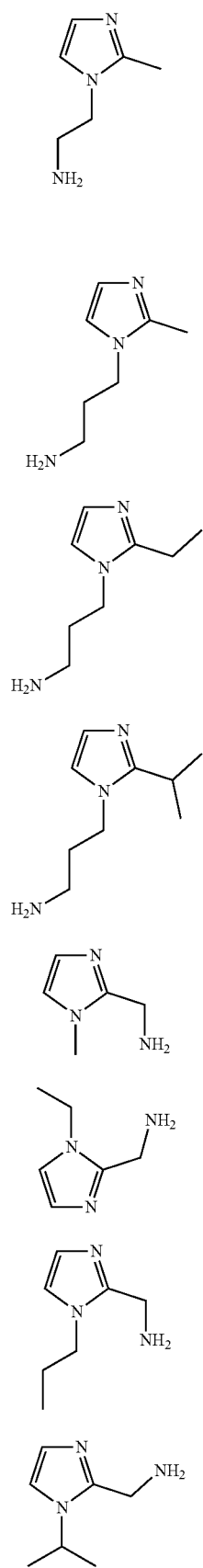
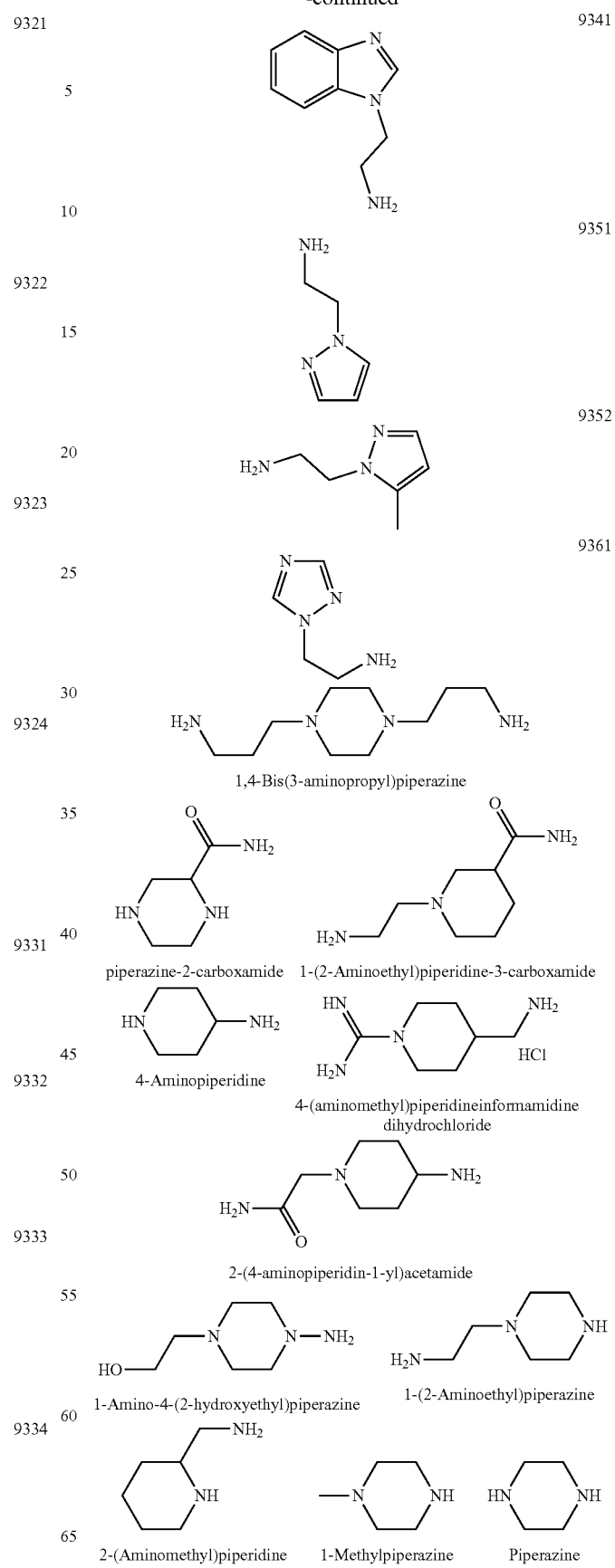

-continued

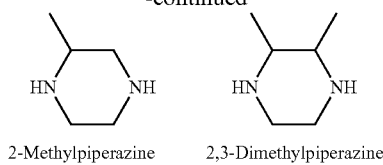

2-Methylpiperazine    2,3-Dimethylpiperazine

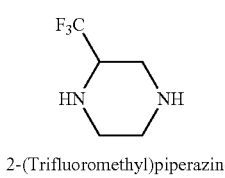

2-(Trifluoromethyl)piperazine    2-Oxopiperazine

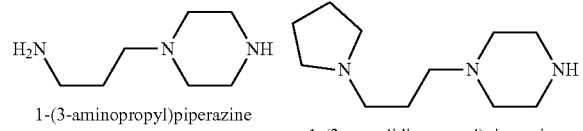

1-(3-aminopropyl)piperazine    1-(3-pyrrolidinopropyl)piperazine

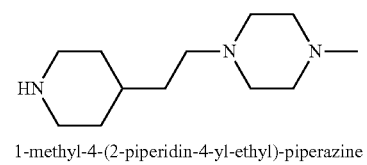

1-methyl-4-(2-piperidin-4-yl-ethyl)-piperazine

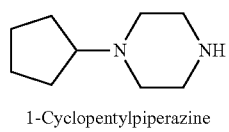

1-Cyclopentylpiperazine    2-(4-Methyl-piperazin-1-yl)-ethylamine

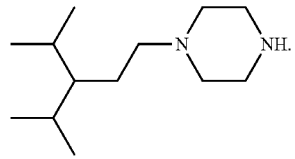

1-(2-diisopropylaminoethyl)piperazine

In the second embodiment, examples of X include, but are not limited to,

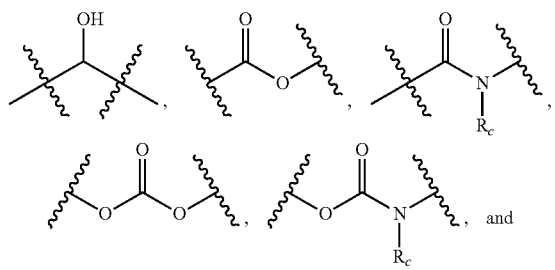

and

-continued

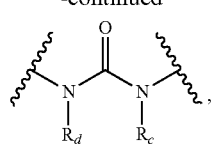

each of $R_c$ and $R_d$, independently, being H or $C_1$-$C_{10}$ alkyl. These compounds preferably have each of $R_1$ and $R_2$ as a $C_1$-$C_4$ bivalent aliphatic radical; each of $R_3$ and $R_4$, independently, as H or $C_1$-$C_4$ alkyl; and $R_5$ as $C_1$-$C_{20}$ alkyl.

As to variables W, V, and m, the second embodiment can include compounds having each of $R_2$, W, and V as a bond, and m as 0.

Referring to variable $R_5$, i.e.,

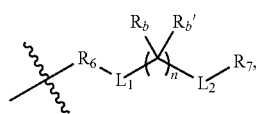

compounds in this embodiment can have each of $L_1$ and $L_2$ as a bond, and each of $R_b$, $R_b'$, and $R_7$ as F. Exemplary compounds have their

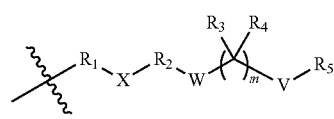

moiety formed from one of the following molecules:

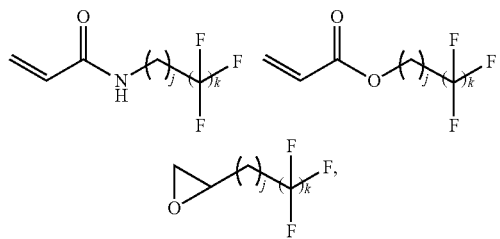

in which j is an integer of 0-10 and k is an integer of 1-20.

Alternatively, this embodiment includes those compounds, in which $R_6$ is $C_1$-$C_4$ bivalent aliphatic radical; each of $L_1$ and $L_2$, independently, is O or $NR_c$, $R_c$ being H or $C_1$-$C_{10}$ alkyl; $R_b$ and $R_b'$, together with the atom to which they are attached, form C=O; n is 1 or 2; and $R_7$ is an aliphatic lipid moiety. The aliphatic lipid moiety can be cholesterol. Exemplary compounds have their

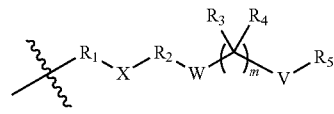

moiety formed from one of the following molecules:

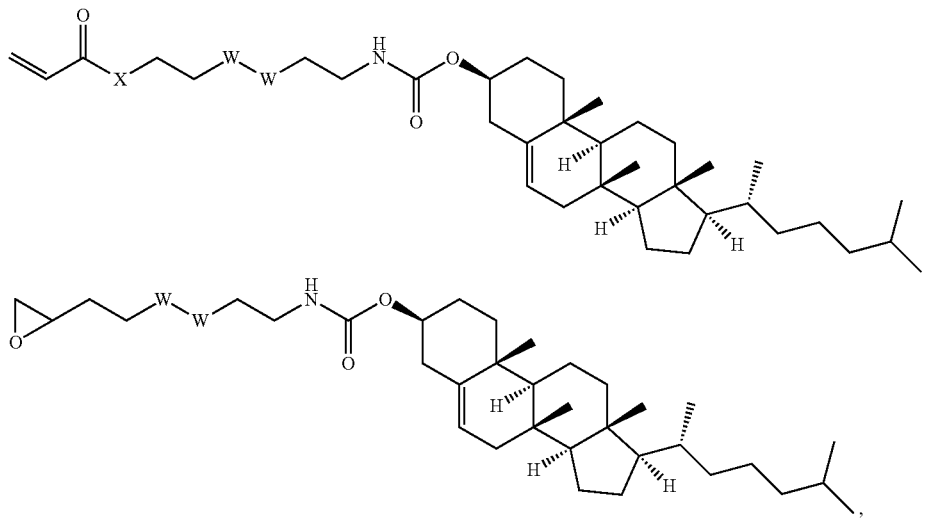

in which X is O or NH and W is O, S, or Se.

The lipid-like compounds of this invention can be prepared by methods well known in the art. See, e.g., Wang et al., ACS Synthetic Biology, 2012, 1, 403-407; Manoharan et al., WO 2008/042973; and Zugates et al., U.S. Pat. No. 8,071,082.

The synthetic route shown below exemplifies synthesis of certain lipid-like compounds described above:

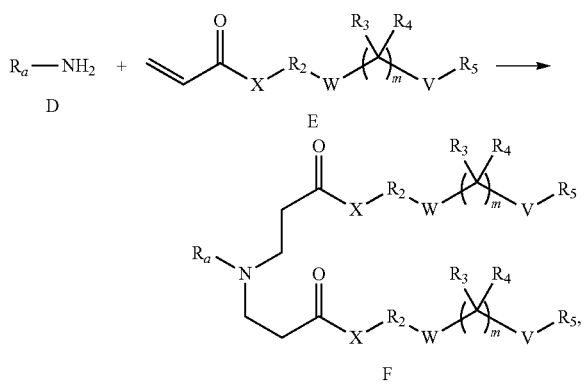

in which each of variables $R_a$, $R_2$-$R_5$, X, W, V, and m are defined above.

In this exemplary synthetic route, an amine compound, i.e., compound D, reacts with a vinyl carbonyl compound E to afford the final product, i.e., compound F. Amino compound D can be one of the above-described Compounds 10, 17, 63, 75-78, 80-82, 87, 90, 93, 103, 304, 306, and 400.

Other lipid-like compounds of this invention can be prepared using other suitable starting materials through the above-described synthetic route and others known in the art. The method set forth above can include an additional step(s) to add or remove suitable protecting groups in order to ultimately allow synthesis of the lipid-like compounds. In addition, various synthetic steps can be performed in an alternate sequence or order to give the desired material. Synthetic chemistry transformations and protecting group methodologies (protection and deprotection) useful in synthesizing applicable lipid-like compounds are known in the art, including, for example, R. Larock, Comprehensive Organic Transformations ($2^{nd}$ Ed., VCH Publishers 1999); P. G. M. Wuts and T. W. Greene, Greene's Protective Groups in Organic Synthesis ($4^{th}$ Ed., John Wiley and Sons 2007); L. Fieser and M. Fieser, Fieser and Fieser's Reagents for Organic Synthesis (John Wiley and Sons 1994); and L. Paquette, ed., Encyclopedia of Reagents for Organic Synthesis ($2^{nd}$ ed., John Wiley and Sons 2009) and subsequent editions thereof.

Certain lipid-like compounds may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

As mentioned above, these lipid-like compounds are useful for delivery of proteins or nucleic acids. They can be preliminarily screened for their efficacy in delivering pharmaceutical agents by an in vitro assay and then confirmed by animal experiments and clinic trials. Other methods will also be apparent to those of ordinary skill in the art.

Not to be bound by any theory, the lipid-like compounds facilitate delivery of proteins or nucleic acids by forming complexes, e.g., nanocomplexes and microparticles. The hydrophilic head of such a lipid-like compound, positively or negatively charged, binds to a moiety of a protein or nucleic acid that is oppositely charged and its hydrophobic moiety binds to a hydrophobic moiety of the protein or nucleic acid. Either binding can be covalent or non-covalent.

The above described complexes can be prepared using procedures described in publications such as Wang et al., ACS Synthetic Biology, 2012, 1, 403-407. Generally, they are obtained by incubating a lipid-like compound and a protein or nucleic acid in a buffer such as a sodium acetate buffer or a phosphate buffered saline ("PBS").

Further covered by this invention is a pharmaceutical composition containing a nanocomplex formed of a lipid-like compound described above and a protein or a nucleic acid. Again, the lipid-like compound binds to the protein or nucleic acid via a non-covalent interaction, a covalent bond, or both.

Examples of the protein or nucleic acid include, but are not limited to, clustered regularly interspaced short palindromic repeat associated protein 9 (CRISPR/Cas9), Cre recombinase ((-30)GFP-Cre), and Cas9:single-guide RNA (Cas9:sgRNA) ribonucleoprotein (RNP) or Cas9:sgRNA RNP.

Still within the scope of this invention is a method of treating a medical condition, e.g., a lung disease, with the above-described pharmaceutical composition. The method includes administering to a subject (e.g., a patient) in need thereof an effective amount of the pharmaceutical composition.

The term "an effective amount" refers to the amount of complexes that is required to confer a therapeutic effect on the treated subject. Effective doses will vary, as recognized by those skilled in the art, depending on the types of diseases treated, route of administration, excipient usage, and the possibility of co-usage with other therapeutic treatment.

To practice the method of the present invention, a composition having the above-described complexes can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition containing the nanocomplexes can also be administered in the form of suppositories for rectal administration.

EXAMPLES

Without further elaboration, it is believed that one skilled in the art can, based on the above description, utilize the present invention to its fullest extent. The following specific examples are therefore to be construed as merely illustrative, and not limitative of the remainder of the disclosure in any way whatsoever.

Methods and Materials

General

All chemicals used for lipidoids synthesis were purchased from Sigma-Aldrich without further purification unless otherwise noted. (-30)GFP-Cre recombinase, *S. pyogenes* Cas9 (spCas9) and sgRNA were generated following the protocols reported in Wang at al., Proc. Natl. Acad. Sci. USA, 2016, 113, 2868-2873 ("Wang"). HeLa-DsRed and GFP-HEK cells were cultured in Dulbecco's modified eagle's medium (DMEM, Sigma-Aldrich) with 10% fetal bovine serum (FBS, Sigma-Aldrich) and 1% penicillin-streptomycin (Gibco). All $^1$H NMR spectra were recorded on a Bruker AVIII 500 MHz NMR spectrometer operated in the Fourier transform mode. Hydrodynamic size and polydispersity index of nanoparticles were measured by Zeta-PALS particle size analyzer (Brookhaven Instruments). The apparent pKa values of lipidoids were determined using 2-(p-toluidinynaphthalene-6-sulphonic acid) (TNS, Sigma-Aldrich) as fluorescent probe following the protocols reported in Heyes et al., J. Controlled Release, 2005, 107, 276-287. TEM measurements were performed on a FEI Technai Transmission Electron Microscope. Fluorescence images of tissue slices were obtained using BZ-X Analyzer fluorescence microscope.

Synthesis of Lipid-Like Compounds (i.e., Lipidoids)

Head amines (Sigma-Aldrich) were mixed with acrylates tails (e.g., O17O, O17S, and O17Se) at a molar ratio of 1:2.4 in teflon-lined glass screw-top vials for 48 hours at 70° C. The crude products were purified using a Teledyne Isco Chromatography system.

One class of lipid-like compounds of formula (I) were synthesized by following the synthetic route shown below:

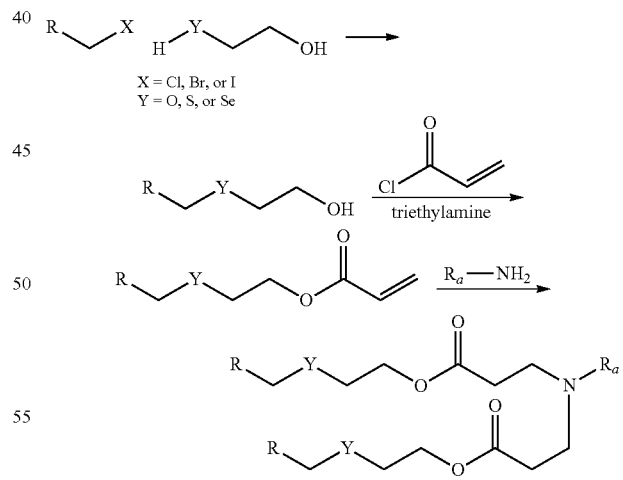

Head amines $R_a$—$NH_2$ shown in the above scheme were selected from Compounds 10, 17, 63, 75-78, 80-82, 87, 90, 93, 103, 304, 306, and 400.

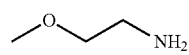

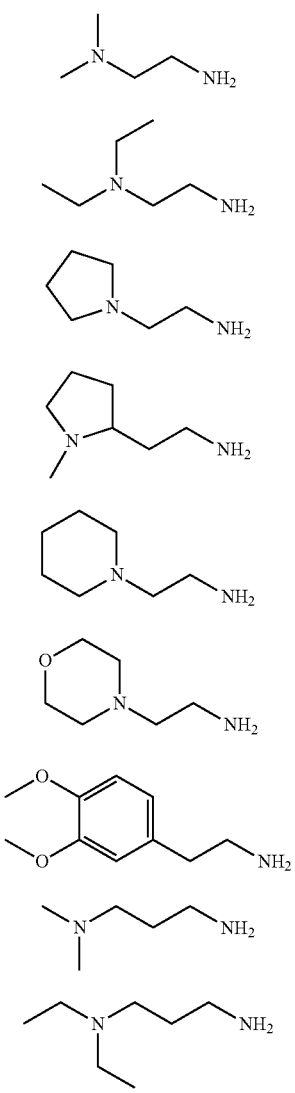

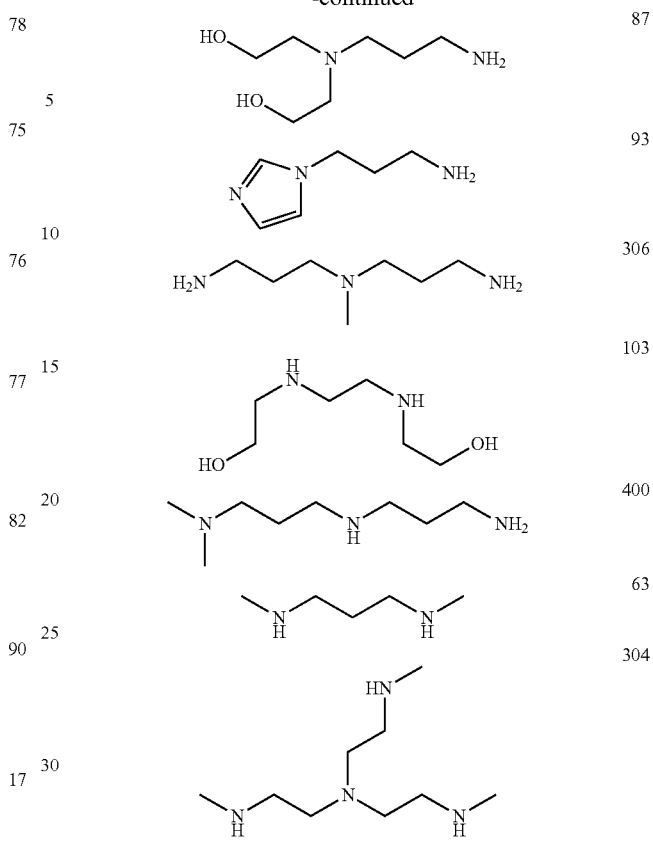

Shown in the table below are the codes, chemical formulas, and analytical data (ESI-MS) of 51 exemplary lipid-like compounds ("lipidoids") of formula (I). Note that each lipidoid is coded as X-O17Y, in which X represents the number of an amino compound and Y represents O, S, or Se. Code X-O17Y indicates that a lipidoid is formed from an amine of Compound X and a lipid molecule of O17Y (Y being O, S, or Se).

For example, lipidoid 10-O17O is formed from amine Compound 10 and lipid molecule O17O as follows:

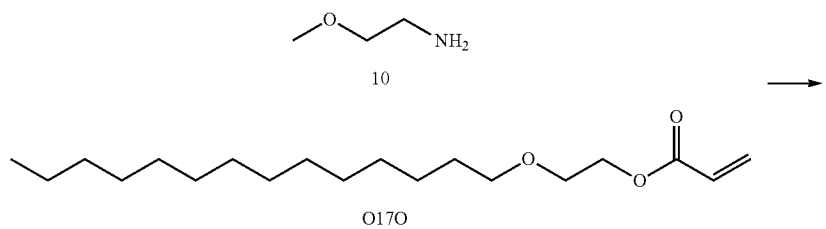

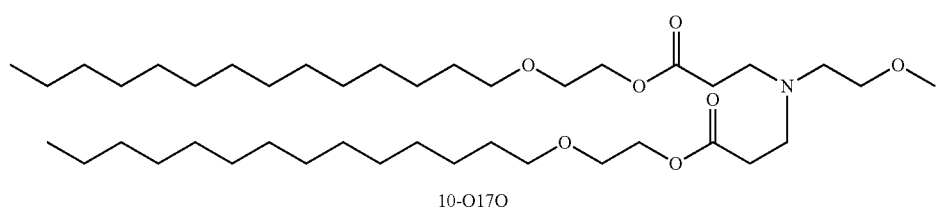

10-O17O

Each code in the table below contains O17O, O17S, or 8.7Se, which represents one of the three molecules:

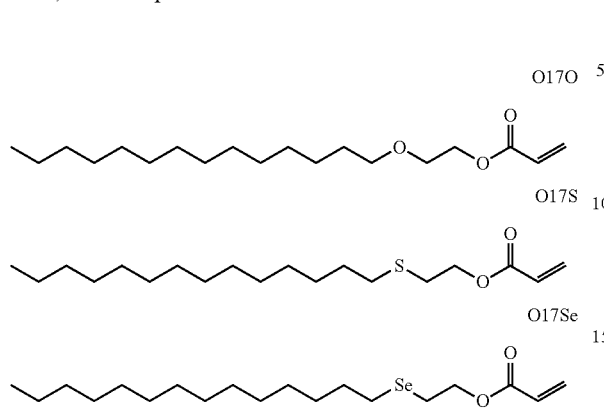

| Lipidoid Code | Chemical Formula | Cal. [M + H]+ | Found [M + H]+ |
|---|---|---|---|
| 10-O17O | $C_{41}H_{82}NO_7$ | 700.61 | 700.70 |
| 10-O17S | $C_{41}H_{82}NO_5S_2$ | 732.56 | 732.59 |
| 10-O17Se | $C_{41}H_{82}NO_5Se_2$ | 828.45 | 828.27 |
| 17-O17O | $C_{48}H_{88}NO_8$ | 806.65 | 806.63 |
| 17-O17S | $C_{48}H_{88}NO_6S_2$ | 838.60 | 838.49 |
| 17-O17Se | $C_{48}H_{88}NO_6Se_2$ | 934.49 | 934.27 |
| 63-O17O | $C_{43}H_{87}N_2O_6$ | 727.66 | 727.67 |
| 63-O17S | $C_{43}H_{87}N_2O_4S_2$ | 759.61 | 759.62 |
| 63-O17Se | $C_{43}H_{87}N_2O_4Se_2$ | 855.50 | 855.35 |
| 75-O17O | $C_{44}H_{89}N_2O_6$ | 741.67 | 741.71 |
| 75-O17S | $C_{44}H_{89}N_2O_4S_2$ | 773.63 | 773.69 |
| 75-O17Se | $C_{44}H_{89}N_2O_4Se_2$ | 869.51 | 869.67 |
| 76-O17O | $C_{44}H_{87}N_2O_6$ | 739.66 | 739.74 |
| 76-O17S | $C_{44}H_{87}N_2O_4S_2$ | 771.61 | 771.69 |
| 76-O17Se | $C_{44}H_{87}N_2O_4Se_2$ | 867.50 | 867.46 |
| 77-O17O | $C_{45}H_{89}N_2O_6$ | 753.67 | 753.75 |
| 77-O17S | $C_{45}H_{89}N_2O_4S_2$ | 785.63 | 785.64 |
| 77-O17Se | $C_{45}H_{89}N_2O_4Se_2$ | 881.51 | 881.46 |
| 78-O17O | $C_{42}H_{85}N_2O_6$ | 713.64 | 713.79 |
| 78-O17S | $C_{42}H_{85}N_2O_4S_2$ | 745.59 | 745.57 |
| 78-O17Se | $C_{42}H_{85}N_2O_4Se_2$ | 841.48 | 841.43 |
| 80-O17O | $C_{43}H_{87}N_2O_6$ | 727.66 | 727.68 |
| 80-O17S | $C_{43}H_{87}N_2O_4S_2$ | 759.61 | 759.70 |
| 80-O17Se | $C_{43}H_{87}N_2O_4Se_2$ | 855.50 | 855.46 |
| 81-O17O | $C_{45}H_{91}N_2O_6$ | 755.69 | 755.71 |
| 81-O17S | $C_{45}H_{91}N_2O_4S_2$ | 787.64 | 787.64 |
| 81-O17Se | $C_{45}H_{91}N_2O_4Se_2$ | 883.53 | 883.45 |
| 82-O17O | $C_{45}H_{89}N_2O_6$ | 753.67 | 753.88 |
| 82-O17S | $C_{45}H_{89}N_2O_4S_2$ | 785.63 | 785.70 |
| 82-O17Se | $C_{45}H_{89}N_2O_4Se_2$ | 881.51 | 881.42 |
| 87-O17O | $C_{45}H_{91}N_2O_8$ | 787.68 | 787.71 |
| 87-O17S | $C_{45}H_{91}N_2O_6S_2$ | 819.63 | 819.52 |
| 87-O17Se | $C_{45}H_{91}N_2O_6Se_2$ | 915.52 | 915.39 |
| 90-O17O | $C_{44}H_{87}N_2O_7$ | 755.65 | 755.96 |
| 90-O17S | $C_{44}H_{87}N_2O_5S_2$ | 787.61 | 787.59 |
| 90-O17Se | $C_{44}H_{87}N_2O_5Se_2$ | 883.49 | 883.38 |
| 93-O17O | $C_{44}H_{84}N_3O_6$ | 750.64 | 750.69 |
| 93-O17S | $C_{44}H_{84}N_3O_4S_2$ | 782.59 | 782.69 |
| 93-O17Se | $C_{44}H_{84}N_3O_4Se_2$ | 878.48 | 878.41 |
| 103-O17O | $C_{44}H_{89}N_2O_8$ | 773.66 | 773.72 |
| 103-O17S | $C_{44}H_{89}N_2O_6S_2$ | 805.62 | 805.53 |
| 103-O17Se | $C_{44}H_{89}N_2O_6Se_2$ | 901.50 | 901.45 |
| 304-O17O | $C_{66}H_{133}N_4O_9$ | 1126.01 | 1125.97 |
| 304-O17S | $C_{66}H_{133}N_4O_6S_3$ | 1173.94 | 1173.88 |
| 304-O17Se | $C_{66}H_{133}N_4O_6Se_3$ | 1317.77 | 1317.63 |
| 306-O17O | $C_{83}H_{164}N_3O_{12}$ | 1395.23 | 1395.24 |
| 306-O17S | $C_{83}H_{164}N_3O_8S_4$ | 1459.14 | 1459.89 |
| 306-O17Se | $C_{83}H_{164}N_3O_8Se_4$ | 1650.92 | 1650.77 |
| 400-O17O | $C_{65}H_{130}N_3O_9$ | 1096.98 | 1096.90 |
| 400-O17S | $C_{65}H_{130}N_3O_6S_3$ | 1144.91 | 1144.74 |
| 400-O17Se | $C_{65}H_{130}N_3O_6Se_3$ | 1288.74 | 1288.60 |

Another class of lipid-like compounds of formula (I) were synthesized by following the synthetic route shown below:

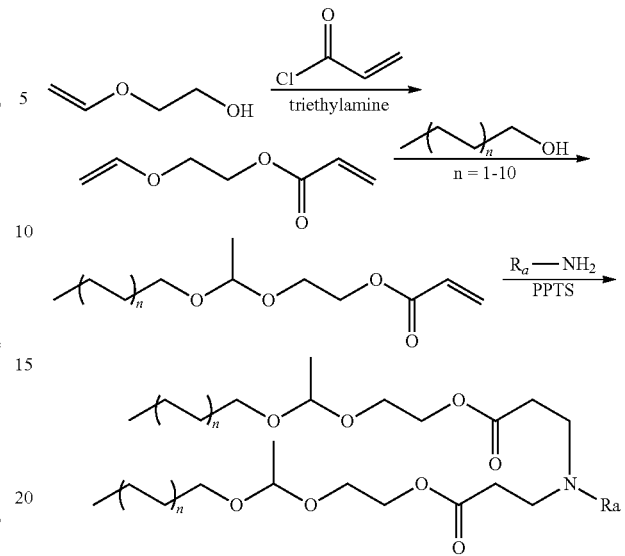

PPTS = pyridinium p-toluenesulfonate

Again, head amines $R_a$—$NH_2$ shown in this above scheme were selected from Compounds 10, 17, 63, 75-78, 80-82, 87, 90, 93, 103, 304, 306, and 400.

Still another class of lipid-like compounds of formula (I) were synthesized by following the synthetic route shown below:

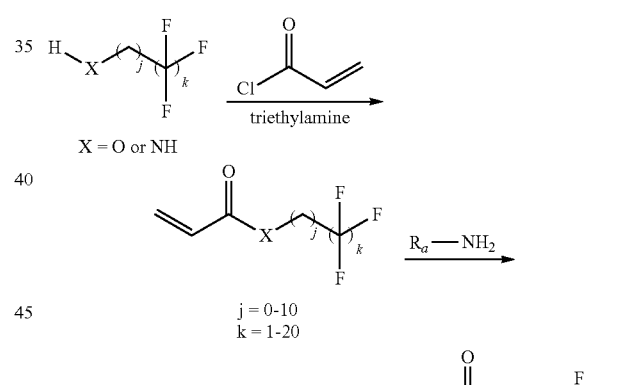

Head amines $R_a$—$NH_2$ shown in the above scheme were selected from Compounds 10, 17, 63, 75-78, 80-82, 87, 90, 93, 103, 304, 306, and 400.

Fabrication of Nanocomplexes from Lipidoids and Proteins.

Lipidoids were fabricated into nanoparticles for delivery proteins or nucleic acids. Briefly, lipidoids were mix with sodium acetate buffer (25 mM, pH 5.2), sonicated for 30 min in ultrasonic bath and followed by another 30 min of vigorous vortex to form lipid-like nanoparticles or LNPs. The LNPs thus obtained were stored at 4° C. For protein/LNP complexation, LNPs were mixed with (−30)GFP-Cre or Cas9:sgRNA in PBS buffer (25 mM, pH 7.4) following the protocols reported in Wang and incubated at room temperature for 30 minutes.

Evaluation of Phospholipid Bilayer Membrane Disruption

Human red blood cells (hRBCs) were washed with PBS buffer three times and collected after centrifugation at 1000 rpm for 5 minutes. The resulting stock solution (about 10% v/v hRBCs) was diluted 3 fold in PBS buffer to give the assay solution. 90 μL of assay solution was mixed with 10 μL of LNPs solutions (final concentration of lipidoids=3.3 mg/L) and incubated at 37° C. for 60 minutes. Then the samples were centrifuged again at 1000 rpm for 10 min. 10 μL of the supernatant was further diluted into 90 μL of PBS buffer, and the absorbance at 405 nm (OD405) was recorded using a microplate reader. The PBS buffer and Triton X-100 (1% v/v) were used as negative and positive controls respectively.

Intracellular Delivery of (−30)GFP-Cre/LNP

For the intracellular uptake study, HeLa-DsRed cells were seeded in 48-well plate with a density of $2 \times 10^4$ cell/well. After 24 h of incubation at 37° C., 5% $CO_2$, (−30)GFP-Cre/LNP nanoparticles were added to the cells and incubated for 6 h before fluorescence microscopy and flow cytometry (BD FACS Calibur, BD Science, CA) analysis (green emission from GFP). The final (−30)GFP-Cre protein concentration is 25 nM, and lipidoid concentration is 3.3 mg/L. For the gene recombination functional study, HeLa-DsRed cells were treated with same conditions and the red fluorescence emission from DsRed was analyzed by flow cytometry 24 h after delivery.

Intracellular Delivery of Cas9:sg RNA/LNP

For CRISPR/Cas9 gene knockout study, GFP-HEK cells were seeded in 48-well plate with a density of $2 \times 10^4$ cell/well. After 24 h of incubation, Cas9:sgRNA/LNP nanoparticles were added to the cells and incubated for 4 h, followed by media changed. After 48 h of incubation, the green emission from GFP was analyzed by flow cytometry. The final Cas9:sgRNA RNP concentration was 25 nM, and lipidoid concentration was 3.3 mg/L.

In Vitro Cytotoxicity Assay.

Cell viability was measured by the standard MTT assay. HeLa-DsRed or GFP-HEK cells were seeded into 96-well plate with a density of $5 \times 10^3$ cell/well. (−30)GFP-Cre/LNP or Cas9:sgRNA/LNP nanoparticles were added after 24 h of incubation. The final concentration of protein is 25 nM and LNP is 3.3 mg/L. After incubating for 24 h or 48 h, the MTT reagent (5 mg/mL, in 30 μL PBS buffer) was added and the cells were incubated for another 4 h at 37° C. The cell culture media were then carefully removed and 200 μL of DMSO were added. The DMSO solution was transferred into another 96-well plate and the absorbance at 570 nm was recorded by microplate reader. All experiments were performed in quadruplicate.

In Vivo Protein Delivery to Ai14 Mouse

Formulated LNPs (lipidoid/Cholesterol/DOPE/DSPE-PEG2k=16/4/1/4, weight ratio) were prepared for protein loading and mice injection. Ai14 mice were housed in a temperature and humidity controlled facility with a 12 h light/dark cycle. Two mice in each group were injected with (−30)GFP-Cre/LNPs formulations on day 0 and 5, with 100 μg protein for each injection. Organs including heart, liver, spleen, lung and kidney from all groups were collected 20 days after injections. The tissues were fixed overnight in 4% paraformaldehyde (PFA) before being sectioning into 10 μm slices. The slices were collected and stained with DAPI for fluorescence imaging.

Example 1: Preparation and Characterization of Lipid-Like Nanoparticles (LNPs)

Certain lipid-like nanoparticles (LNPs) were prepared from lipid-like compounds of formula (I), i.e., lipidoids, by following the procedures described below.

Synthesis of O17O

The following scheme was followed for synthesizing O17O.

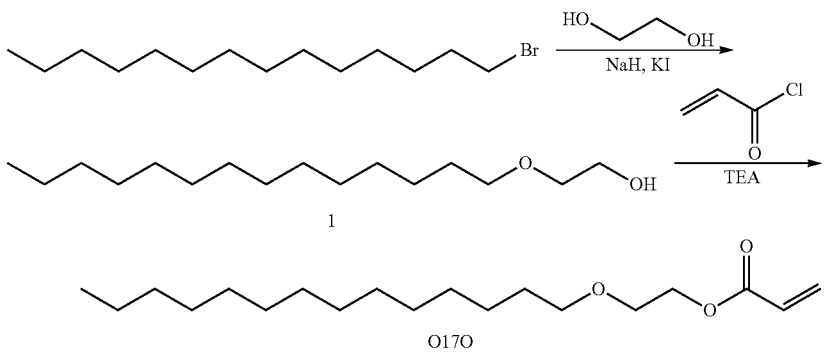

Sodium hydride (0.72 g, 30 mmol) was added to the solution of ethylene glycol (5.6 g, 90 mmol) in anhydrous DMF (30 mL) and stirred for 10 min at 0° C. 1-Bromotetradecane (6.0 g, 20 mmol) and KI (3.3 g, 20 mmol) were then added and the reaction mixture was kept at 95° C. for another 4 h. After cooling to room temperature, the mixture was diluted with cold water, extracted with ethyl acetate, and dried over anhydrous sodium sulfate. Compound 1 (3.3 g, yield about 65%) was obtained after column chromatography purification on silica gel using n-hexane/ethyl acetate as mobile phase. Then, compound 1 (3.3 g, 12.8 mmol) and triethylamine (TEA, 1.9 g, 19.2 mmol) were dissolved in anhydrous DCM (80 mL). Acryloyl chloride (1.4 g, 15.4 mmol) was added dropwise at 0° C., and the reaction mixture was stirred overnight. After column chromatography purification, O17O was obtained as colorless oil (3.2 g, yield about 82%). The structure of O17O was confirmed by $^1H$ NMR spectrum recorded in $CDCl_3$.

Synthesis of O17S

The following scheme was followed for synthesizing O17S.

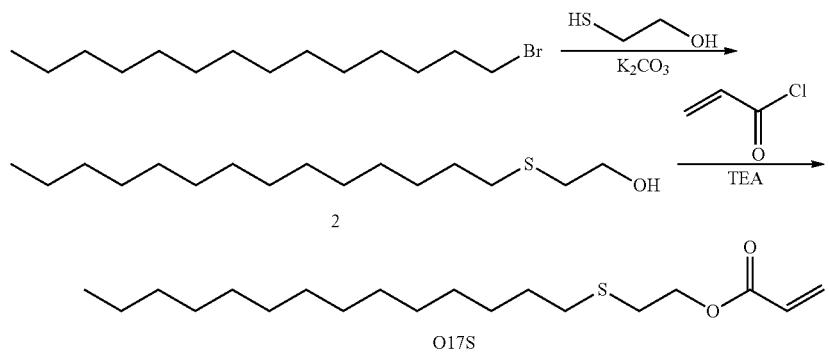

To a solution of 2-mercaptoethanol (1.1 g, 14 mmol) in acetonitrile (20 mL) was added 1-bromotetradecane (5.0 g, 18 mmol) and potassium carbonate (3.6 g, 26 mmol). The reaction solution was stirred overnight at 40° C., filtered and concentrated. Compound 2 (1.8 g, yield about 48%) was obtained after column chromatography purification on silica gel using n-hexane/ethyl acetate as mobile phase. In a manner similar to that for the preparation of O17O, O17S was synthesized and purified as oil-like liquid (3.5 g, yield about 75%). The structure of O17S was confirmed by $^1$H NMR spectrum recorded in CDCl$_3$.

Synthesis of O17Se

The following scheme was followed for synthesizing O17Se.

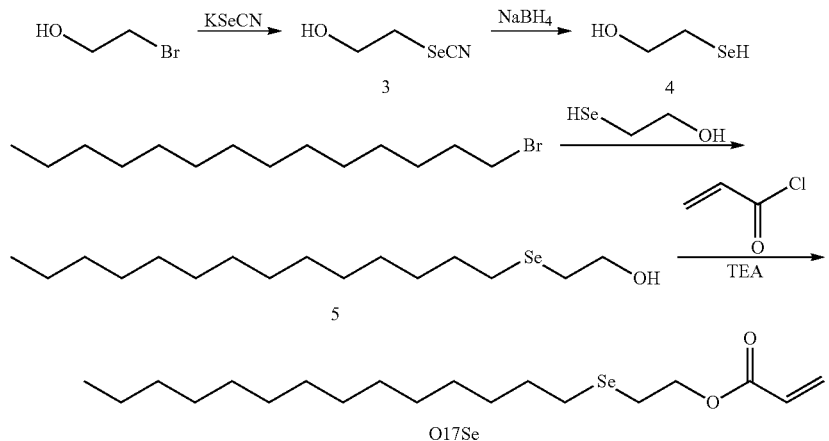

Potassium selenocyanate (1.5 g, 10 mmol) was added in portion to a solution of 2-bromoethanol (1.6 g, 13 mmol) in acetone (50 mL) at room temperature. The solution was heated to reflux for 2 h. After cooling to room temperature, the white precipitate was filtering off and acetone was removed by rotary evaporation under vacuum. Compound 3 was then dissolved in ethanol (25 mL) and sodium borohydride (0.9 g, 24 mmol) was added slowly at 0° C. After the reaction solution turned to colorless, 1-bromotetradecane (4.1 g, 15 mmol) was added through a dropping funnel. The reaction was stopped by adding DI water (10 mL) after 30 min. Then the ethanol was removed under reduced pressure, reaction mixture was diluted with saturated sodium chloride aqueous solution (50 mL), and extracted with DCM (3×50 mL). Compound 5 (1.5 g, yield about 46%) was obtained after column chromatography purification on silica gel using n-hexane/ethyl acetate as elute. In a manner similar to that for the preparation of O17O and O17S, O17Se was obtained as oil-like liquid (2.7 g, yield about 72%). The structure of O17Se was confirmed by $^1$H NMR spectrum recorded in CDCl$_3$.

Lipidoids Synthesis

Commercially available amine heads, e.g., Compounds 10, 17, and 63, were mixed with acrylate tails O17O, O17S, or O17Se stoichiometrically. The mixture thus obtained was stirred at 70° C. for 48 h. See FIG. 1. Lipidoids were purified by Teledyne Isco Chromatography system, characterized by $^1$H NMR and ESI-MS, and coded as amine number (X) and O17Y (R-O17Y, Y being O, S or Se) as shown in the table above. The typical $^1$H NMR and ESI-MS spectra of 76-O17O, 76-O-17S and 76-O17Se are shown in FIGS. 2a and 2b.

Lipidoid Nanoparticles Fabrication and Characterization.

Lipidoids nanoparticles (LNPs) were fabricated in sodium acetate buffer (25 mM, pH 5.2) by following the simple ultrasonication and vortex procedures described above. Hydrodynamic sizes and polydispersity index (PDI) of LNPs were measured by dynamic laser scattering (DLS) analysis. As shown in FIG. 2c, most of the O, S and Se ethers containing LNPs had the averaged hydrodynamic diameter (<$D_h$>) between 100-300 nm, and the PDI in the range 0.1-0.3, suitable for intracellular protein delivery application. Further, as also shown in FIG. 2c, it was found that about 53% of LNPs with O17O tails, about 82% of O17S LNPs, and about 65% of O17Se LNPs had <$D_h$> less than 200 nm, resulted from the effect of incorporated chalcogen atoms on the supramolecular self-assembly behaviors in aqueous solutions. Typical size distribution profiles of 76-O17O ($<D_h>$ being 170.1 nm, $\mu_2/I^2$ being 0.37), 76-O17S ($<D_h>$ being 114.3 nm, $\mu_2/I^2$ being 0.24) and 76-O17Se ($<D_h>$ being 129.4 nm, $\mu_2/I^2$ being 0.18) LNPs are shown in FIG. 2d.

Figure 2:
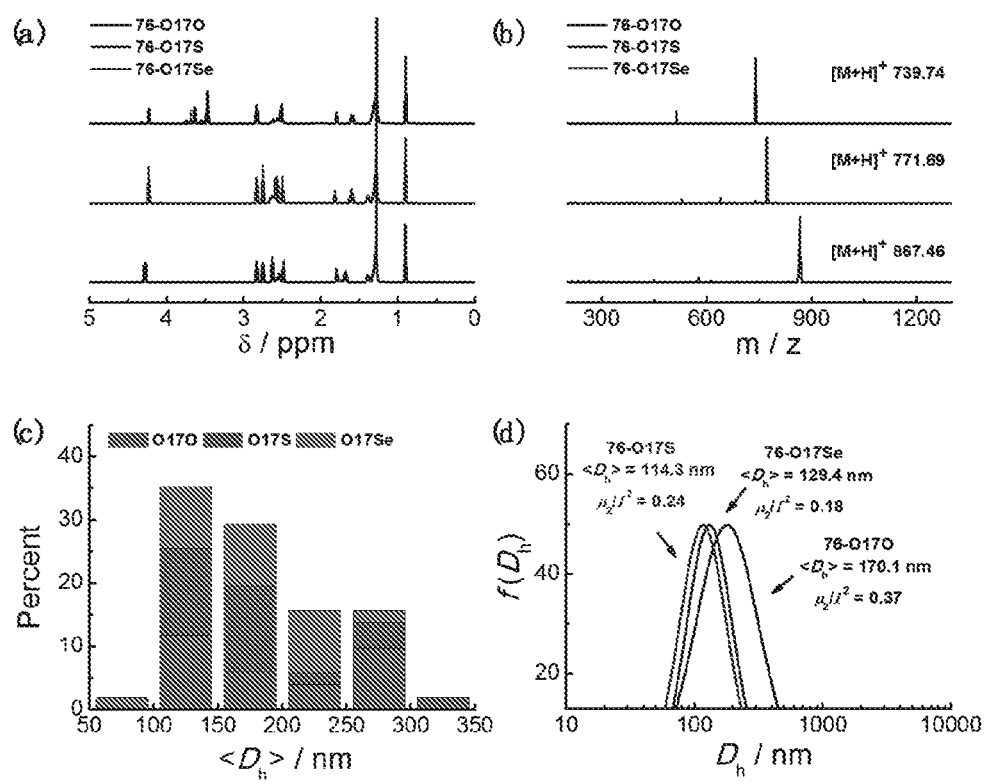
FIG. 2 is a schematic depiction of characterization of lipidoids and LNPs. (a) and (b) $^1$H NMR and ESI-MS spectra of 76-O17O, 76-O17S, and 76-O17Se (see exemplary lipid-like compounds below). (c) Statistical analysis of averaged hydrodynamic diameter ($<D_h>$) distribution of LNPs. (d) Typical hydrodynamic diameter distributions of 76-O17O, 76-O17S, and 76-O17Se LNPs.
Figure 3:
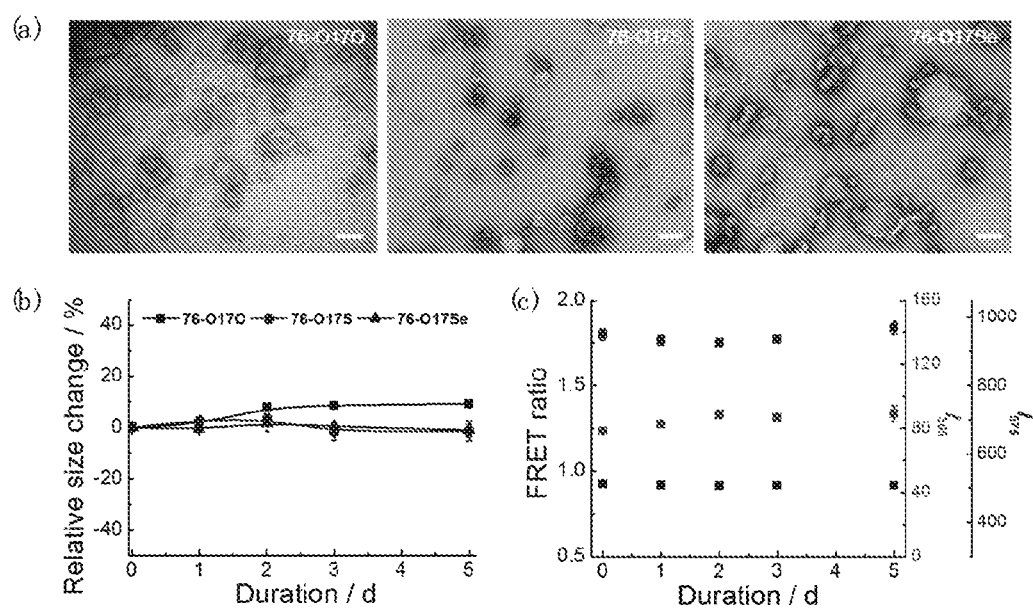
FIG. 3 is a schematic depiction of another characterization of lipidoids and LNPs. (a) and (b) Typical transmission electron microscopy (TEM) images and relative size variations of 76-O17O, 76-O17S, and 76-O17Se LNPs (scale bar being 100 nm). (c) Fluorescent emission intensities and FRET ratios of DiO/DiI loaded 76-O17Se LNPs during storage.

The morphologies of LNPs were further studied by the transmission electron microscopy (TEM). As shown in FIG. 3a, spherical particles were observed in the images of 76-O17O, 76-O17S and 76-O17Se LNPs, and the measured number-averaged sizes (145 nm, 94 nm, and 133 nm for 76-O17O, 76-O17S, and 76-O17Se, respectively) are comparable with the hydrodynamic diameters as determined by DLS. See FIG. 2d. The morphologies of other LNPs including 80-O17O, 80-O17S, and 80-O17Se, were also examined by their TEM images, which showed presence of spherical particles. Subsequently, the stability of LNPs thus prepared was examined by DLS and fluorescence measurements. As shown in FIG. 3b, the time-dependent DLS measurements revealed that no evident aggregation of the 76-O17O, 76-O17S, and 76-O17Se LNPs occurred during five days of storage under room temperature, with the relative size change being less than ±15%. Fluorescence resonance energy transfer (FRET) pair, DiO and DiI, loaded 76-O17Se LNPs also showed negligible FRET ratio ($I_{575}/(I_{575}+I_{505})$) variations in five days of storage, as shown in FIG. 3c, which indicated the structure integrity and long-term storage stability of the LNPs.

Example 2: Evaluation of LNPs for Protein Delivery

A study was performed to evaluate the effect of LNPs prepared in EXAMPLE 1 on protein delivery as follows.
In Vitro Screening of LNPs for Protein Delivery A Cre recombinase protein fused to a negatively supercharged GFP variant ((−30)GFP-Cre) was used as a model cargo protein. The (−30)GFP-Cre protein was able to complex with cationic LNPs through electrostatic attraction and other types supramolecular interactions. The cellular uptake of LNPs could be determined by direct analysis of intracellular GFP fluorescent intensity as reported in Wang. HeLa-DsRed cells were used in this study, which expressed red fluorescent DsRed upon Cre-mediated recombination to facilitate the functional study of delivered proteins in the following study.

Figure 4:
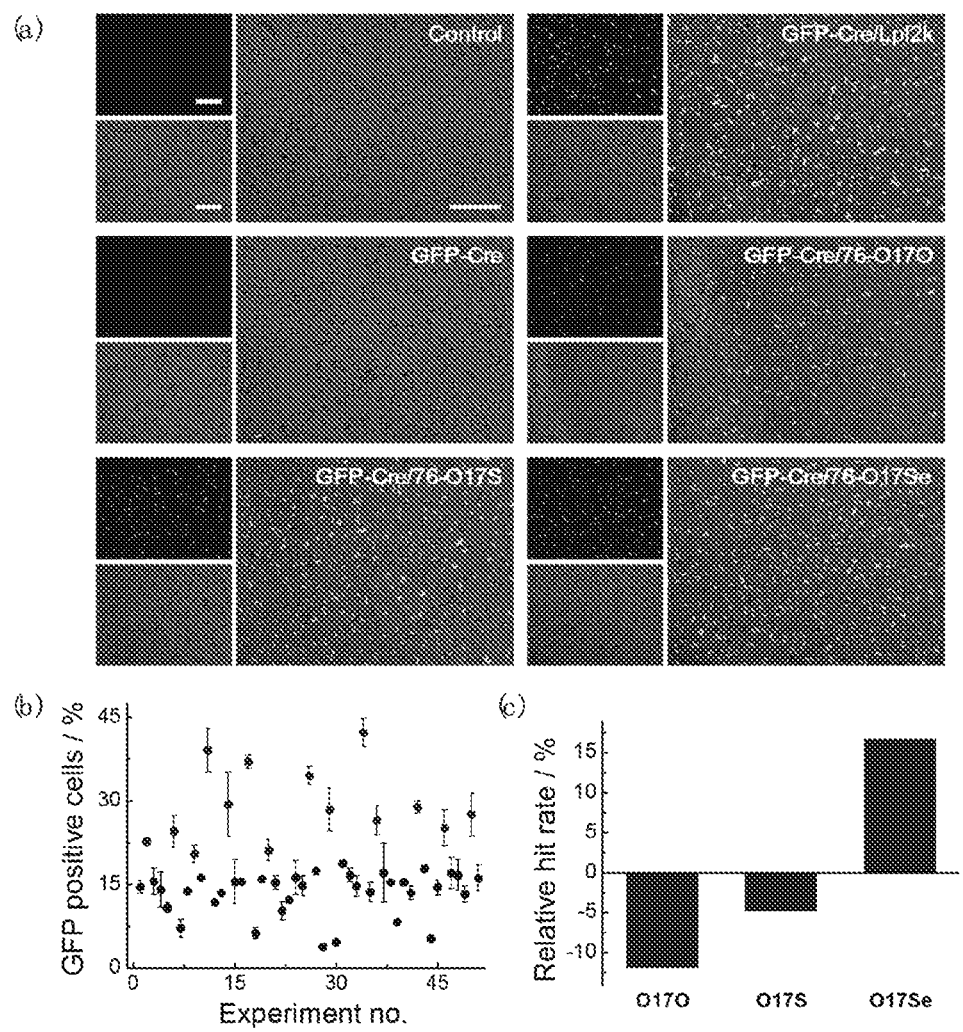
FIG. 4 is a schematic depiction of in vitro screening of LNPs for protein delivery. (a) Typical images of (−30)GFP-Cre protein and (−30)GFP-Cre loaded 76-O17O, 76-O17S, and 76-O17Se LNPs treated HeLa-DsRed cells. Scale bar=200 μm. (b) Percentage of GFP-positive cells shown for 51 LNPs tested. Data points marked in red for LNPs induced high level of transfection. (c) The tails (O17O, O17S, and O17Se) influenced (−30)GFP-Cre protein transfection activity.

The (−30)GFP-Cre protein loaded LNPs (GFP-Cre/LNPs) were prepared at first by simply mixing precalculated amount of aqueous solution of LNPs and protein at ambient conditions. For the intracellular delivery, after incubation with GFP-Cre/LNPs nanoparticles for 6 h, the GFP-positive cells were observed using fluorescence microscopy, harvested and counted by flow cytometry. As shown in FIG. 4a, comparing with the control group, i.e., untreated HeLa-DsRed cell, bright green fluorescence emission was observed from the GFP-Cre/Lpf2k (Lpf2k being Lipofectamine 2000, a commercial transfection agent), GFP-Cre/76-O17O, GFP-Cre/76-O17S, and GFP-Cre/76-O17Se treated cells. Cells treated with the naked protein, (−30)GFP-Cre, however, showed negligible fluorescence emission, as compared with lipid-facilitated delivery systems, which indicated that the naked (−30)GFP-Cre protein could not efficiently enter into the HeLa-DsRed cells. The intracellular (−30)GFP-Cre protein delivery efficiencies were further quantified by flow cytometry. As shown in FIG. 4b, both the naked (−30)GFP-Cre protein and the control group showed low portions of GFP-positive cells, consistent with the results of fluorescence microscopy shown in FIG. 4a.

On the other hand, in the presence of LNPs, the proportions of GFP-positive cells were increased, located in the range of 4-42%, with most of them being around 12-18%. Delivery efficiencies of LNPs were comparable with that of Lpf2k (about 31% of GFP-positive cells). For instance, the proportions of GFP-positive cells treated with (−30)GFP-Cre protein loaded 400-O17Se, 80-O17Se, and 77-O17Se LNPs were found to be 42%, 39% and 37%, respectively.
Investigation of Structure-Activity Relationship.

The library of 51 O, S and Se ether-containing lipidoids thus prepared was utilized to study the structure-activity relationship between LNPs and intracellular protein delivery efficacies.

More specifically, lipidoids with greater than 20% GFP-positive cells treated with (−30)GFP-Cre protein/LNP nanoparticles were defined as efficacious LNPs (red data points in FIG. 4b), as compared with the bulk LNPs (black data points). The lipidoids library was then categorized into three groups according to their hydrophobic tail structures (O17O, O17S, and O17Se); each tail made up 33.3% of the library. In the efficacious LNPs group, 21.4%, 28.6%, and 50% of lipidoids were with O17O, O17S, and O17Se tails respectively. Therefore, the relative hit rates of LNPs with O17O, O17S, and O17Se tails were −11.9%, −4.7%, and 16.7%, respectively, relative to the initial library (FIG. 4c). In other words, lipidoids with O17O and O17S tails were significantly underrepresented among LNPs with delivery efficacy greater than 20%, while lipidoids with O17Se tail was overrepresented, suggesting that O17Se tails were associated with efficacious LNPs.

It was determined that the delivery efficiencies of LNPs were related to the chemical structures of amine heads, hydrophobic tails, substitution numbers and apparent pKa values. In this study, to further elucidate the structure-activity relationship of O, S, Se ethers containing lipidoids, effects of apparent pKa value and phospholipids bilayer membrane disruption ability of the LNPs were further analyzed. Apparent pKa values were measured following the previously reported procedures using 2-(p-toluidinyl)naphthalene-6-sulphonic acid (TNS) as fluorescent probe.

Figure 5:
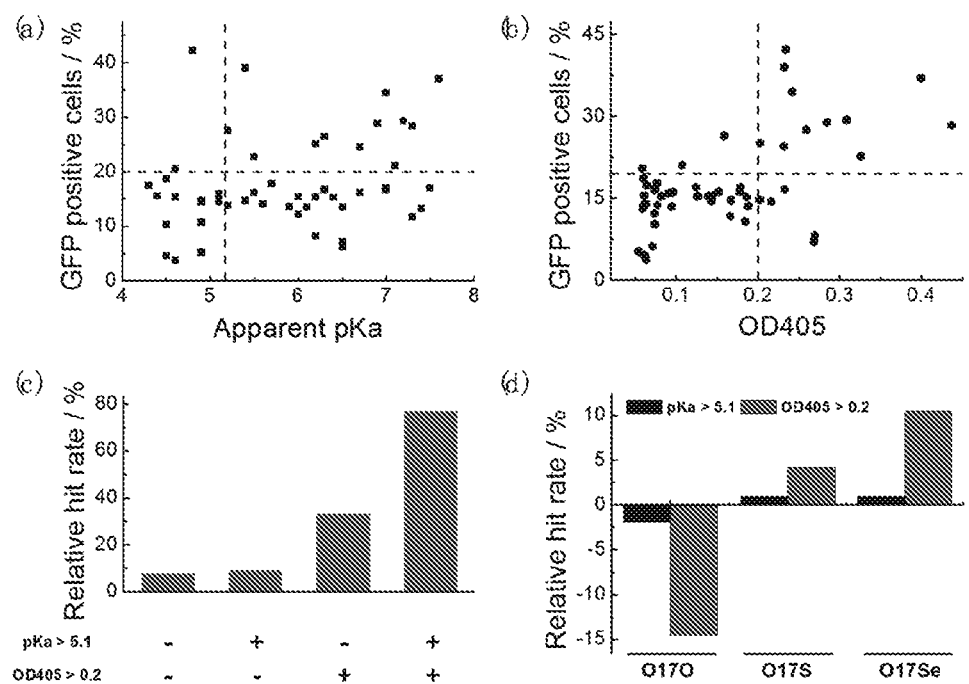
FIG. 5 is a schematic depiction of structure-activity relationship for LNPs. (a) and (b) Apparent pKa values and phospholipid bilayer membrane disruption ability influenced (−30)GFP-Cre protein delivery efficiency. (c) Relative hit rates of efficacious LNPs having none, one, or two properties. (d) Relative hit rates of efficacious LNPs having O17O, O17S, or O17Se tails.

The phospholipids bilayer membrane disruption ability of LNPs was evaluated using human red blood cells (hRBCs) as model and hemoglobin as the chromophore reporter agent. Absorbance at 405 nm (OD405) was recorded to assess the amount of released hemoglobin, using PBS buffer and Triton X-100 (1% v/v) as negative and positive controls, respectively, in which higher OD405 values indicate stronger membrane disruption capabilities. As shown in FIGS. 5a and 5b, the apparent pKa and OD405 values of LNPs were plotted against the percentages of GFP-positive cells for each LNP, and it was found that most of the efficacious nanoparticles (with GFP-positive cells greater than 20%) were located in the regions of pKa>5.1 and OD405>0.2 (gated with blue dash lines in FIGS. 5a and 5b). After further examination, it was found that these two properties have striking effects on (−30)GFP-Cre protein transfection efficiencies in HeLa-DsRed cells. As shown in FIG. 5c, when LNPs possess both of properties (i.e., pKa>5.1 and OD405>0.2), the relative hit rate to be able to mediate high transfection efficiency was 77%. When one or two of the properties was removed from the LNPs, the likelihood of achieving high transfection efficiency of (−30)GFP-Cre protein into HeLa-DsRed cells dropped significantly to 8-33%.

Furthermore, as to the structure-activity relationship, it was found that, for LNPs with O17O, O17S, and O17Se tails, the relative hit rates of above mentioned efficacy criteria were −1.9%/−14.6%, 0.99%/4.2%, and 0.99%/10.5%, respectively (pKa>5.1/OD405>0.2). See FIG. 5d. It was clear that both of the two properties were underrepresented in the group of LNPs with O17O tails, consistent with the results shown in FIG. 4c, in which O17O tail was underrepresented in the efficacious lipidoid. While both properties of high pKa and OD405 values were overrepresented in the group of LNPs with O17S and O17Se tails.

Furthermore, according to the results shown in FIGS. 5c and 5d, the membrane disruption ability of these LNPs appeared to be the more influential factor in determining in vitro (−30)GFP-Cre protein delivery efficiency into HeLa-DsRed cells, as compared with the apparent pKa values.

Example 3: (−30)GFP-Cre Protein Delivery for Gene Recombination and Cytotoxicity A study was performed to evaluate the effect of LNPs prepared in EXAMPLE 1 on (−30)GFP-Cre protein delivery for gene recombination and cytotoxicity as follows.

Figure 6:
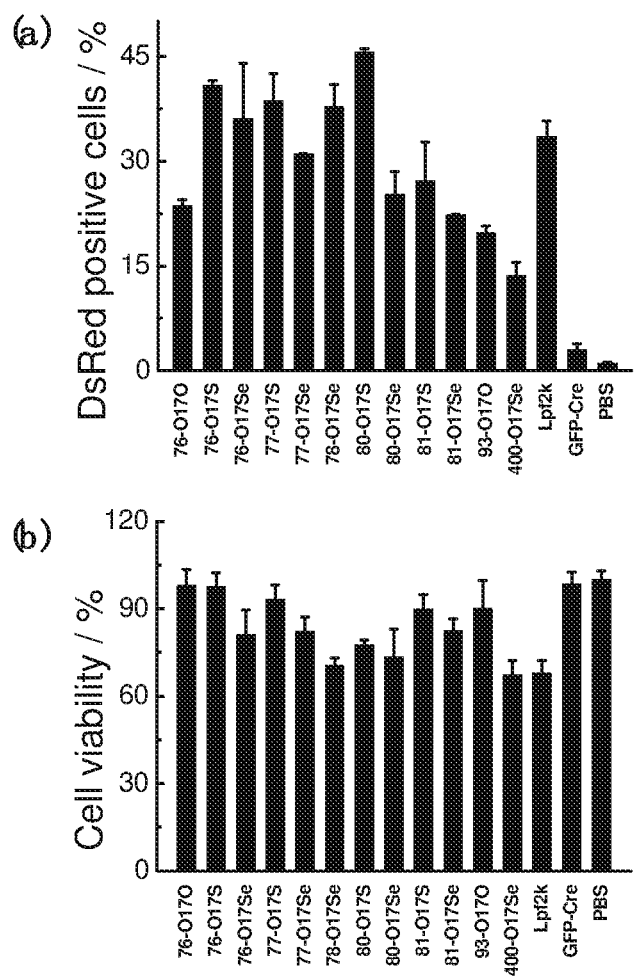
FIG. 6 shows the efficiency of (−30)GFP-Cre delivery with LNPs. (a) DsRed expression of HeLa-DsRed cells treated with (−30)GFP-Cre and (−30)GFP-Cre loaded LNPs. (b) Cell viability of HeLa-DsRed cells treated with (−30)GFP-Cre and (−30)GFP-Cre loaded LNPs

The top 12 of LNPs identified through intracellular delivery screening experiments were further tested for gene recombination using HeLa-DsRed model cells. The expression of DsRed from Cre protein mediated gene recombination was analyzed after 24 h of co-incubation with free (−30)GFP-Cre protein and protein loaded LNPs. As shown in FIG. 6a, naked (−30)GFP-Cre protein did not induce DsRed expression, due to its low internalization ability, consistent with the fluorescence microscopy observation and flow cytometry analysis demonstrated in FIG. 4a. Most of the test LNPs, on the other hand, efficiently delivered (−30)GFP-Cre protein and induced gene recombination, with 14-46% of the cells positive for DsRed.

More specifically, certain LNPs exhibited high protein transfection efficiencies, namely, 76-O17S (40.8%), 76-O17Se (36.1%), 77-O17S (38.6%), 77-O17Se (31.0%), 78-O17Se (37.8%), and 80-O17S (45.6%). These LNPs exhibited higher or similar transfection efficiencies when compared with Lpf2k (33.5%).

Through MTT assay against HeLa-DsRed cells, 76-O17S, 76-O17Se, 77-O17S, and 77-O17Se LNPs showed low cytotoxicity as greater than 80% cells were alive, as compared to Lpf2k, 400-O17Se 78-O17Se, 80-O17S, and 80-O17Se, of which the cell viability was 67-77%. See FIG. 6b.

These results indicate that 76-O17S, 76-O17Se, 77-O17S, and 77-O17Se exhibited high intracellular protein delivery and Cre-mediated genome recombination efficacies, with lower cytotoxicity than Lpf2k.

Example 4: In Vivo GFP-Cre Delivery for Gene Recombination in Ai14 Mice

A study was performed to evaluate the effect of LNPs prepared in EXAMPLE 1 on GFP-Cre delivery for gene recombination in Ai14 mice as follows.

Delivering genome editing proteins in vivo has the therapeutic potential for treating a wide range of genetic diseases. Based on the in vitro screening results, this study was conducted to evaluate the effect of the above O, S, and Se ethers containing LNPs on delivering (−30)GFP-Cre protein in vivo for Cre-mediated gene recombination.

Figure 7:
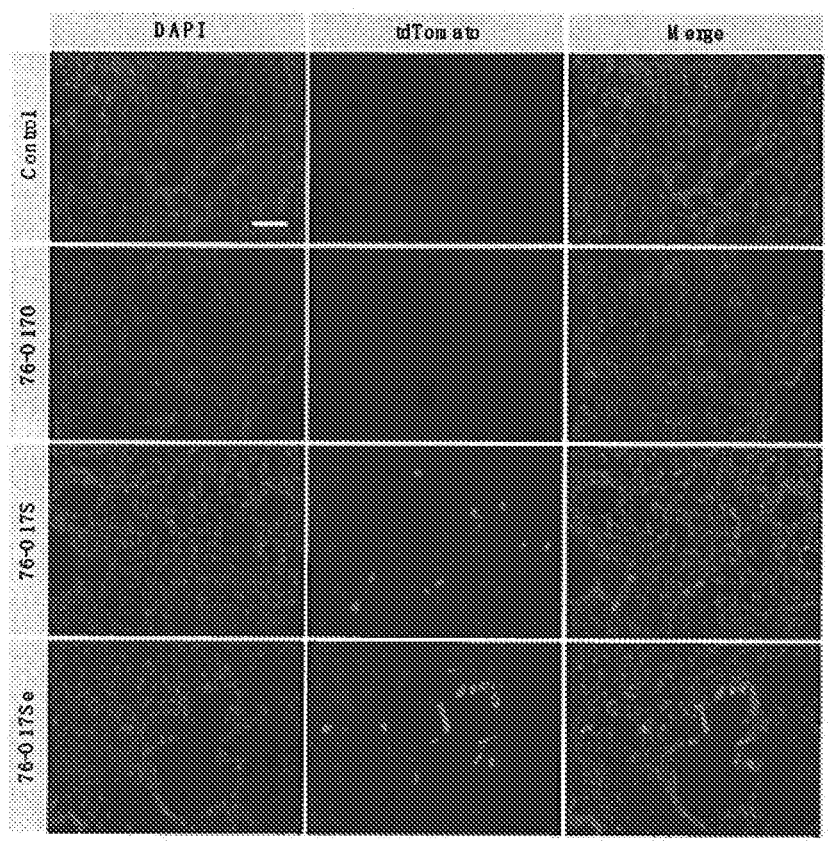
FIG. 7 is a schematic depiction of typical fluorescence images of sections of lungs obtained from Ai14 mice treated with PBS and GFP-Cre/LNPs (the first column being 4',6-diamidino-2-phenylindole or DAPI; the second column being tdTomato; the third column showing the merging of the first and second columns; and scale bar being 100 μm).

The study used an Ai14 mouse model, which had a genetically integrated loxP-flanked STOP cassette that prevents the transcription of red fluorescent protein, tdTomato. Upon Cre mediated gene recombination, the STOP cassette was removed, resulting in tdTomato expression. Considering the different performances of cargo loaded LNPs in vitro and in vivo, three LNPs with same amine heads and different tails (76-O17O, 76-O17S and 76-O17Se) were tested in this study. Formulated LNPs (lipidoid/cholesterol/DOPE/DSPE-PEG2k=16/4/1/4, weight ratio) were prepared. Mice were injected (intravenous injection) with (−30)GFP-Cre loaded the formulated LNPs (GFP-Cre/76-O17O, GFP-Cre/76-O17S, and GFP-Cre/76-O17Se) at day 0 and day 5 (100 µg of protein for each injection). Organs including heart, liver, spleen, lung, and kidney were collected at day 20 for measuring and analyzing the tdTomato expression. As shown in FIG. 7, under the same preparation and imaging conditions, strong tdTomato signals were observed in the sections of lung from GFP-Cre/76-O17S and GFP-Cre/76-O17Se injected mice. Fluorescence images with lower magnification and larger field of view were obtained. It was unexpectedly observed that the GFP/76-O17S and GFP/76-O17Se injection induced Cre-mediated genome recombination efficiently in the lung, as compared with the control group and the group treated with GFP/76-O17O. Therefore, a composition containing LNPs of this invention is useful for lung disease treatment.

Notably, both the in vitro screening results and the in vivo tests showed that lipidoids with same amine heads and different hydrophobic tails possessed very different physicochemical properties, intracellular delivery efficacies, and genome recombination profiles.

Example 5: Delivery of Cas9:sgRNA RNP for Genome Modification

A study was performed to evaluate the effect of LNPs prepared in EXAMPLE 1 on the delivery of Cas9:sgRNA RNP for genome modification as follows.

Figure 8:
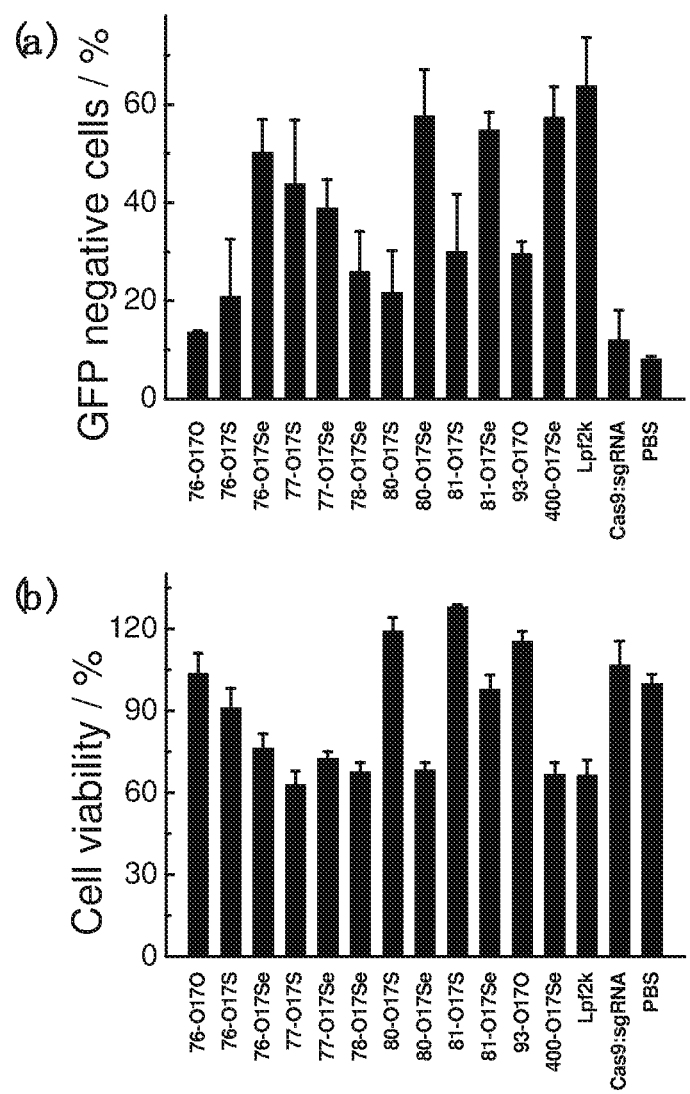
FIG. 8 shows the efficiency of Cas9:sgRNA delivery with LNPs. (a) GFP knockout of GFP-HEK cells treated with Cas9:sgRNA and Cas9:sgRNA/LNPs. (b) Cell viability of GFP-HEK cells treated with Cas9:sgRNA and Cas9:sgRNA/LNPs.
Figure 9:
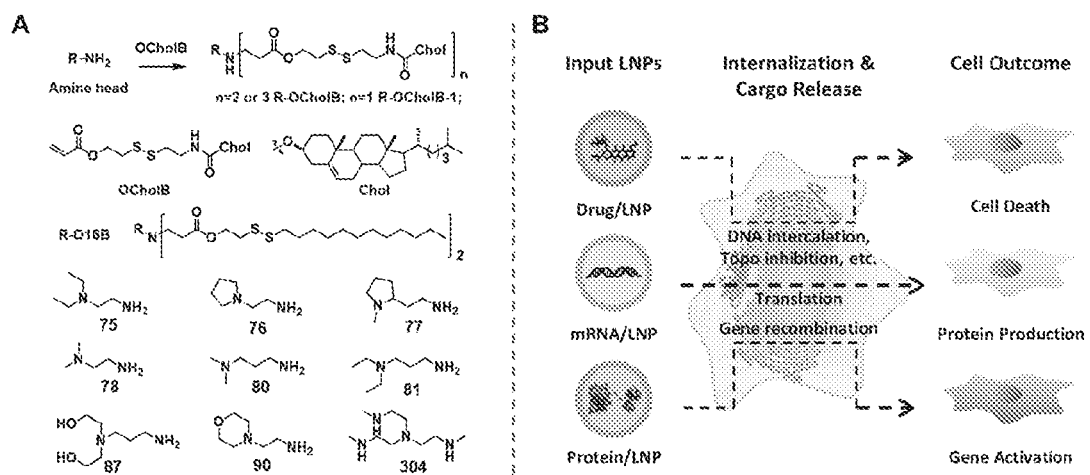
FIG. 9 is a schematic presentation of cholesterol-based and reduction-responsive combinatorial lipidoids for intracellular delivery. (A) Chemical structures of cationic lipidoids and amine head groups. (B) Lipidoids nanoparticles as a versatile platform for anticancer drugs, mRNA and protein delivery.

The Cas9:sgRNA RNP targeting genomic GFP reporter gene and GFP-HEK cells were used in this study. The morphologies of Cas9:sgRNA loaded LNPs were examined by TEM, and typical image of Cas9:sgRNA loaded 76-O17Se LNP (Cas9:sgRNA/76-O17Se) was obtained. For the intracellular delivery, GFP-HEK cells were harvested after treating with Cas9:sgRNA/LNPs nanocomplexes for 48 h. GFP gene knockout efficacy was further evaluated by flow cytometry. As shown in FIG. 8a, naked Cas9:sgRNA RNP did not induce GFP gene knockout, while the knockout efficiency of Cas9:sgRNA/Lpf2k was relatively high, with 63% of GFP-negative cells. When using O, S, and Se the-containing LNPs as delivery vehicles, the GFP-HEK cells showed a loss of 14%-58% GFP expression. In particular, 50.2%, 57.7%, 54.7% and 57.4% of GFP knockout were observed when cells were treated with Cas9:sgRNA loaded with 76-O17Se, 80-O17Se, 81-O17Se, and 400-O17Se LNPs. These lipidoids could efficiently deliver genome editing proteins into different mammalian cell lines in vitro, based on the results of gene recombination of Cre protein in HeLa-DsRed cells and GFP gene knockout of Cas9:sgRNA RNP delivery in GFP-HEK cells.

In vitro cytotoxicity of Cas9:sgRNA/LNPs against GFP-HEK cells was also evaluated by the MTT assay. As shown in FIG. 8b, the cell viabilities were determined to be 67%-119% after incubation with Cas9:sgRNA/LNPs at 37° C. for 48 h, indicating that the certain LNPs were non-cytotoxic to GFP-HEK cells, while some showing cell viability the same as that of Lpf2k (cell viability about 66%) under the same experimental conditions. It was also observed that two LNPs with high Cas9:sgRNA delivery efficiencies, i.e. 80-O17Se and 400-O17Se, exhibited cell viability similar to that for Lpf2k, namely, 68.2% and 66.7% of cell viability for 80-O17Se and 400-O17Se, respectively. Unexpectedly, 76-O17Se and 81-O17Se LNPs showed both high Cas9:sgRNA transfection efficiency (50.2% and 54.7%) and low cytotoxicity (76.3% and 97.7% of cell viability after 48 h of incubation).

These results indicate that LNPs formed from lipid-like compounds of formula (I) exhibited high protein transfection efficiency and low cytotoxicity.

Methods and Materials

Preparation of Blank and Cargo-Loaded Lipidoid Nanoparticles

Lipidoids were fabricated into nanoparticles for all delivery applications. Briefly, lipidoids were mixed with sodium acetate buffer (25 mM, pH 5.2), sonicated for 30 min in an ultrasonic bath, followed by another 30 min of vigorous vortexing. The as-prepared blank LNPs were stored at 4° C. For Cy5-RNA/LNP, mRNA/LNP and protein/LNP complexation, blank lipidoid nanoparticles were mixed with RNA molecules or (−30)GFP-Cre protein in PBS buffer (pH 7.4) following our previously reported procedures and incubated at room temperature for another 30 min before use. Typical procedures for Nile red encapsulation are as follows: 5 μL of Nile red stock solution in acetone was added into an empty vial, which was then placed in a vacuum oven to completely remove the organic solvent. Then, a predetermined amount of blank LNP stock solution (1.0 mg/mL) was added into the vial. The mixture was sonicated for 40 min in an ultrasonic bath and stirred overnight at room temperature. The final concentration of Nile red was adjusted to $6.6 \times 10^{-7}$ mol $L^{-1}$ and $6 \times 10^{-7}$ mol $L^{-1}$ for thiol triggered release study and cell incubation, respectively, by diluting with PBS as necessary. Typical procedures for CPT and DiO/DiI FRET pair encapsulation are as follows: 100 μL of DiO/DiI stock solution in MeOH was charged into an empty vial and placed in a vacuum oven to remove the organic solvent. Lipidoids (2.0 mg) in 200 μL of methanol were then added into the vial and stirred to produce a homogeneous solution. Then, 600 μL of DI water was added dropwise in 10 min with continuous stirring. The resulting mixture was dialyzed against DI water for 24 h (Thermo Scientific Slide-A-Lyzer Dialysis Cassette, MWCO=3500 Da), and fresh water was replaced every 4 h. Typical procedures for encapsulation of calcein and doxonorubicin hydrochloride are as follows: precalculated amounts of calcein or Dox stock solutions in DI water was diluted into 800 μL with sodium acetate buffer, and used as the selective solvents to trigger the self-assembly process of lipidoids in methanol (5 mg/mL), respectively. The unloaded calcein or Dox was removed by dialysis against DI water (Thermo Scientific Slide-A-Lyzer Dialysis Cassette, MWCO=3500 Da).

Intracellular Delivery of Cargo-Loaded Lipidoid Nanoparticles

For the intracellular uptake study, HeLa or HeLa-DsRed cells were seeded in 48-well plate with an initial seeding density of $2 \times 10^4$ cell/well. After 24 h of incubation at 37° C., 5% $CO_2$, NR or (−30)GFP-Cre loaded nanoparticles were added to the cells and incubated for certain time (1-8 h) before fluorescence microscopy (BZ-X Analyzer) observation and flow cytometry (BD FACS Calibur, BD Science, CA) analysis (red fluorescence emission from NR and green fluorescence emission from GFP). The final concentration of NR is $6 \times 10^{-7}$ mol $L^{-1}$. The final concentration of (−30) GFP-Cre protein concentration is $25\text{-}100 \times 10^{-9}$ mol $L^{-1}$. For small molecular anticancer drugs delivery, HeLa cells were seeded in 96-well plate with an initial seeding density of $5 \times 10^3$ cell/well. After 24 h of incubation at 37° C., 5% $CO_2$, Dox, CPT or Oxa loaded nanoparticles were added to the cells and incubated for 8 h followed by media change. The cells were then incubated for another 40 h before cell viability analysis. For mRNA delivery, HeLa, B16F10, HEK 293, NIH 3T3 or Jurkat cells were seeded in 48-well plate with an initial seeding density of $2 \times 10^4$ cell/well. After 24 h of incubation at 37° C., 5% $CO_2$, mRNA loaded nanoparticles were added to the cells and incubated for another 24 h before fluorescence microscopy and flow cytometry analysis. For protein delivery, HeLa-DsRed cells were seeded in 48-well plate with an initial seeding density of $2 \times 10^4$ cell/well. After 24 h of incubation at 37° C., 5% $CO_2$, (−30)GFP-Cre protein loaded nanoparticles were added to the cells and incubated for 8 h followed by a complete media change. The cells were then incubated for another 16 h (24 h of incubation in total) before fluorescence microscopy and flow cytometry analysis.

In Vitro and In Vivo Toxicity Assay

Cell viabilities of HeLa and HeLa-DsRed were measured using the standard MTT assay. In a 96-well plate, after incubating HeLa or HeLa-DsRed cells with blank or cargo-loaded nanoparticles, the MTT reagent (5 mg/mL, in 30 μL PBS buffer) was added and the cells were incubated for another 4 h at 37° C. The cell culture media was then carefully removed and 200 μL of DMSO was added to each well. The DMSO solution was then transferred into a clean 96-well plate and the absorbance at 570 nm was recorded by a microplate reader. All experiments were performed in quadruplicate.

For in vivo toxicity studies, the body weights of untreated and nanoparticles injected Balb/c mice (housed in a temperature and humidity controlled facility with a 12 h light/dark cycle) were measured at day 1, 3, 5, 7, 9, 11, 13 and 14. Biological functions of kidney and liver were examined by the serum biochemical tests and concentrations of creatinine, urea, aspartate aminotransferase (AST), and alanine aminotransferase (ALT) were measured using corresponding detection kits (MilliporeSigma) following manufacturers' protocols.

In Vivo Protein and mRNA Delivery to Ai14 Mouse

Similar to the in vitro transfection study, lipidoid nanoparticles were prepared for mRNA or protein loading and in vivo delivery. Ai14 mice were housed in a temperature and humidity controlled facility with a 12 h light/dark cycle. Three mice in each group were injected (intravenously or intramuscularly) with Cre mRNA-loaded or (−30)GFP-Cre protein-loaded LNPs formulations. Organs including heart, liver, spleen, lung and kidney from all groups were collected at day 10 (intramuscular injection) or 14 (intravenous injection) after injection. The tissues were fixed overnight in 4% paraformaldehyde (PFA) and dehydrated in 30% sucrose before being froze in in OCT and sectioned into 10-15 μm slices. The slices were then collected and stained with DAPI for fluorescence imaging (BZ-X Analyzer fluorescence microscopy).

Example 6: Cholesteryl Lipidoid Synthesis, Nanoparticles Fabrication and Characterization

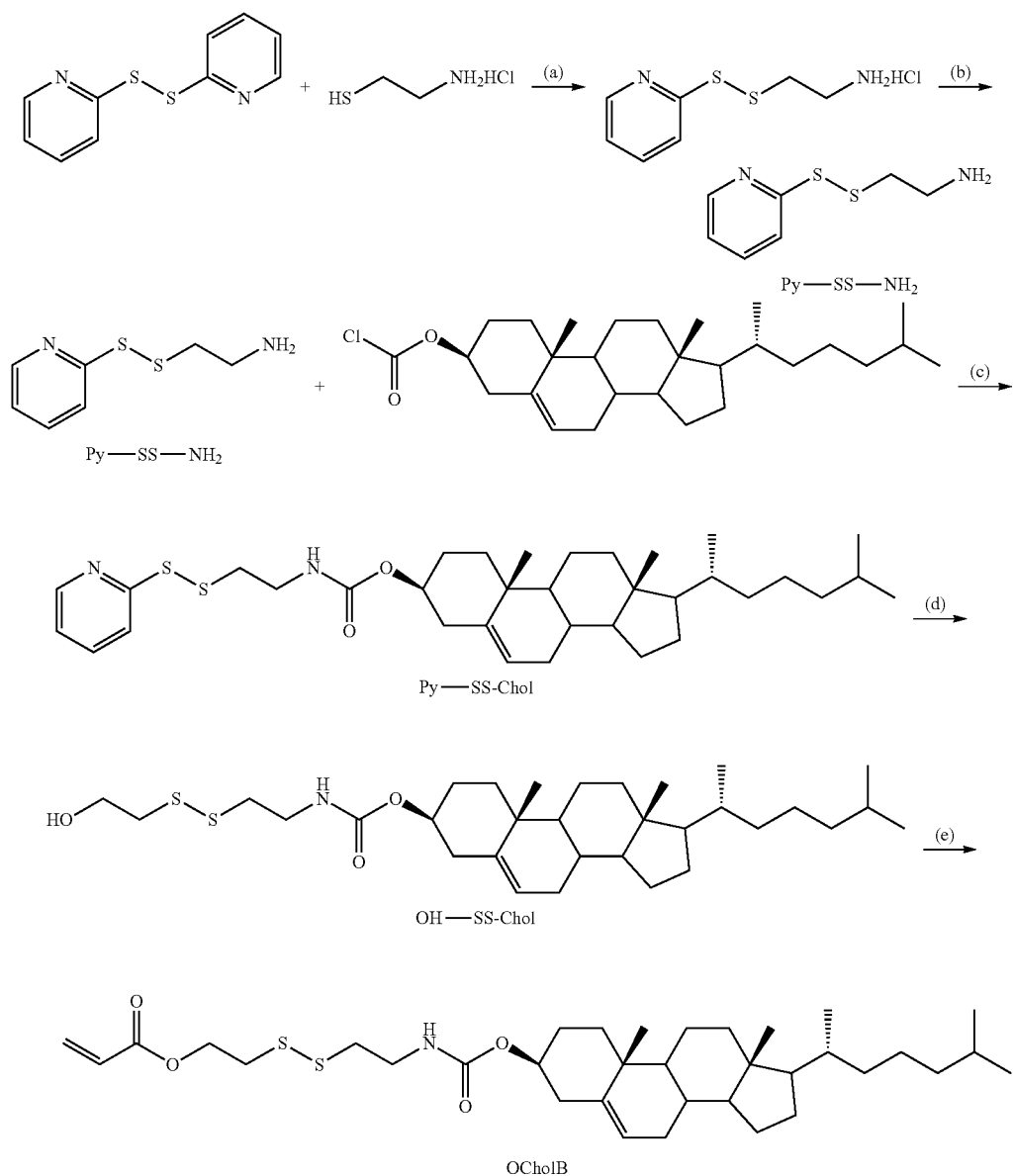

Synthesis of Py-SS-Chol

Cholesteryl chloroformate (10.71 g, 23.85 mmol) was dissolved in anhydrous DCM (50 mL) and added into the DCM solution of Py-SS-NH2 (4.47 g, 23.99 mmol) and TEA (3.71 g, 36.69 mmol) dropwise at 0° C. The reaction mixture was stirred overnight and Py-SS-Chol was obtained as slightly yellow viscous solid (4.89 g, yield ~34.26%) after silica gel column chromatography purification using ethyl acetate, dichloromethane and n-hexane as the mobile phase.

Synthesis of OH-SS-Chol

Py-SS-Chol (3.55 g, 5.93 mmol) and acetic acid (600 μL) were dissolved in DCM (100 mL). 2-Mecaptoethanol (0.51 g, 6.52 mmol) was then added dropwise, and the reaction mixture was maintained at 35° C. for another 24 h with continuous stirring. OH-SS-Chol was purified by silica gel column chromatography using ethyl acetate and n-hexane as mobile phase and a colorless solid was obtained (2.74 g, yield ~81.63%).

Synthesis of OCholB

OH-SS-Chol (2.41 g, 4.26 mmol) and TEA (0.65 g, 6.39 mmol) were dissolved in anhydrous DCM (100 mL). Acryloyl chloride (0.46 g, 5.11 mmol) was added dropwise at 0° C. The reaction mixture was stirred overnight and OCholB was obtained as a colorless solid (2.52 g, yield ~95.68%) after silica gel column chromatography purification using ethyl acetate, dichloromethane and n-hexane as mobile phase.

Synthesis of Lipidoids

The cholesterol-containing acrylates tails shown above were reacted with head amines $R_a$—$NH_2$ (i.e., Compounds 75-78, 80, 81, 87, 90, and 304.) to afford the following lipid-like compounds:

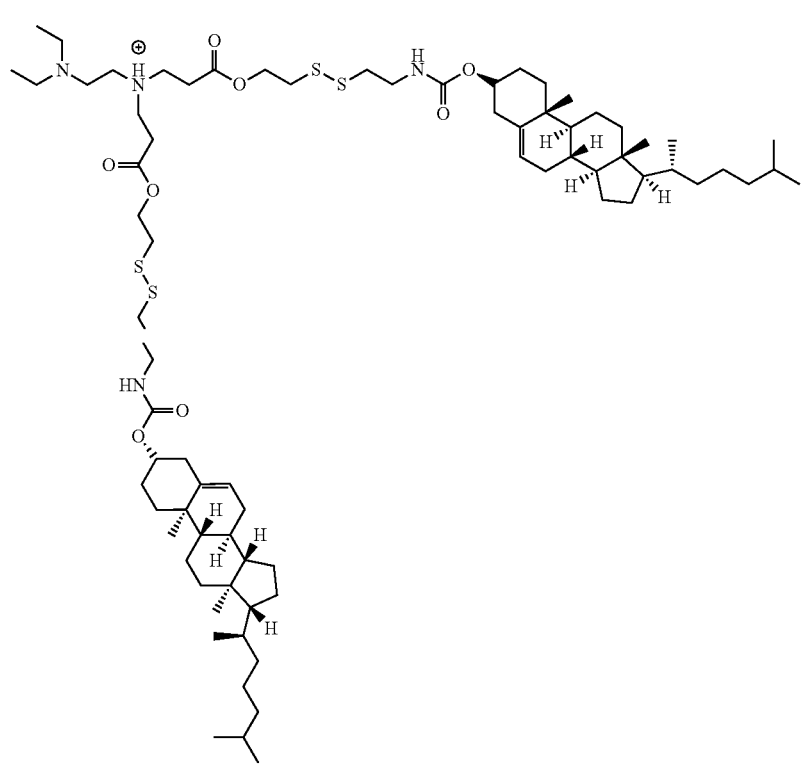
75-chol
Molecular Weight: 1357.13
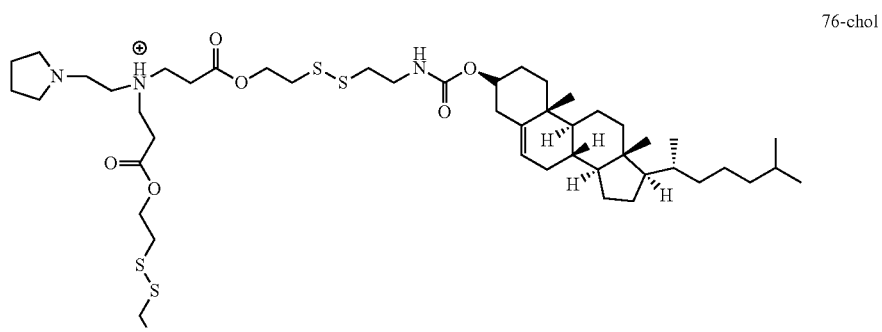
76-chol
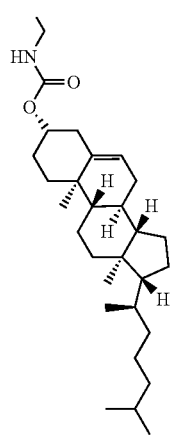
Molecular Weight: 1355.12

-continued
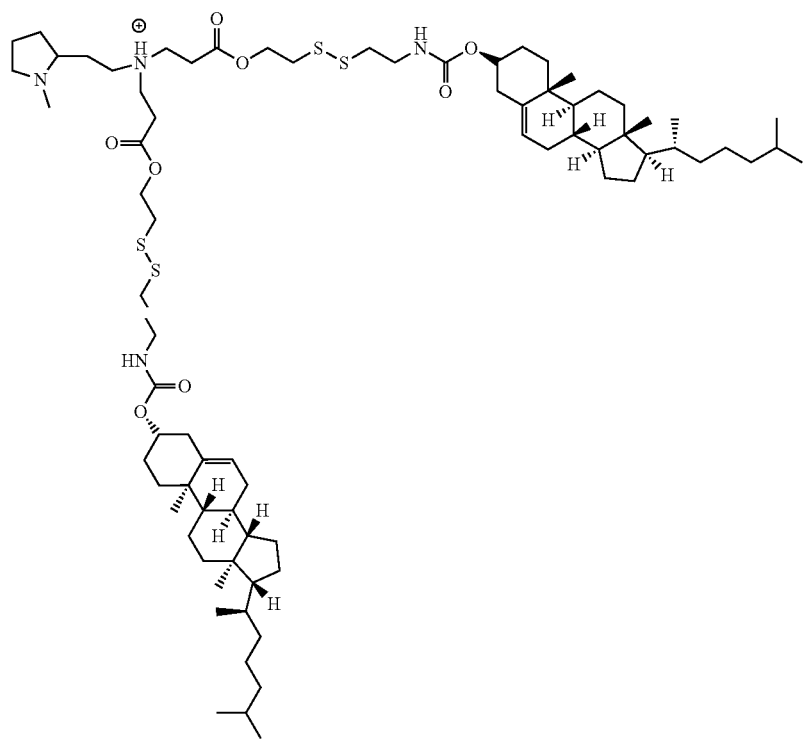
77-chol
Molecular Weight: 1369.15
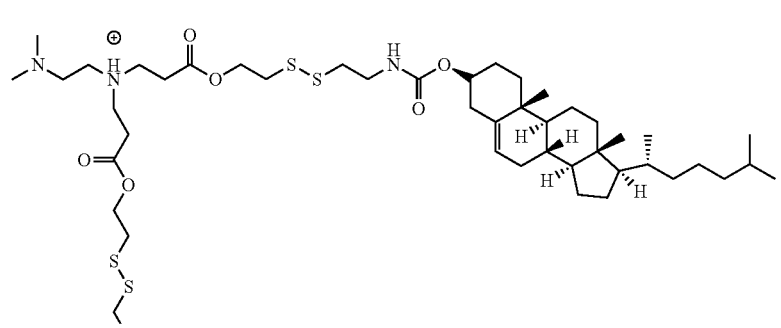
78-chol
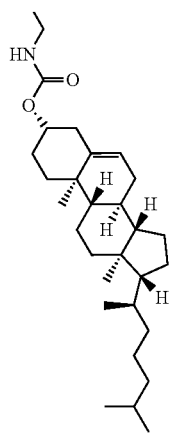
Molecular Weight: 1329.08

80-chol
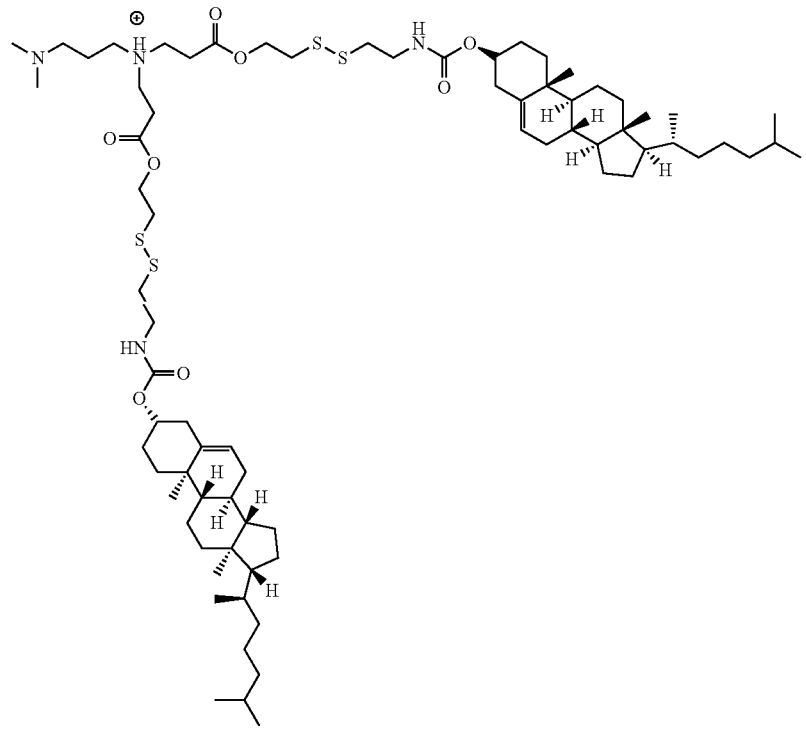
Molecular Weight: 1343.11
81-chol
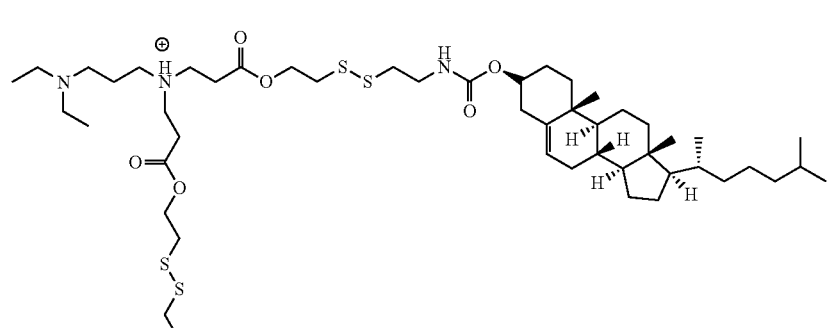
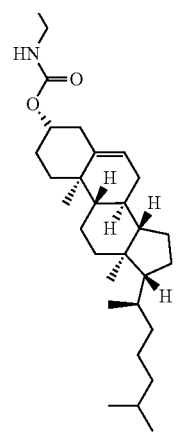
Molecular Weight: 1371.16

87-chol
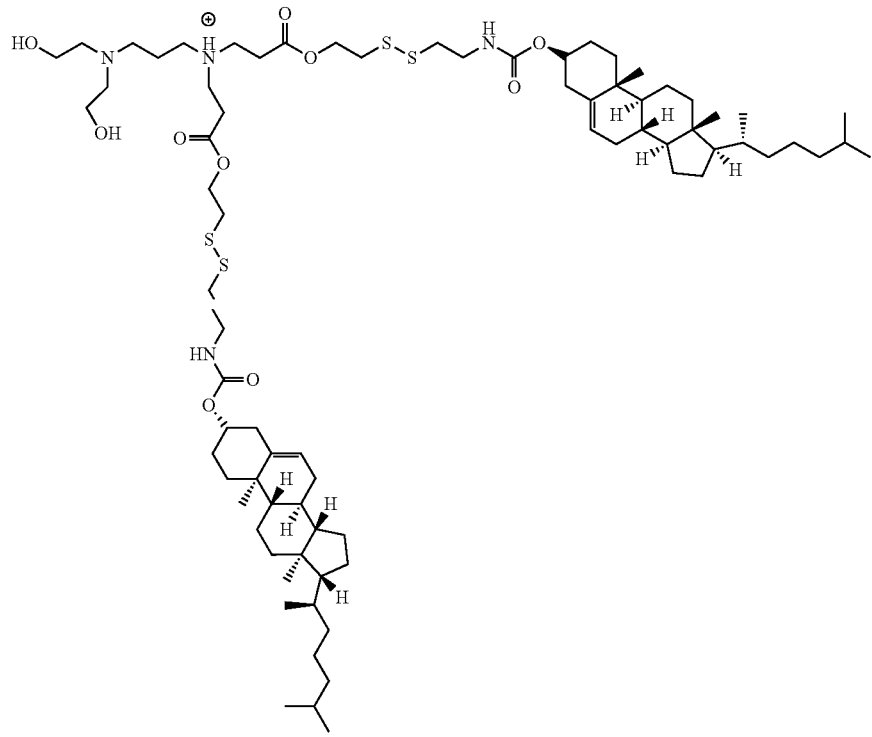
Molecular Weight: 1403.16
90-chol
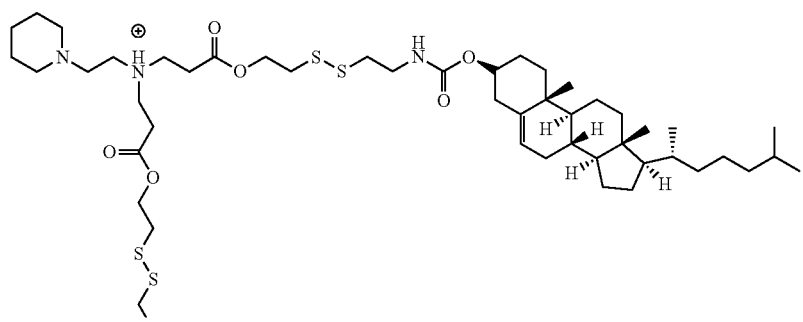
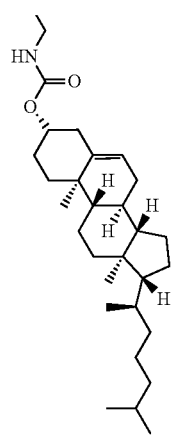
Molecular Weight: 1371.12

-continued

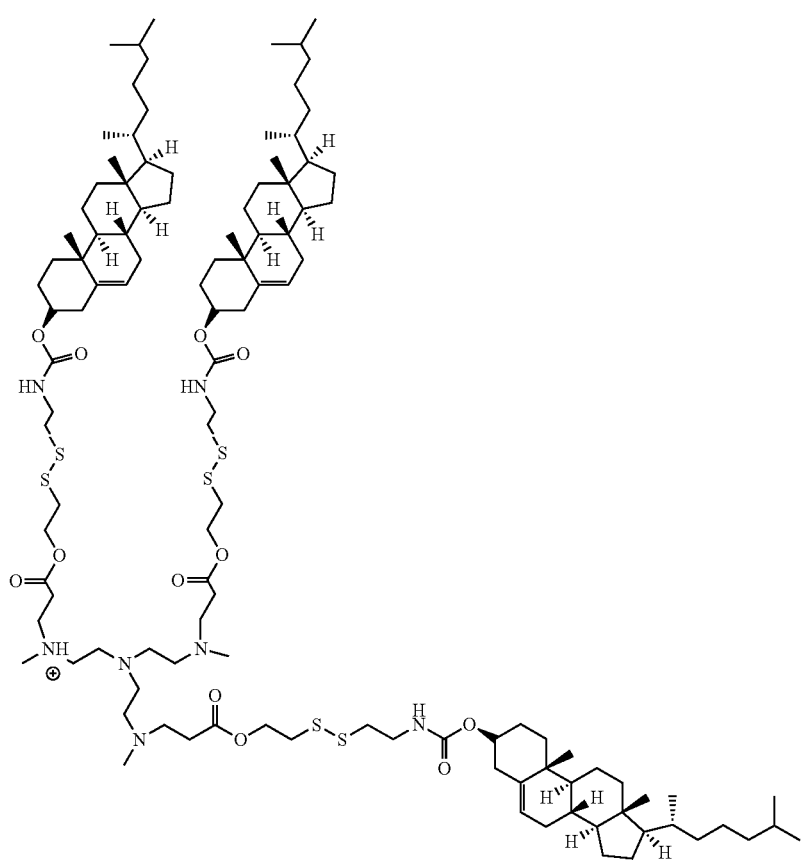

304-chol

Molecular Weight: 2049.21

Preparation of Blank and Cargo-Loaded Lipidoid Nanoparticles

Figure 10:
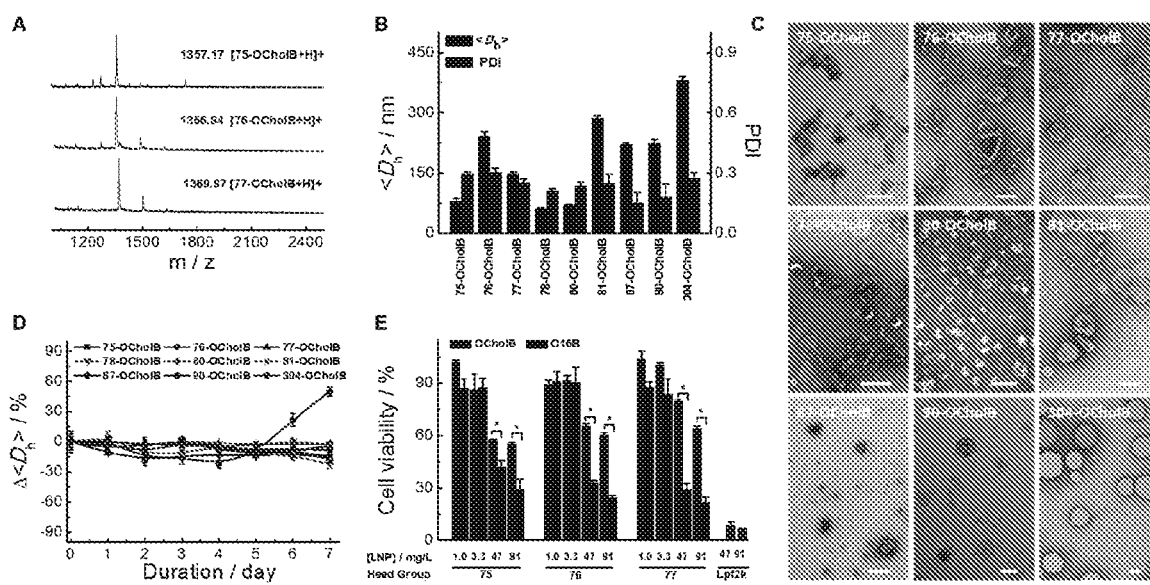
FIG. 10 shows the characterization of lipidoids and nanoparticles. (A) MALDI-TOF spectra of lipidoids. (B) Hydrodynamic diameter and polydispersity of lipidoid nanoparticles measured by DLS. (C) TEM images of lipidoid nanoparticles. Scal bar=200 nm. (D) Relative size change of blank nanoparticles under storage. (E) Cytotoxicity tests of OcholB, O16B and Lpf2k nanoparticles. P<0.05, student's t-test.

Lipidoids were fabricated into nanoparticles for all delivery applications. As shown in FIG. 10B, most nanoparticles showed average diameters in the range of 70-300 nm and PDI 0.1-0.3. The sizes of LNPs self-assembled from lipidoids with OCholB tails are similar to our previously reported LNP libraries with alkyl chains. The relative low PDI values indicated the uniformity of these nanoparticles.

The morphologies of OCholB fully substituted LNPs were then examined by transmission electron microscopy (TEM). As shown in FIG. 10C, spherical vesicle-like structures, which are hollow spheres with hydrophobic bilayer walls sandwiched by hydrophilic internal and external coronas, were observed from 75-OCholB, 76-OCholB, 77-OCholB, 78-OCholB, 80-OCholB, 81-OCholB, and 304-OCholB. In contrast, the vesicular structures were not well-formed for 87-OCholB and 90-OCholB compared to their counterparts, and amorphous aggregates were observed instead. TEM imaging revealed the largest particles to be 81-OCholB (216.9 nm) and 304-OCholB (394.0 nm), which is consistent with the DLS measurement results as shown in FIG. 10B.

The cytotoxicity of OCholB fully substituted LNPs (75-OCholB, 76-OCholB and 77-OCholB) and O16B LNPs (75-O16B, 76-O16B and 77-O16B) were tested side-by-side under different conditions, i.e., low dosage/short exposure time and higher dosage/long exposure time, against HeLa cell line using the standard MTT assay. As shown in FIG. 10E, at the low dosage/short exposure time conditions (i.e., [lipidoid]=1.0 or 3.3 μg mL$^{-1}$, exposure time=8 h), all the OCholB and O16B LNPs showed negligible cytotoxicity, with cell viability of >83% reported for all lipidoids (e.g. when [lipidoid]=3.3 μg mL$^{-1}$, the viabilities of 75-OCholB and 75-O16B treated cells are 86.5% and 87.7%, respectively). When the dosage and exposure duration were both increased (i.e., [lipidoid]=47 or 91 μg mL$^{-1}$, exposure time=24 h), OCholB fully substituted LNPs treated cells showed significantly higher viabilities comparing to those treated with O16B LNPs (when [lipidoid]=47 μg mL$^{-1}$, the cell viabilities are 75-OCholB/75-O16B=57.4%/41.9%, 76-OCholB/76-O16B=65.5%/32.8%, 77-OCholB/77-O16B=79.6%/29.0%; when [lipidoid]=91 μg mL$^{-1}$, the cell viabilities are 75-OCholB/75-O16B=55.1%/29.5%, 76-OCholB/76-O16B=60.2%/24.3%, 77-OCholB/77-O16B=64.1%/21.9%). These results show that the cholesteryl lipidoids have lower cytotoxicity comparing with the lipidoids with the linear alky chain. Furthermore, we compared the biocompatibility of our newly developed OCholB LNPs against that of the commercially available and widely used cationic transfection agent, lipofectamine 2000 (Lpf2k). Lpf2k is shown to be highly efficient for both protein and nucleic acids delivery; however its cytotoxicity is often a major concern, especially when the targeted cells are exposed to a relative high dosage and long incubation duration. As shown in FIG. 10E, when the HeLa cells were treated with 47 and 91 μg mL$^{-1}$ of Lpf2k for 24 h, their viabilities were determined to be 8.9% and 6.8%, which are much lower than that of OCholB LNPs treated cells under the same conditions. Above all, the in vitro cytotoxicity tests demonstrated the excellent biocompatibility of the newly developed cholesteryl-containing (OCholB) LNPs.

Figure 11:
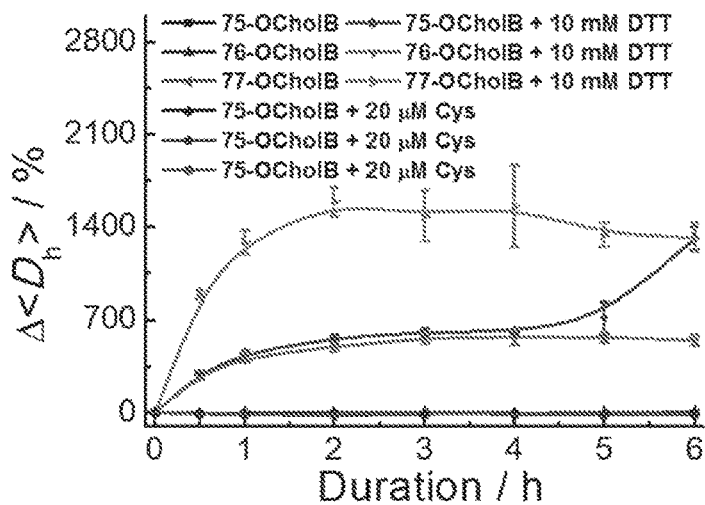
FIG. 11 shows the thiol-triggered morphological variation and cargo release. (A) Time-dependent relative size variation of the lipidoid nanoparticles with DTT and Cysteine treatment. (B) TEM images of lipidoid nanoparticles treated with DTT. Scale bar=600 nm. (C) Relative size change of lipidoid nanoparticle after 24 h of DTT treatment. (D) Fluorescent emission spectra of cargoes loaded nanoparticles. (E) Time-dependent NR release profile. (F) Fluorescent intensity of calcein encapsulated lipidoid nanoparticles treated with DTT or Cysteine. (G) RNA binding test of lipidoid nanoparticles with and without DTT treatment.
Figure 11:
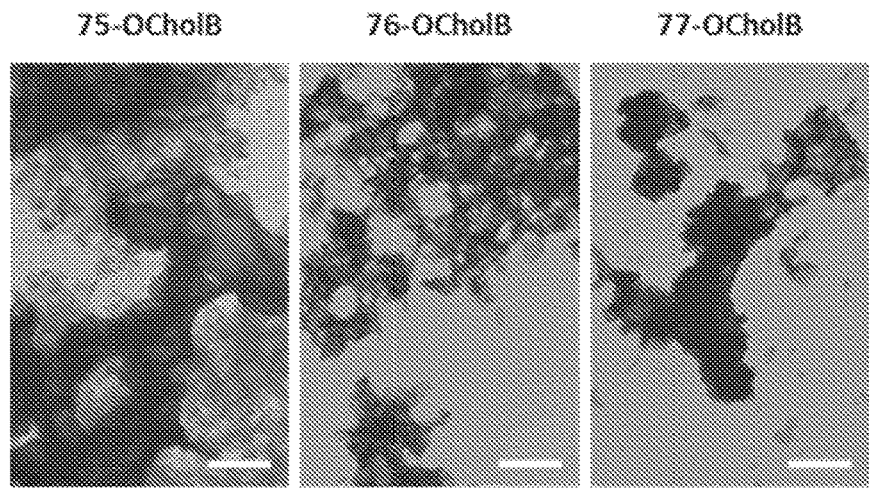
Figure 11:
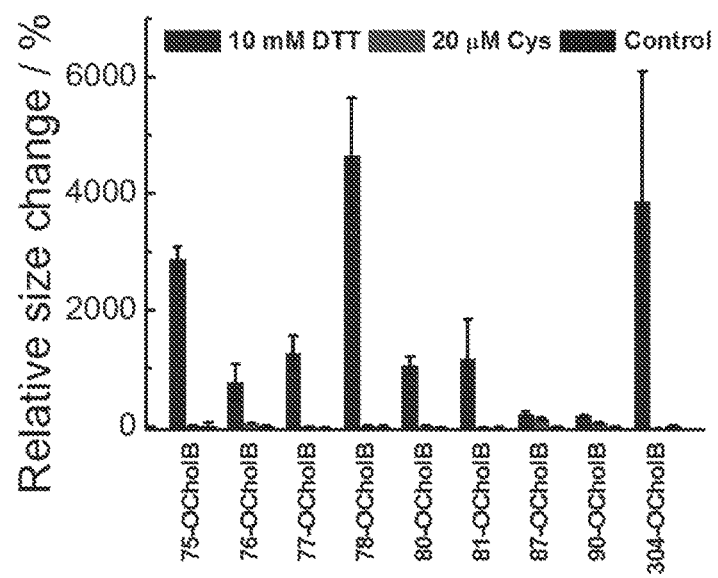
Figure 11:
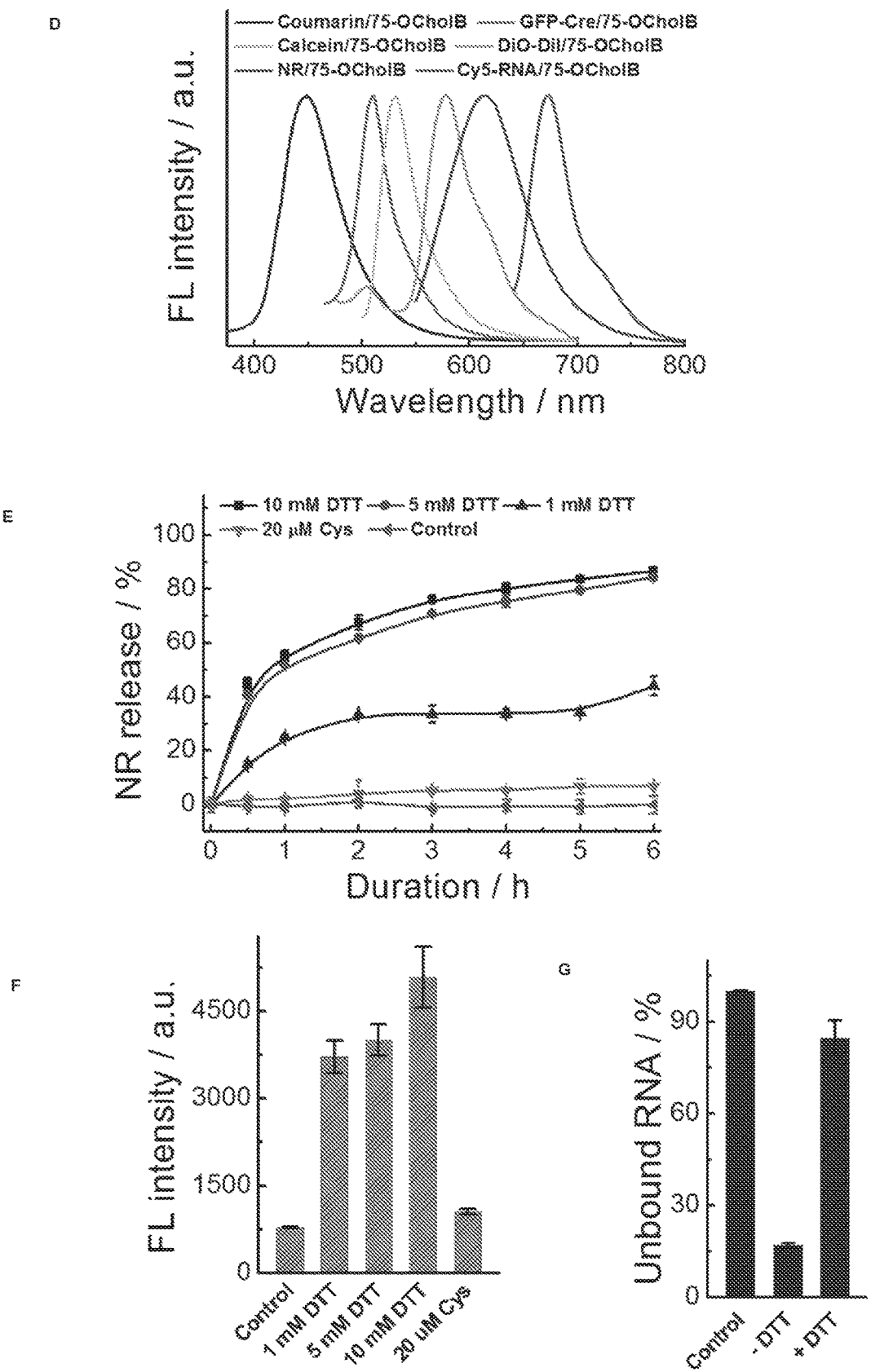

Example 7: Thiol-Responsiveness, Loading and Triggered Release of Guest Molecules The thiol-trigged degradation and dissociation of the OCholB LNPs were studied by time-dependent DLS measurements and TEM observation. Typically, as shown in FIG. 11A, in the presence of 10 mM of 1,4-dithiothreitol (DTT), which has been widely used in previous studies for mimicking intracellular reductive conditions,[25] we observed the increase of the relative sizes of 75-OCholB, 76-OCholB and 77-OCholB gradually increased along incubation duration, as 566.4%, 498.5% and 1591.4% respectively, in first 2 h. Nanoparticle size was then typically maintained over the following 4 h, with the exception of 75-OCholB, which showed 1315.7% increase in size at 6 h. The typical morphologies of DTT treated LNPs were then examined by TEM and images are shown in FIG. 11B. The absence of well-formed vesicular structures as shown in FIG. 10C and large aggregates at micrometer scales (which are consistent with the results obtained from DLS measurements; FIG. 11A) with amorphous structures were observed for 75-OCholB, 76-OCholB and 77-OCholB LNPs. The disruption of the vesicle structure is considered to be resulted from the thiol-exchange and disulfide bond cleavage reactions of OCholB lipidoids. We next investigated whether the thiol-containing molecules (e.g. albumin, cysteine, homocysteine, cysteinylglycine, etc.) in the serum may induce the structural disintegration of these disulfide bond-containing LNPs. The stabilities of LNPs in the presence of 20 µM of L-cysteine (Cys), which mimics the free thiols on the small- and macromolecules presented in the serum, were examined. Shown in FIG. 11A, we observed <25% changes in hydrodynamic diameter at any of the 1 h intervals over the span of this study for all the three tested LNPs, and in fact 12.2%, 14.6% and 7.2% decreases in size were observed for 75-OCholB, 76-OCholB and 77-OCholB after 6 h of incubation, respectively. The size changes of cysteine-treated LNPs showed negligible difference when compared with the untreated control groups (FIG. 11A), indicating the good stability of OCholB LNPs under the conditions mimicking the concentration of free thiols in the blood serum. Furthermore, the relative size variations of the OCholB LNPs after 24 h of incubation in the presence of either 10 mM DTT or 20 µM Cys were determined and the results are shown in FIG. 11C. With 10 mM of DTT and after 24 h of treatment, 75-OCholB, 78-OCholB and 304-OCholB LNPs showed the greatest size changes, with 2872.4%, 4642.8% and 3849.6% increase in averaged hydrodynamic diameters observed; a moderate size increase of 766.9%-1266.4% were recorded for 76-OCholB, 77-OCholB, 80-OCholB and 81-OCholB LNPs; while both 87-OCholB (210.3%) and 90-OCholB (179.5%), which were unable to form consistent vesicles based on the TEM images (FIG. 10C), showed a minimal size increase over 24 hours. On the other hand, all LNPs incubated with 20 µM Cysteine for 24 h showed minimal size changes, similar to the untreated control groups (FIG. 11C). These results demonstrated the kinetics of the degradation of these OCholB LNPs in relation to intracellular and extracellular reducible environments. While the degrees of size changes vary between lipidoids with different amine head groups, all lipidoids were more responsive to DTT (modeling intracellular conditions) than to Cysteine (modeling conditions in the blood serum). Furthermore, the OCholB LNPs showed relative good stability in the presence of low concentrations of thiols (mimicked by 20 µM Cysteine treatment) which indicates that these new LNPs could be used for systemic drug delivery.

Example 8: Drug Encapsulation Using OCholB LNPs

Next, the capabilities of OCholB LNPs as nanocarriers to encapsulate cargo molecules with various physical properties were studied. In this context, coumarin (Excitation (Ex.) 350 nm, Emission (Em.) 448 nm) and Nile red (NR; Ex. 520 nm, Em. 613 nm) as representative small molecular hydrophobic cargoes, calcein (Ex. 475 nm, Em. 529 nm) as a representative small molecular hydrophilic cargo, and (−30) GFP-Cre recombinant fluorescent protein (Ex. 420 nm, Em. 510 nm) and double stranded, Cy5 labeled RNA (Cy5-RNA, 13 kDa; Ex. 625 nm, Em. 672 nm) as representative macromolecular hydrophilic cargoes were used as the model cargoes. 75-OCholB was chosen as the model lipid carrier in the study. FIG. 11D showed that the all the cargoes can be successfully loaded into the 75-OCholB LNPs. The cargo molecules were loaded into LNPs either through hydrophobic interactions (coumarin and NR), electrostatic interactions (calcein, (−30)GFP-Cre and Cy5-RNA), or physical encapsulation. Furthermore, as shown in FIG. 3D, simultaneous encapsulation of cargo molecules could be also achieved using the hydrophobic fluorescence resonance energy transfer (FRET) pair, DiO and DiI (Ex. 425 nm, Em. 504 nm (DiO) and 578 nm (DiI)), as a model, which demonstrates the possibility of using these OCholB LNPs to load multiple types bioactive molecules simultaneously for combination therapies.[30] By taking advantages of the supramolecular interactions (e.g. electrostatic interaction and hydrogen bonding) and/or encapsulating cargoes during the self-assembly process, both small and macromolecular hydrophilic molecules (e.g. genome editing platforms and cell signal inhibitors) could be readily loaded and delivered by the newly developed LNPs.

The reduction triggered release behavior of encapsulated cargoes was then studied by using nile red loaded 75-OCholB LNPs (NR/75-OCholB), taking advantage of the microenvironmental polarity sensitive photophysical property of nile red. As shown in FIG. 11E, in the presence of 1 mM, 5 mM and 10 mM of DTT, 33.5%, 61.7% and 67.4% of encapsulated nile red were released from nile red/75-OCholB LNPs within 2 h, and 44.0%, 84.2% and 86.4% were released in 6 h of incubation, respectively. In the meantime, 20 µM Cysteine treated NR/75-OCholB released 4.2% of nile red in 2 h and 6.9% in 6 h, which could be ascribed to the previously discussed minimal structural and morphological changes of the LNPs under the stimulus of low concentration of thiols (FIGS. 11A and 11C). The triggered release of hydrophilic fluorescent dye, calcein, which possesses a self-quenching feature at high concentrations, was further studied.[31] The fluorescence intensities of DTT (1 mM, 5 mM and 10 mM) treated calcein/75-OCholB LNPs increased 4.7-6.4 folds after 12 h incubation comparing to untreated control LNPs and 20 µM of Cysteine treated groups (FIG. 11F). Furthermore, the binding affinity of OCholB LNPs with negatively charged macromolecular cargo, Cy5-RNA, was examined. It was found that at a 10/1 weight ratio (lipidoid/Cy5-RNA), 82.9% of the RNA molecules could be efficiently complexed with 75-OCholB LNPs, while the binding efficacy dramatically reduced to 15.5% when DTT (10 mM, 24 h) treated nanoparticles were used (as 84.5% unbound Cy5-RNA was determined; FIG. 11G). Additionally, similar to the responsiveness study, it is reasonable that the cargo release profiles could depend on both of the species and concentrations of the thiols-containing regents. Above all, OCholB LNPs loaded with cargoes are relatively stable in the presence of low concentration of thiols and the triggered release behaviors of cargo molecules with different physicochemical properties (hydrophobic/hydrophilic, low/high molecular weight, etc.) could be expected.

Example 9: Internalization Studies

Figure 12:
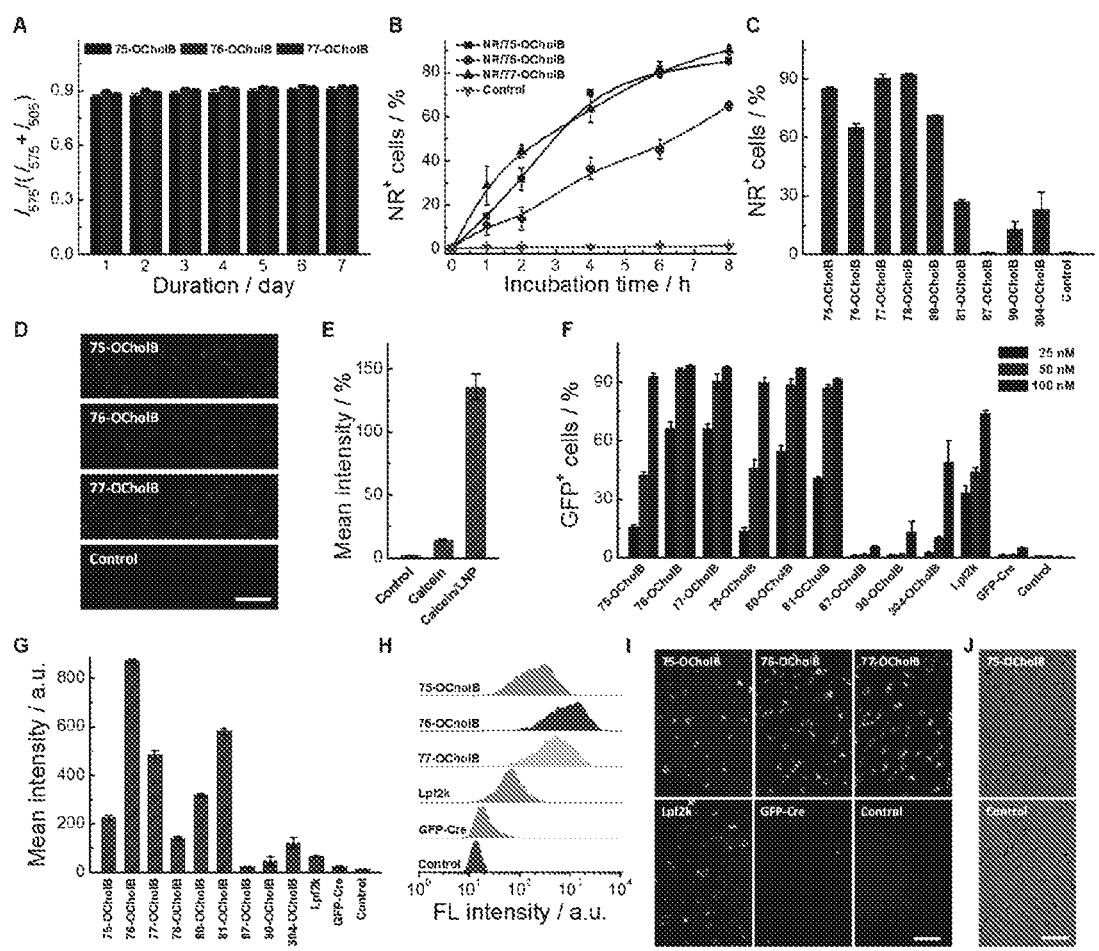
FIG. 12 shows the internalization study of cargo-loaded lipidoid nanoparticles. (A) Time-dependent FRET ratio variation of DiO-DiI loaded nanoparticles. (B) Time-dependent NR$^+$ cells portions of HeLa cells treated with NR loaded nanoparticles. (C) NR$^+$ cells portions of lipidoid nanoparticles after 8 h of exposure. (D) Fluorescent images of HeLa cells treated by NR loaded nanoparticles. Scale bar=100 μm. (E) Mean fluorescent intensity of HeLa cells treated with free or nanoparticles encapsulated calcein. (F) Transfection efficiencies of (−30)GFP-Cre protein by lipidoid nanoparticles against HeLa-DsRed cells. (G) Mean fluorescent intensity, (H) flow cytometry histogram, (I) fluorescent images and (J) bright field images of (−30)GFP-Cre/LNPs treated HeLa-DsRed cells. Scale bar=110 μm.

The cell (HeLa and HeLa-DsRed cell lines) internalization studies were conducted using small molecular hydrophobic (nile red) and hydrophilic (calcein) fluorescent dyes and macromolecular fluorescent recombinant protein ((−30) GFP-Cre) loaded OCholB LNPs. The stabilities of cargo-loaded LNPs were examined at first using time-dependent DLS and fluorescence measurements. As shown in FIG. 12A, the fluorescence intensity of FRET pair DiO and DiI encapsulated LNPs (DiO-DiI/75-OCholB, DiO-DiI/76-OCholB and DiO-DiI/77-OCholB) showed negligible variations on FRET ratio ($I_{575}/I_{575}+I_{505}$) after 7 days of storage.

The internalization kinetics and efficiencies of OCholB LNPs were then studied using NR loaded LNPs and HeLa cells. As shown in FIG. 12B, comparing to the untreated control cells, all the cells incubated with NR/LNPs (NR/75-OCholB, NR/76-OCholB and NR/77-OCholB) showed the percentage of NR positive (NR$^+$) cells gradually increasing over time, which means the internalization process of NR/LNPs is exposure time dependent over the time scale of this study. Furthermore, both NR/75-OCholB and NR/77-OCholB showed a similar NR$^+$ population growth pattern and decreased growth rate after 4 h of exposure (at 4 h, the NR$^+$ percentages for NR/75-OCholB, NR/76-OCholB and NR/77-OCholB treated cells are 85.2%, 65.0% and 90.3%, respectively); while in general, NR/76-OCholB showed a constant increase rate and a lower NR$^+$ percentage after 8 h comparing to NR/75-OCholB and NR/77-OCholB. Next, all of the NR delivery efficiencies of eight OCholB LNPs were determined after 8 h of exposure. As shown in FIG. 12C, NR/75-OCholB, NR/76-OCholB, NR/77-OCholB, NR/78-OCholB and NR/80-OCholB showed highest delivery efficiencies, with 85.2%, 65.0%, 90.3%, 92.3% and 71.4% of cells determined as NR$^+$; 27.0%, 12.9% and 22.8% NR$^+$ cells were recorded for NR/81-OCholB, NR/90-OCholB and NR/304-OCholB; NR/87-OCholB showed lowest transfection efficacy, comparable to the untreated control group, which means 87-OCholB cannot efficiently deliver NR into HeLa cells under the tested conditions. Representative fluorescent images of NR/LNPs (NR/75-OCholB, NR/76-OCholB and NR/77-OCholB) treated HeLa cells are shown in FIG. 12D, from which it is easily observed that NR was delivered into the cells and mainly distributed in cytoplasm, by OCholB LNPs. Next, the internalization of negatively charged hydrophilic fluorescent dye, calcein, was studied. As shown in FIG. 12E, after 8 h of exposure, the free calcein molecules cannot enter into the cells efficiently, which is consistent with previously reported results. Calcein/75-OCholB treated cells showed relatively high green fluorescent intensity, as ~9.4 folds higher mean fluorescent intensity was recorded when compared to the free calcein-treated cells. These results proved that the OCholB LNP may serve as efficient nanocarriers for intracellular delivery of both hydrophilic and hydrophobic cargo molecules. Next, the use of OCholB LNPs for the intracellular delivery of macromolecular cargo was explored, using fluorescent recombinant (−30)GFP-Cre protein and HeLa-DsRed cells as the model system. As shown in FIG. 12F, naked (−30)GFP-Cre and (−30)GFP-Cre loaded Lpf2k ((−30)GFP-Cre/Lpf2k) were used as negative and positive controls, as it has been demonstrated that the naked (−30)GFP-Cre protein cannot enter into the cells and Lpf2k is highly efficient for (−30) GFP-Cre delivery. Delivery efficiency was tested at a range of (−30)GFP-Cre protein concentrations (25, 50 and 100 nM), with a consistent lipid/protein ratio (i.e., delivery with the final lipid concentration of 1.7, 3.3, and 6.6 µg mL$^{-1}$ respectively). 33.2%, 43.8% and 74% of GFP positive (GFP$^+$) cells were recorded for (−30)GFP-Cre/Lpf2k treated cells with the concentration of (−30)GFP-Cre 25 nM, 50 nM and 100 nM, respectively. At the 25 nM (−30)GFP-Cre concentration, (−30)GFP-Cre/76-OCholB (66.4%), (−30) GFP-Cre/77-OCholB (66.4%), (−30)GFP-Cre/80-OCholB (54.7%), and (−30)GFP-Cre/81-OCholB (40.9%) all showed higher transfection efficiencies than (−30)GFP-Cre/Lpf2k. At the higher (−30)GFP-Cre concentrations (i.e. 50 nM and 100 nM), (−30)GFP-Cre/75-OCholB (42.3% and 93.1% GFP$^+$ cells with 50 nM and 100 nM respectively), (−30)GFP-Cre/76-OCholB (96.3% and 98.7%), (−30)GFP-Cre/77-OCholB (90.7% and 97.9%), (−30)GFP-Cre/78-OCholB (46.1% and 90.1%), (−30)GFP-Cre/80-OCholB (88.9% and 97.0%), and (−30)GFP-Cre/81-OCholB (87.4% and 91.5%) showed comparable or even higher transfection efficacies than Lpf2k. 48.8% of GFP$^+$ cells were obtained from (−30)GFP-Cre/304-OCholB treated cells with the concentration of protein 100 nM, while both (−30)GFP-Cre loaded 87-OCholB and 90-OCholB showed lowest delivery efficiencies comparing to other OCholB LNPs. This result is consistent with the small molecular NR delivery results as shown in FIG. 12C, indicating these two nanoparticles are probably inefficient for intracellular delivery applications. Although many of the OCholB LNPs as well as Lpf2k possessed similar GFP$^+$ cells percentages (FIG. 4F), as shown in FIG. 12G ([lipidoid]=6.6 µg mL$^{-1}$ and [(−30)GFP-Cre]=100 nM), further analysis revealed that the mean fluorescence intensities of (−30)GFP-Cre loaded nanoparticles treated cells varied significantly, indicating some of the LNPs (75-OCholB, 76-OCholB, 77-OCholB, 80-OCholB and 81-OCholB) are much more efficient than others (Lpf2k and 78-OCholB), as higher mean fluorescence intensities represent larger amount of (−30)GFP-Cre proteins were successfully delivered into the cells. The typical flow cytometry profiles of naked (−30)GFP-Cre protein and (−30)GFP-Cre loaded nanoparticles ((−30)GFP-Cre/75-OCholB, (−30)GFP-Cre/76-OCholB, (−30)GFP-Cre/77-OCholB and (−30)GFP-Cre/Lpf2k) treated HeLa-DsRed cells were shown in and FIG. 12H ([lipidoid]=6.6 µg mL$^{-1}$ and [(−30)GFP-Cre]=100 nM), which is consistent with the statistical results shown in FIG. 12G. Furthermore, the representative fluorescent images from the protein and protein/nanoparticle treated HeLa-DsRed cells are also shown in FIG. 12I. Strong green fluorescence signals from (−30) GFP-Cre/75-OCholB, (−30)GFP-Cre/76-OCholB, (−30) GFP-Cre/77-OCholB and (−30)GFP-Cre/Lpf2k and negligible signals from (−30)GFP-Cre treated- and untreated cells were detected, which is also consistent with the results from flow cytometry analysis. FIG. 12J shows typical bight field images of (−30)GFP-Cre/LNPs ((−30)GFP-Cre/75-OCholB, (−30)GFP-Cre/76-OCholB and (−30)GFP-Cre/77-OCholB) treated cells ([lipidoid]=6.6 µg mL$^{-1}$ and [(−30)GFP-Cre] =100 nM) and no evident morphological change were observed comparing to the untreated cells, which further demonstrate the biocompatibility of the OCholB LNPs.

Taken together, this data indicates that most of the newly developed fully substituted OCholB LNPs are efficient for the delivery of small molecular hydrophobic and hydrophilic cargoes as well as macromolecular cargoes into mammalian cells in vitro.

Example 10: Intracellular Delivery of Small Molecular Anticancer Drugs

Figure 13:
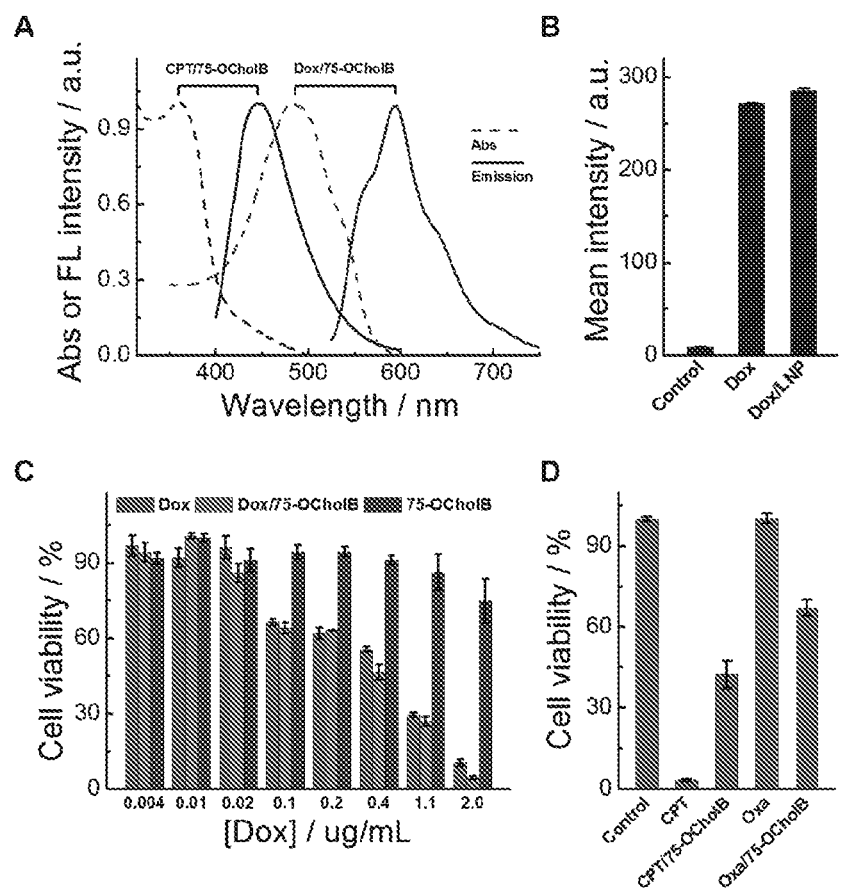
FIG. 13 shows the intracellular delivery of anticancer drugs. (A) Absorption and fluorescent emission spectra of CPT and Dox loaded nanoparticles. (B) Mean fluorescent intensity of free and nanoparticle encapsulated Dox treated HeLa cells. (C) Dose-dependent cytotoxicity of free Dox, and blank and Dox loaded nanoparticles. (D) Cytotoxicity of free and nanoparticle encapsulated CPT and Oxa.

The possibility of using OCholB LNPs to deliver both hydrophobic and hydrophilic small molecular drugs was explored. Doxorubicin hydrochloride (Dox) (water soluble), and camptothecin (CPT) and oxaliplatin (Oxa) (water insoluble) were encapsulated into LNPs (see experimental section) and tested against HeLa cells. The successful encapsulation of small molecular drugs was demonstrated by examining the absorption and fluorescence emission spectra of Dox (Ex. 495 nm, Em. 594 nm) and CPT (Ex. 360 nm, Em. 446 nm) loaded 75-OCholB LNP, in which the characteristic absorbance and emission peaks of Dox and CPT were observed, as shown in FIG. 13A. Using corresponding standard curves, the 1a drug loading contents (DLC %=[$W_{loaded\ drug}$]/[$W_{loaded\ drug}$+$W_{lipidoid}$]*100%) were determined to be 19.2% and 5.2% for Dox and CPT, respectively. Then the internalization of Dox loaded 75-OCholB LNP (Dox/75-OCholB) was studied after 8 h of exposure using flow cytometry. As shown in FIG. 13B, in sharp contrast to calcein (FIG. 12E) and (−30)GFP-Cre (FIG. 4f), free Dox could be readily internalized by HeLa cells after 8 h of incubation. Dox/75-OCholB treated HeLa cells also showed a comparable mean fluorescence intensity as free Dox treated cells, and are ~28.9 folds higher comparing to the untreated control cells, indicating the Dox/75-OCholB nanoparticles could be efficient for intracellular delivery of Dox under this condition.

Dose-dependent cytotoxicity was then examined. From FIG. 13C, the Dox/75-OCholB showed a similar concentration-dependent cytotoxicity profile as free Dox against HeLa cells (8 h of exposure; MTT assay after 48 h of incubation). Meanwhile, blank 75-OCholB LNPs showed negligible toxicity under the same conditions. The cell viabilities treated by blank LNPs maintained to be >80%, which further validates the safety of the OCholB LNPs. Next, hydrophobic anticancer drugs, CPT and Oxa were encapsulated into 75-OCholB LNPs (CPT/75-OCholB and Oxa/75-OCholB) and the cell viabilities of CPT/75-OCholB and Oxa/75-OCholB treated HeLa cells (both with 8 h of exposure; [CPT]=1.8 μg mL$^{-1}$; [Oxa]=2.4 μg mL$^{-1}$) after 48 h of incubation were determined as 42.4% and 66.9% (FIG. 13D). Overall, the Dox and Oxa encapsulated 75-OCholB LNPs showed comparable or even higher toxicities than their free counterparts; while CPT loaded 75-OCholB was less efficient than the free CPT. This indicates that the physicochemical properties of the cargo drugs could have a huge impact on the delivery performances of OCholB LNPs, which in principle may also be true for other carrier systems.

Example 11: Intracellular Delivery of mRNA

Figure 14:
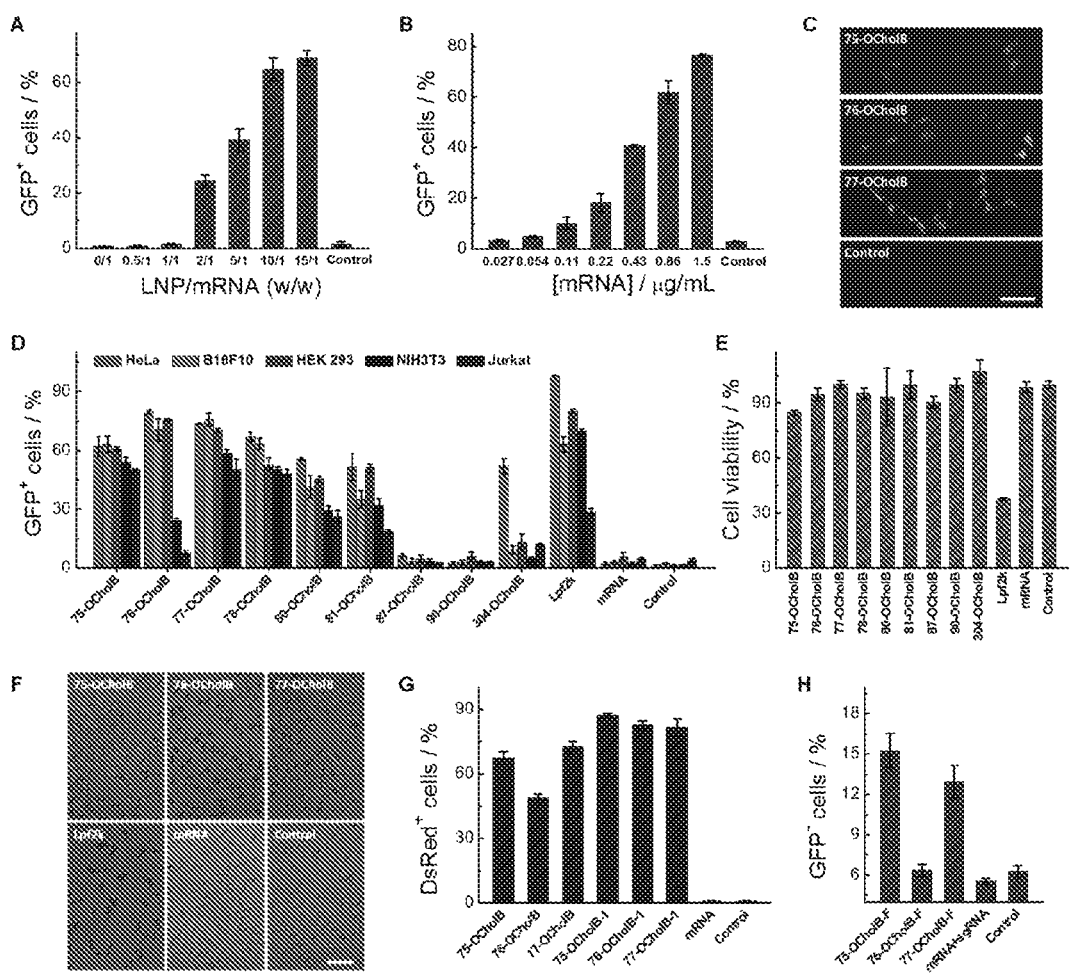
FIG. 14 shows the intracellular delivery of mRNA. (A) LNP/mRNA weight ratio and (B) mRNA dose-dependent transfection efficacy. (C) Fluorescent images of mRNA/LNPs treated HeLa cells. Scale bar=100 μm. (D) Transfection efficiency and (E) cytotoxicity of mRNA/LNPs. (F) Bright field images of mRNA/LNPs treated HeLa cells. Scale bar=110 μm. (G) Cre mRNA and (H) Cas9 mRNA and sgRNA delivery by OCholB LNPs.

Messenger RNA delivery has great potentials for cancer therapy, protein replacement therapy and neurological disorder treatments.[42] The intracellular delivery of mRNA using OCholB LNPs was studied using GFP mRNA and different cell lines (HeLa, B16F10, HEK-293, NIH/3T3 and Jurkat). The weight ratio of LNP/mRNA was optimized at first using HeLa cells. As shown in FIG. 14A, by fixing the final concentration of mRNA as 0.86 μg mL$^{-1}$ and increasing the LNP/mRNA weight ratio from 0/1 (i.e. free mRNA, without LNP) to 15/1, minimal GFP$^+$ cells were determined after 24 h of exposure when the LNP/mRNA ratio is less than 1/1 (0.7%, 0.8% and 1.4% of GFP$^+$ cells were determined for LNP/mRNA=0/1, 0.5/1 and 1/1, respectively). Gradual increase on GFP$^+$ populations were observed when the ratio is increased from 2/1 to 15/1, and 24.3%, 39.2%, 64.7% and 68.9% of GFP$^+$ cells were recorded for LNP/mRNA ratios of 2/1, 5/1, 10/1 and 15/1. The weight ratio of LNP/mRNA=10/1 was then chose for the following mRNA delivery studies. The intracellular delivery of GFP mRNA was also found to be dose dependent in the mRNA concentration range of 0.027-1.5 μg mL$^{-1}$, as continuous increase in GFP$^+$ cells (from 3.3% to 76.3%) were observed when increasing the dosage of mRNA/LNPs (FIG. 14B). Then the intracellular delivery efficiencies of all fully substituted OCholB LNPs were tested against HeLa cells, and Lpf2k and naked GFP mRNA were used as controls (LNP/mRNA=10/1; [mRNA]=0.86 μg mL$^{-1}$; 24 h exposure). As shown in FIG. 14D, naked mRNA induced neglectable GFP$^+$ cells, which is comparable to the untreated cells, while Lpf2k is highly efficient for mRNA delivery, with 98.1% GFP$^+$ HeLa cells. As to the OCholB LNPs, 75-OCholB (62.0% of GFP$^+$ cells), 76-OCholB (79.8%), 77-OCholB (73.5%), 78-OCholB (67.1%), 80-OCholB (55.6%), 81-OCholB (51.6%) and 304-OCholB (52.1%) are all determined to be effective. Typical fluorescent images of mRNA/LNPs (mRNA/75-OCholB, mRNA/76-OCholB and mRNA/77-OCholB) treated HeLa cells are shown in FIG. 14C. Comparing to untreated HeLa cells, strong green fluorescent signals were recoded from nanoparticles incubated cells, which is consistent with the flow cytometry data as shown in FIG. 14D. Meanwhile, both 87-OCholB (6.1%) and 90-OCholB (2.5%) are found to be inefficient for GFP mRNA delivery into HeLa cells, which is consistent with the internalization studies using NR (FIG. 12C) and (−30)GFP-Cre protein (FIG. 12F) as the fluorescent reporters. It was revealed that consistency of the delivery performances may exist among these OCholB LNPs, and the internalization efficacies of non-active LNPs stayed minimal regardless of the properties of loaded cargoes.

To examine the delivery spectrum of the newly developed LNPs, the GFP mRNA loaded OCholB LNPs were then challenged against other four types of cell lines. B16F10 (mouse melanoma cells), HEK 293 (human embryonic kidney cells), NIH 3T3 (mouse embryonic fibroblast cells) and Jurkat (human T lymphocyte cells) cells were tested (LNP/mRNA=10/1; [mRNA]=0.86 μg mL$^{-1}$; 24 h exposure) and the results are shown in FIG. 14D. As the positive control, Lpf2k turned out to be very efficient to deliver GFP mRNA into B16F10 (63.2% of GFP$^+$ cells), HEK 293 (80.1%) and NIH 3T3 (70.1%) cells, while slightly less efficient to Jurkat cell (28.7%), which is usually considered to be one of the most difficult-to-transfect cell lines. As to the OCholB LNPs, in general, 87-OCholB, 90-OCholB and 304-OCholB were proved to be less efficient to deliver mRNA into all these cell lines; while other six OCholB LNPs were found to be much more efficient. For example, 63.0%, 60.9%, 54.1% and 50.1% of GFP$^+$ cells were determined from mRNA/75-OCholB treated B16F10, HEK 293, NIH 3T3 and Jurkat cells; and the numbers for mRNA/76-OCholB treated cells were 70.7%, 75.8%, 24.1% and 7.7%, respectively. It was obvious that not only the types of lipidoids, but also the target cell lines could have huge impacts on the delivery efficacy. Overall, the positive control, Lpf2k, is a relatively high-activity broad-spectrum transfection reagent; most of the OCholB LNPs (6 out of 9)

are also effective broad-spectrum transfection reagents under the tested conditions. Some of the OCholB LNPs (e.g. 75-OCholB, 77-OCholB and 78-OCholB) showed particular advantages over Lpf2k regarding the efficacy of delivery to Jurkat cells. It was expected that through further formulation optimization, such as adding excipients (helper lipids like small molecular phospholipids (e.g. DOPE and DSPC) and macromolecules lipids (e.g. PEG-DSPE and PEG-Ceramide)) into the LNPs and/or using more controllable self-assembly procedures, improved transfection efficiency of the fully substituted OCholB LNPs could be achieved.

Next, the MTT assay was conducted to examine the cytotoxicity of mRNA-loaded nanoparticles against HeLa cells. As shown in FIG. 14E, it was revealed that after 24 h of exposure (lipidoid/mRNA=10/1; [mRNA]=0.86 μg mL$^{-1}$), even though highest GFP$^+$ cells percentage was obtained from mRNA/Lpf2k treated group (FIG. 14D), the mRNA/Lpf2k complex showed significant cytotoxicity against HeLa cells, as 37.5% cell viability was recorded. On the other hand, all of the GFP mRNA loaded OCholB LNPs showed negligible cytotoxicities under the same conditions (e.g. the cell viabilities were determined to be 84.7%, 94.5% and 100.1% for mRNA/75-OCholB, mRNA/76-OCholB, and mRNA/77-OCholB incubated samples), which is consistent with previous toxicity studies of blank OCholB LNPs (FIG. 10E). This result indicate that the excellent compatibility of OCholB LNPs and the possibility to further increase the intracellular delivery efficiencies by increasing the total dosage and/or exposure time of the mRNA/LNPs complexes. From the bight field images shown in FIG. 14F, it is obvious that after 24 h of exposure, significant morphological changes were observed from mRNA/Lpf2k treated cells, while no obvious variations were observed for both the mRNA/LNPs (mRNA/75-OCholB, mRNA/76-OCholB, and mRNA/77-OCholB) and naked mRNA treated cells, comparing the untreated control group. This result is consistent with the cell viability study as shown in FIG. 14E and further validated the advantage of OCholB LNPs as relative safe transfection nanocarriers.

Next, the possibility of using OCholB LNPs to deliver mRNA for genome editing (Cre-loxP and CRISPR/Cas9 systems) purposes was examined. First, Cre mRNA was complexed with OCholB LNPs and tested against HeLa-DsRed cells. The HeLa-DsRed cells express red fluorescent protein, DsRed, only upon Cre protein-mediated recombination. After 24 h of incubation with mRNA/LNPs (lipidoid/mRNA=10/1; [mRNA]=0.86 μg mL$^{-1}$), the DsRed$^+$ cell portions were determined by flow cytometry. As shown in FIG. 14G, 75-OCholB, 76-OCholB, and 77-OCholB were all effective, as 67.2%, 48.7% and 72.8% of DsRed$^+$ cells were recorded, respectively. Then the Cas9 mRNA that expresses a version of *Streptococcus pyogenes* SF370 Cas9 protein with an N and C terminal nuclear localization signal (NLS) were loaded into LNPs, along with single-guide RNA (sgRNA) that targets a sequence on GFP gene. GFP-HEK cells which steadily express GFP proteins were used a cell model in this case. GFP-cells, indicating a successful Cas9-mediated knockdown of GFP expression, were analyzed using flow cytometry. After 48 h of incubation (lipidoid/mRNA/sgRNA=10/1/1; [mRNA]=[sgRNA]=0.86 μg mL$^{-1}$), it was found that all the three tested LNPs (75-OCholB, 76-OCholB and 77-OCholB) were unable to induce any evident GFP knockout under this condition. The GFP$^-$ cells portions recoded for mRNA and sgRNA loaded 75-OCholB, 76-OCholB and 77-OCholB LNPs treated GFP-HEK were 6.1%, 7.7% and 4.4%, respectively, which are comparable to that of untreated control cells (7.0%). The intracellular delivery results of GFP, Cre and Cas9 mRNA molecules as shown in FIGS. 14D and 14G indicated that the efficacies of mRNA/LNPs are dependent on both of the tested cell types and the functions of protein expressed by cargo mRNA molecules. This was also found to be applicable to protein delivery in our previous studies.

In order to further demonstrate the potentials of newly developed OCholB LNPs library in intracellular delivery applications, formulation optimization was explored for improved Cas9 mRNA delivery for genome editing. In this context, two strategies were tested, i.e., synthesizing new OCholB-tailed lipidoids with single tail rather than full substitution, and adding helper lipids (phospholipids) into fully substituted OCholB LNPs. Single-tailed lipidoids, 75-OCholB-1, 76-OCholB-1 and 76-OCholB-1 were synthesized at first following similar protocols as described before and characterized by ESI-MS ([75-OCholB-1+H]$^+$, 736.55; [76-OCholB-1+H]$^+$, 734.64; [77-OCholB-1+H]$^+$, 748.73). Nanoparticles were than fabricated using the same sonication/vortex procedures and the obtained LNPs were measured by DLS (75-OCholB-1, $<D_h>$=302.6 nm, $\mu_2/I^2$=0.30; 76-OCholB-1, $<D_h>$=294.5 nm, $\mu_2/I^2$=0.30; 77-OCholB-1, $<D_h>$=254.2 nm, $\mu_2/I^2$=0.33). The delivery efficacies of the single-tailed LNPs were first tested using GFP mRNA against HeLa cells (lipidoid/mRNA=10/1; [mRNA]=0.86 μg mL$^{-1}$; 24 h of exposure). 69.4%, 72.5% and 68.9% of GFP$^+$ cells were determined for mRNA/75-OCholB-1, mRNA/76-OCholB-1 and mRNA/77-OCholB-1 treated HeLa cells, respectively. Cre mRNA could also be efficiently delivered into HeLa-DsRed cells, as 87.3% (mRNA/75-OCholB-1), 82.8% (mRNA/76-OCholB-1) and 81.5% (mRNA/77-OCholB-1) of cells were determined to be DsRed$^+$ after 24 h of exposure (FIG. 14G). However, it was found that the Cas9 mRNA and sgRNA complexed single-tailed OCholB LNPs also induced negligible GFP knockout against GFP-HEK cells. Single-tailed OCholB lipidoids showed comparable or slightly higher delivery efficacies regarding to GFP and Cre mRNA, while failed with Cas9 mRNA and sgRNA delivery, similar to their two-tailed counterparts. We then tried to add helper lipids into the original two-tailed OCholB lipidoid nanoparticles formulations. As a proof-of-concept, DOPE was mixed with OCholB lipidoids (lipidoid/DOPE=1/1, weight ratio) and nanoparticles were fabricated (noted as 75-OCholB-F, 76-OCholB-F, and 77-OCholB-F) and loaded with Cas9 mRNA and sgRNA (mRNA/sgRNA=1/1, weight ratio). As shown in FIG. 14H, after 48 h of exposure (OCholB lipidoid/mRNA=10/1; [mRNA]=0.86 μg mL$^{-1}$), 76-OCholB-F showed similar GFP$^-$ portion (6.4%) as untreated (6.3%) and naked Cas9 mRNA and sgRNA treated (5.6%) cells. However, increased amount of GFP knockout cells was recorded for 75-OCholB-F and 77-OCholB-F treated GFP-HEK cells, as 15.3% and 12.9% of the cells were determined to be GFP$^-$. These results indicated that nanoparticle formulation optimization could be an effective strategy to achieve improved performances. Overall, it was noted that the GFP knockout efficacies of mRNA loaded OCholB LNPs were relatively low when compared to our previously reported ribonucleoprotein (RNP) delivery results; however, by further molecular design (e.g. incorporating new types of cationic amine head groups to expand the combinatorial library) and supramolecular structural optimization (e.g. screening different species as well as compositions of excipients, optimization of cargo/carrier ratios and incubation conditions like exposure duration and dosage), optimized intracellular delivery and subsequent genome editing performances could be expected.

Example 12: Intracellular Delivery of Genome-Editing Protein

Protein- and peptide-based therapeutics have attracted tremendous attention during last three decades owing to their relatively high specificity and low off-target effects. Formulations for treatment of cancer, infection, inflammation and degenerative diseases have been developed. Effective intracellular delivery methods for proteins and peptides could further expand their therapeutic modalities. As the intracellular delivery of protein using OCholB LNPs has been successfully demonstrated in the previous internalization study using (−30)GFP-Cre protein as cargo and GFP as the fluorescent reporter, the functionality study was conducted using HeLa-DsRed cell line and DsRed protein as the fluorescent reporter.

Figure 15:
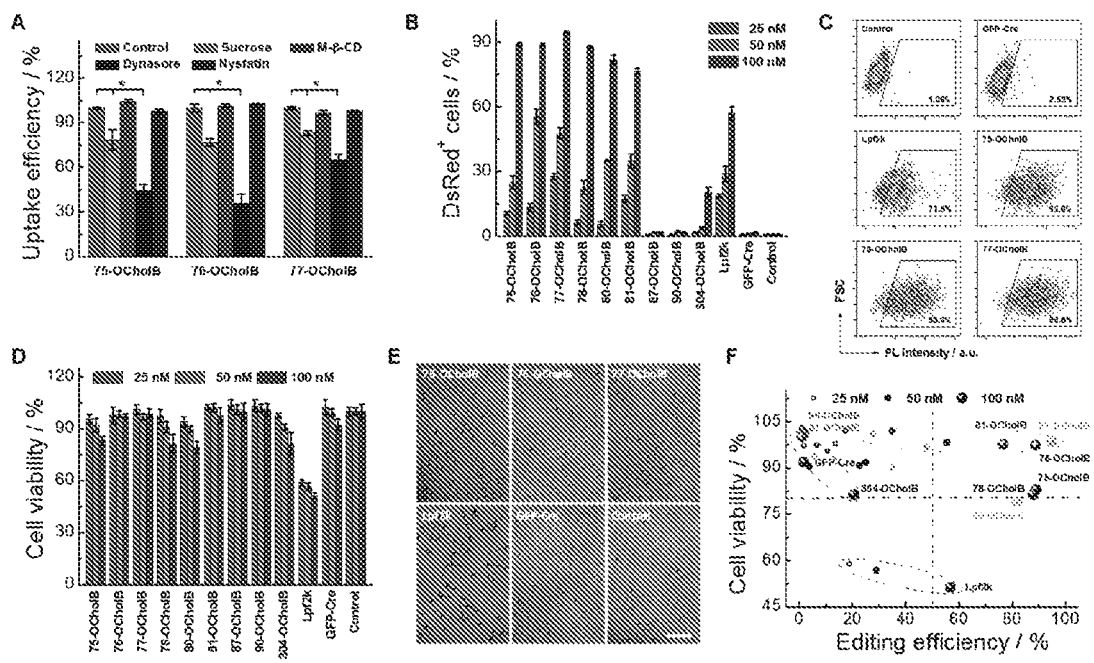
FIG. 15 shows the intracellular delivery of genome editing protein. (A) Internalization mechanism study. (B) Genome editing efficiency, (C) flow cytometry histogram, (D) cytotoxicity and (E) bright field images of (−30)GFP-Cre/LNPs treated HeLa-DsRed cells. Scale bar=200 μm. (F) Genome editing efficacy was plotted against cell viability for each tested conditions.

In this context, the internalization mechanism of the (−30)GFP-Cre/LNPs complexes was studied at first, by introducing different endocytosis inhibitors, i.e., sucrose (clathrin-mediated endocytosis inhibitor), methyl-β-cyclodextrin (M-β-CD, cholesterol-depleting agent), dynasore (dynamin II inhibitor) and nystatin (caveolin-mediated endocytosis inhibitor), following our previously reported procedures. As shown in FIG. 15A, the internalization efficiencies ([lipidoid]=6.6 μg mL$^{-1}$, [(−30)GFP-Cre]=100 nM; exposure duration=6 h) of all three tested protein/LNPs ((−30)GFP-Cre/75-OCholB, (−30)GFP-Cre/76-OCholB, (−30)GFP-Cre/77-OCholB) were significantly suppressed by sucrose and dynasore. M-β-CD and nystatin, on the other hand, did not induce obvious suppression of the cellular uptake of these nanoparticles. This indicates that clathrin and dynamin play important roles in the cellular uptake of these (−30)GFP-Cre protein complexed OCholB LNPs. Comparing to other combinatorial library studies, it is clear that even loaded with same cargoes and tested against same cell line, different lipidoids with different chemical structures could be internalized through very distinct pathways. Next, the genome-editing efficiencies of (−30)GFP-Cre/LNPs were determined by flow cytometry after 24 h of incubation (with 8 h of (−30)GFP-Cre/LNPs complex exposure). Three different concentrations of protein/lipidoid complexes (25 nM/1.7 μg mL$^{-1}$, 50 nM/3.4 μg mL$^{-1}$, and 100 nM/6.6 μg mL$^{-1}$) were tested for each lipidoid nanoparticle. As shown in FIG. 15B, naked (−30)GFP-Cre protein induced negligible genome editing efficacy regardless of the protein concentrations; while all the tested nanoparticles including Lpf2k showed a dose-dependent DsRed$^+$ cell percentage pattern, i.e., higher protein concentration correlate with higher genome editing and DsRed expression level. Three lipids were found to be less efficient at delivery, namely 87-OCholB, 90-OCholB and 304-OCholB (which are also showed to be inefficient for NR and mRNA delivery). All other fully substituted OCholB LNPs (75-OCholB, 76-OCholB, 77-OCholB, 78-OCholB, 80-OCholB, and 81-OCholB) showed comparable or even much higher DsRed$^+$ cells than the positive control, Lpf2k. For example, the DsRed$^+$ cells were recorded as 10.5%/24.9%/88.9%, 13.5%/55.4%/88.8%, and 27.7%/47.8%/94.7% for (−30)GFP-Cre loaded 75-OCholB, 76-OCholB and 77-OCholB, respectively, at the protein concentration of 25, 50 and 100 nM. In particular, six of the OCholB LNPs (75-OCholB, 76-OCholB, 77-OCholB, 78-OCholB, 80-OCholB, and 81-OCholB) out-performed Lpf2k when tested at 100 nM of (−30)GFP-Cre, which further showed the advantage of newly developed LNPs. Furthermore, the typical flow cytometry profiles of (−30)GFP-Cre/LNPs ((−30)GFP-Cre/75-OCholB, (−30)GFP-Cre/76-OCholB, (−30)GFP-Cre/77-OCholB), (−30)GFP-Cre/Lpf2k and naked (−30)GFP-Cre treated HeLa-DsRed cells were shown in FIG. 15C, from which the enhanced DsRed fluorescent signal intensities were observed for the nanoparticles-based delivery systems, which are consistent with the results shown in FIG. 15B. Then, the cytotoxicity profiles of (−30)GFP-Cre/LNPs, (−30)GFP-Cre/Lpf2k and naked (−30)GFP-Cre at different concentrations against HeLa-DsRed cells (8 h of exposure; (−30)GFP-Cre/LNPs=25 nM/1.7 μg mL$^{-1}$, 50 nM/3.4 μg mL$^{-1}$, and 100 nM/6.6 μg mL$^{-1}$) are measured using MTT assay after 24 h of incubation. As shown in FIG. 15D, in general, for all the samples tested, higher (−30)GFP-Cre concentrations induced lower cell viabilities. All nine of protein loaded fully substituted OCholB LNPs showed relatively high cell viabilities. For (−30)GFP-Cre/75-OCholB treated cells, the viabilities were determined to be 95.5%, 91.8% and 83.1%, at the protein concentration of 25, 50 and 100 nM, respectively; the numbers for (−30)GFP-Cre/76-OCholB and (−30)GFP-Cre/77-OCholB are 97.8%/98.2%/97.2 and 100.9%/96.6%/98.6%. The (−30)GFP-Cre loaded 78-OChlB, 80-OChlB and 304-OChlB treated cells showed 79.1-81.4% of viabilities at 100 nM of protein, while all other samples were demonstrated to be non-toxic against HeLa-DsRed cells under the tested conditions. In sharp contrast, Lpf2k showed sever cytotoxicity under the same conditions, as 58.9%, 56.7% and 51.2% of cell viabilities were determined with the concentration of (−30)GFP-Cre at 25 nM, 50 nM and 100 nM, respectively. Meanwhile, the morphology changes of HeLa-DsRed cell treated with different nanoparticle formulations were studied and the results are shown in FIG. 15E. It is clear that similar to the GFP mRNA loaded Lpf2k treated HeLa cells (FIG. 14F), the HeLa-DsRed cells exposed to (−30)GFP-Cre/Lpf2k were unhealthy and shrunk; while those treated with OCholB LNPs ((−30)GFP-Cre/75-OCholB, (−30)GFP-Cre/76-OCholB and (−30)GFP-Cre/77-OCholB) were less affected comparing to the untreated and naked protein treated control groups. The DsRed$^+$ cell percentage was then plotted against the corresponding cell viability for all tested conditions (11 samples with 3 different concentrations), as shown in FIG. 15F, with dotted lines denoting 80% of cell viability and 50% of genome editing efficacy (DsRed$^+$ cell portion), respectively. Samples found in upper left quadrant are non-toxic and inefficient for delivery; samples in lower left quadrant are toxic and inefficient; samples in lower right quadrant are efficient but toxic; samples in upper right quadrant are non-toxic and efficient, which would be top candidates for further study. It is clear that Lpf2k (shown in dotted purple circle) at high concentration is relatively efficient for genome editing, while also toxic to the target cells. On the other hand, most of the (−30)GFP-Cre loaded OCholB LNPs are almost non-toxic when compared to (−30)GFP-Cre/Lpf2k, similar to naked (−30)GFP-Cre protein. 87-OCholB, 90-OCholB and 304-OCholB (shown in dotted dark blue circle) are less efficient for genome-editing; while high genome editing efficacy and excellent tolerability were achieved by using 75-OCholB, 76-OCholB and 77-OCholB (shown in dotted green circle). Above all, these results indicated that the newly developed OCholB LNPs could serve as highly efficient and safe nanocarriers for Cre recombinase protein delivery for in vitro genome editing.

Example 13: In Vivo Toxicity Study

Figure 16:
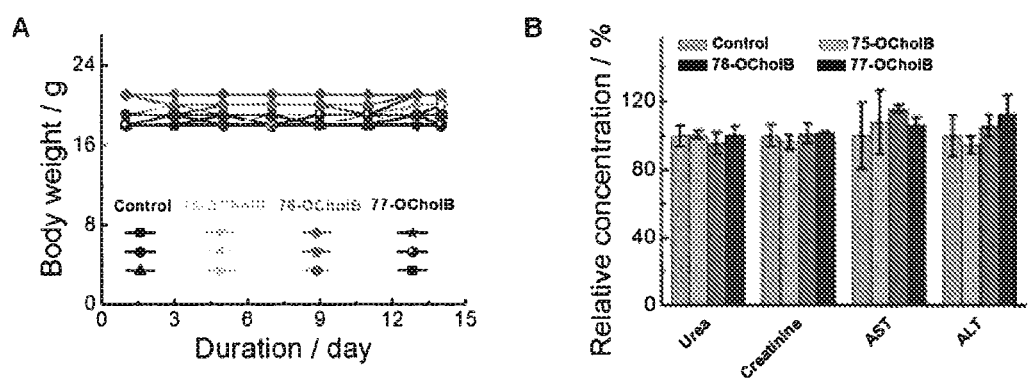
FIG. 16 shows the In vivo toxicity tests. (A) Time-dependent body weight and (B) biochemical blood analysis of blank LNPs injected Balb/c mice.

Both the blank (FIGS. 10E and 13C) and cargo (GFP mRNA and genome editing protein) loaded (FIGS. 14E and 15D) OCholB LNPs showed relative high biocompatibility in vitro. The in vivo toxicity of the OCholB LNPs was further examined by measuring body weight change and biological functions of kidney and liver through serum biochemical tests using Balb/c mice. 4-6 weeks old Balb/c mice (n=3) were injected with blank 75-OCholB, 76-OCholB and 77-OCholB LNPs (50 µg LNPs for each injection) through tail vein at day 1 and day 5, body weights were monitored for 14 days, and blood were collected and analyzed at day 14. As shown in FIG. 16A, comparing to the untreated control group, the body weights of LNPs (75-OCholB, 76-OCholB and 77-OCholB) injected mice showed negligible differences throughout the study. Serum concentrations of creatinine, urea, aspartate aminotransferase (AST), and alanine aminotransferase (ALT) of LNPs injected mice were very similar to control mice (FIG. 16B).

These results indicated that these OCholB LNPs would not induce significant body weight change or serve organ damages through systemic administration under the tested conditions, indicating these LNPs could be used as safe carriers for in vivo delivery purposes.

Example 14: In Vivo Protein and mRNA Delivery for Genome Editing

Figure 17:
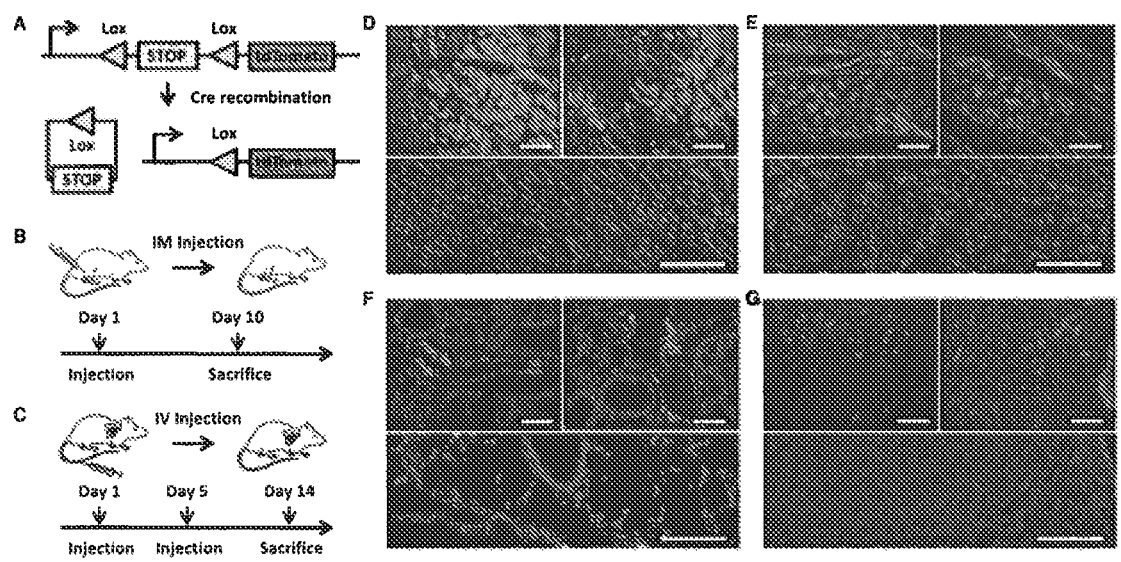
FIG. 17 shows the mRNA and protein delivery for in vivo genome editing using adult Ai14 mice. (A) Cre-mediated gene recombination. Protocols used for (B) intramuscular and (C) intravenous injections. Fluorescent images of (D) intramuscular protein/LNPs (scale bar=270 μm) and (E) intramuscular mRNA/LNPs (scale bar=270 μm) injected skeletal muscles. Fluorescent images of (F) lungs from control and intravenous protein/LNPs injected mice (scale bar=135 μm) and (G) spleens from intravenous mRNA/LNPs injected mice (scale bar=190 m). Red channel in the original image, tdTomato; Blue channel in the original image, DAPI. Images in up panels are from nanoparticles injected mice and images in low panels are from untreated control mice.

Cre-loxP system and transgenic Ai14 mouse model were used in the in vivo genome editing study. As shown in FIG. 17A, this mouse model has a genetically integrated loxP-flanked STOP cassette that prevents the transcription of red fluorescent protein, tdTomato. When the Cre recombinase mediated gene reorganization occurs, the STOP cassette could be removed, resulting in the expression of fluorescent tdTomato reporter protein.

Local delivery through intramuscular injection (IM injection; rear leg) using (−30)GFP-Cre protein and Cre mRNA loaded 76-OCholB LNPs (FIG. 17B). Ai14 mice (n=3) received single dose of (−30)GFP-Cre/LNPs (50 µg of protein) or mRMA/LNPs (10 µg of mRNA) injection at day 1 and were sacrificed at day 10. Skeletal muscles were collected, fixed, cryosectioned and imaged for tdTomato expression analysis (see experimental sections). As shown in FIGS. 17D and 17E (Blue channel, DAPI; Red channel, tdTomato), contrary to untreated control muscle, strong tdTomato fluorescent signals from both (−30)GFP-Cre/LNPs and mRNA/LNPs injected muscles were recorded. A larger portion of tdTomato positive cells were found in the protein/LNPs injected muscle samples than the mRNA/LNPs counterpart.

The OCholB LNPs was further investigated if they can induce successful gene editing in vivo through a systemic administration pathway. At first, Ai14 mice (n=3) were injected through tail vein (intravenous (IV) injection) with (−30)GFP-Cre protein loaded LNPs at day 1 and 5 (50 µg protein for each injection; 100 µg in total), then sacrificed at day 14 for analysis (FIG. 17C). In this case, five of the top OCholB LNPs that have been demonstrated to be effective in vitro as shown in FIG. 17F are tested, i.e., 75-OCholB, 76-OCholB, 77-OCholB, 78-OCholB, 80-OCholB. The heart, liver, spleen, lung and kidney from each group were collected and analyzed. Relative high genome editing efficacy was achieved in the lung and spleen of (−30)GFP-Cre/80-OCholB and (−30)GFP-Cre/76-OCholB injected Ai14 mice, respectively, as shown in FIG. 17F. Like most intravenous nano-therapeutics, the (−30)GFP-Cre protein complexed OCholB nanoparticles injected through tail vein would travel first to the heart, and from there directly to the lung. The nanoparticle formulations (which may have complexed with serum proteins) could be easily trapped in the vasculature structures in the capillary bed of the lung, delaying or inhibiting the redistribution of LNPs to the liver, spleen and other organs. During the in vivo transport and redistribution process, some of the protein loaded LNPs may successfully enter into the cells in lung or spleen to induce the genome editing and tdTomato expression cascade. Degradation, aggregation and/or immune cells sequestration of the cargo protein and carrier LNPs would dramatically reduce or perhaps even prohibit genome editing events. Nevertheless, 80-OCholB and 76-OCholB were demonstrated to be efficient for (−30)GFP-Cre protein delivery into lung and spleen, respectively, in vivo through systemic administration.

Next, in vivo systemic mRNA delivery using OCholB LNPs was tested using a similar intravenous injection protocol (FIG. 17C). Cre mRNA loaded 76-OCholB LNPs were injected at day 1 and day 5 (10 µg mRNA for each injection; 20 µg in total), and mice were sacrificed at day 14. All the major organs (heart, liver, spleen, lung and kidney) were collected and analyzed. As shown in FIG. 17G, significant amount of tdTomato positive cells were recorded in the spleen, and positive signals were not found in other organs. It was noted that both of the (−30)GFP-Cre protein and Cre mRNA loaded 76-OCholB LNPs induced genome editing in the spleen, which indicated that the nature of carrier lipidoids may impact the metabolism and biodistribution of the whole delivery system. Overall, the genome editing efficacies of systemically administered nanoparticles (both of the (−30)GFP-Cre protein and Cre mRNA loaded LNPs) seemed much lower than that of local injection, which is understandable as the formulations injected through vein would encounter much more physical as well as biochemical barriers. However, it is still worth pursuing as systemic administration supplies a wide range of possibilities for the treatment of human conditions or diseases. Above all, these in vivo genome editing results suggested the possibility of using OCholB LNPs as nanocarriers to deliver functional proteins as well mRNA in vivo both through the systemic and local administrations routes for genome editing purposes.

Materials and Methods

General

The chemicals used for lipidoids synthesis, amphotericin B and commercial kits used to assess hepatotoxicity and nephrotoxicity were purchased from Sigma-Aldrich. 1,2-distearoyl-sn-glycero-3-phosphoethanolamine-N-[amino (polyethylene glycol)-2000](DSPE-PEG2000 Amine) was ordered from Avanti. HEK293 cells were cultured in Dulbecco's modified eagle's medium (DMEM, Sigma-Aldrich) with 1% penicillin-streptomycin (Gibco) and 10% fetal bovine serum (FBS, Sigma-Aldrich). Hydrodynamic sizes and polydispersity indexes (PDI) of AmB nanoparticles were measured by Zeta-PALS particle size analyzer (Brookhaven Instruments). The concentration, RBC hemolysis and cell viability of AmB encapsulates were measured by SpectraMax M2e microplate readers. The AmB encapsulates were lyophilized by freeze Dryer (Labconco). Human whole blood was ordered from Research Blood Component, LLC. The strain of *C. albicans* (SC5314) was obtained from the laboratory of Professor Carol A. Kumamoto in Department of Molecular Biology and Microbiology of Tufts medical center. Tissue samples (100 mg) were ground by bead bug microtube homogenizer (Benchmark scientific). The plasma and tissue concentration of AmB were measured by high performance liquid chromatography (HPLC) (Agilent 1200) in chemistry department of Tufts University. Female BALB/c mice (age 6-8 weeks, weight 20-30 g) and female Sprague Dawley rats (age 8-10 weeks, weight 200-250 g) were ordered from Charles River. The animal protocol of this study was approved by the Institutional Animal Care and Use Committee (IACUC) of Tufts University (B2018-73) and all in vivo experiments were performed under the approved animal care guidelines.

Preparation of AmB Nanoparticles.

The AmB encapsulates were prepared as follows: Briefly, 1 mg each lipidoid was mixed with 1 mg AmB which was already dissolved in 300 µl Dimethyl sulfoxide (DMSO). The mixtures were sonicated for 30 minutes and then vortexed for 10 minutes until each was completely dissolved. Then the AmB nanoparticles were formulated with 10 mg/mL DSPE-PEG dissolved in ethanol with the mole ratio of 1:6.8 (DSPE-PEG to lipidoids). As a control group, the AmB nanoparticles were not formulated with DSPE-PEG. Each solution was added drop-wise to a glass bottle containing 600 µl sodium acetate buffer (pH 5.0) with continuous homogenization at 700 rpm. Then the solutions were further dialyzed against distilled water by using the dialysis bag (MWCO: 3500 Da) for 4 h to remove the DMSO and sodium acetate buffer with a stirring speed of 600 rpm/min. The AmB encapsulates were transferred to 2 ml glasses bottles to observe their visual transparency for 2 weeks. The data recorded are the mean of three experiments carried out independently.

Stability and Particle Size

The particle sizes and PDI were assayed by dynamic light scattering (DLS), 1 and 2-week endpoints to evaluate the stability of AmB nanoparticles. Mean size (nm) and PDI were determined based on size distribution by number. The AmB nanoparticles were dispersed in deionized water with 10-fold dilution before measurement. Three runs of 60 s per sample were carried out at a detection angle of 90° in the same conditions. All nanoparticles were prepared and measured in triplicate.

Drug Loading Content

In order to quantify the amount of AmB loaded, regression calibration curve of AmB concentration was calculated by studying the absorbance of different AmB concentrations (0.001-1.0 mg/mL) dissolved in DMSO by SpectraMax M2e. The wavelength ranging from 300 to 450 nm was selected for UV-Vis absorbance spectrum. The amounts of AmB encapsulated into liposome were determined by dissolving the nanoparticles in DMSO and then their absorbance at 392 nm wavelength were measured. The drug loading content (DLC) of AmB was calculated according to linear regression calibration curve and then the following equation: Drug loading content (%)=$W_{loaded}$×100/$W_{polymer}$+$W_{loaded}$, where $W_{loaded}$ is the weight of AmB loaded in the liposomes after encapsulation, and $W_{polymer}$ is the weight of lipidoids. The data recorded are the mean of three experiments carried out independently.

In Vitro Antifungal Activity

The minimum inhibitory concentration (MIC) and *C. albicans* (SC5314) strain were used to test antifungal efficacy of AmB encapsulates in vitro according to the Reference Method for Broth Dilution Antifungal Susceptibility Testing of Yeasts. Briefly, the yeast was grown on Sabouraud Dextrose Agar (SDA) plates and inoculated into water to yield a final inoculum concentration of 1-5×10$^6$ yeast cells/mL. *C. albicans* cells suspension was diluted 1:20 in RPMI-MOPS growth medium and 100 µl dispensed into a microliter tray containing a serial concentration of AmB range from 0.125 to 32 µg/mL and 0.109375 µg/mL to 14.0 µg/mL. Three wells containing drug-free medium and inoculum were used as positive and negative controls. The inoculated plates were incubated at 35° C. for 48 h. The growth in each well was visually estimated at 24 h and 48 h. The MIC was recorded to be the lowest concentration of AmB that prevented visible growth of *C. albicans* and expressed in µg/mL. The data recorded are the mean of three experiments carried out independently.

Hemolysis Test from Human Erytrocytes

In order to screen the optimized AmB encapsulates, high doses of AmB encapsulates were needed in toxicity evaluation. The AmB encapsulates were lyophilized by cryoprotectant, then were reconstituted to properly volume with filtered deionized water followed by shaking to get homogenous liposomal dispersion. The hemolysis was performed as previously described. Venous blood obtained from a healthy volunteer stored at 6±2° C. Whole blood was centrifuged (30 min at 1,600×g) and the supernatant was pipetted off and discarded. RBCs were then washed three times with isotonic PBS of pH 7.4 and were finely dispersed in PBS at 2% stock solution. Subsequently, 90 µl of the RBCs suspension were mixed with 10 µl of PBS containing different AmB encapsulates, free AmB and Fungizone® in triplicate. The final AmB concentration was 200, 100, 50 and 25 µg/mL respectively in all nanoparticles. Each sample was then incubated at 37° C. After 1 h incubation, hemolysis was stopped and RBCs not lysed were removed by centrifugation (5 min at 5000×g). The supernatants were collected for analysis to determine the extent of hemolysis by reading the absorption of hemoglobin at 540 nm by SpectraMax M2e. Hemolysis (%)=($Abs_s$−$Abs_0$)×100/($Abs_{100}$−$Abs_0$), where Abs is the absorbance of AmB encapsulates, $Abs_{100}$ is absorbance of the 100% lysed sample treated with 1% Triton X100 sample and $Abs_0$ is the absorbance of unlysed sample treated with PBS.

In Vitro Toxicity in Mammalian Cells

Human embryonic kidney HEK293 cells were used to evaluate cell viability of AmB encapsulates. The cells were transferred to 96-well tissue culture plates at 5×10$^3$ cells per well and incubated for 24 h at 37° C. prior to drug treatment which containing different concentrations of AmB encapsulates, free AmB and Fungizone® (equivalent of AmB 200, 100, 50 and 25 µg/mL). 30 µl of MTT stock solution (5 mg/mL) was added to each well and the plates were incubated for 4 h at 37° C. After discarding the culture medium, 200 µl DMSO was added to dissolve the blue formazan crystals converted from MTT. Cell viability was assessed by measuring the absorbance at 570 nm by SpectraMax M2e. The cell viability was expressed as percentage calculated with the absorbance obtained from control well without drug treatment using the following equation: Cell viability (%)=$Abs_t$/$Abs_c$×100%, where $Abs_t$ is the absorbance of drug-treated well and $Abs_c$ is the absorbance of control well without drug treatment.

Pharmacokinetics Analysis Studies

For this experiment, six female Sprague Dawley rats were fasted overnight for about 12 h with free water access and were divided randomly in two groups. Considering the maximum tolerated dose (MTD) of Fungizone® is 2 mg AmB/kg, the rats were intravenously administered via tail vein with either screened AmB encapsulate or Fungizone® at a single dose equivalent of AmB 2 mg/kg. The blood samples (~0.5 ml) of each group were collected in heparinized tubes by retro-orbital puncture at each time point (10, 30 min and 1, 2, 4, 6, 8, 12, 24, 36 h) after administration. Each blood sample was centrifuged at 10000 rpm for 10 min and plasma was collected for the determination of the AmB concentration. Two parts of methanol was added into one part of the plasma. The mixtures were vortexed for 5 min followed by centrifugation (13000 g, 4° C. and 30 min). The supernatants were collected for HPLC as described previously. HPLC analysis of each sample was performed with a modular liquid chromatograph system (Agilent™). The mobile phase consisted of acetonitrile and 10 mM sodium acetate buffer, pH 4.0 (40:60, v/v) and the flow rate kept at 1 mL/min. Compounds were separated on a 4.6×100 mm, 3.5 µm size eclipse plus C18 reverse-phase column. The relative retention time of AmB was 4 min. The effluent was monitored at 408 nm. Plasma AmB concentrations were calculated from linear regression calibration curves. Non-compartment pharmacokinetic analysis of Pks software designed by Zhang was used to evaluate the AmB plasma concentrations versus time data.

Tissue Biodistribution Test

Twenty-four BALB/c mice were randomly divided into four groups (n=6) for the tissue distribution study. Three groups were injected with screened AmB encapsulates via tail vein at a single dose of 10 mg, 5 mg, 2 mg AmB/kg respectively. One group was intravenously injected with Fungizone® at a single dose of 2 mg AmB/kg. Three mice of each group were sacrificed by $CO_2$ inhalation, and tissues (liver, spleen, lungs, kidney, heart and brain) were taken out at 48 h and 72 h post administration respectively and kept at −80° C. until they were further processed. Tissue samples (100 mg) were ground and homogenized with 200 µl DI water in a high-speed by bead bug tissue homogenizer (2 min, 4000 rpm). Two parts of methanol were added into one part of the homogenate. The resulting mixtures were vortexed for 2 min followed by centrifugation (13000 g, 4° C. and 30 min). The supernatants were used for HPLC analysis in the same way as pharmacokinetics analysis.

Hepatotoxicity and Nephrotoxicity Tests

Fifteen female BALB/c mice were randomly divided into five groups (n=3). Three groups were injected with screened AmB encapsulate via tail vein at a single dose of 10 mg, 5 mg, 2 mg AmB/kg, respectively. One group was administrated in the same way with Fungizone® at single a dose of 2 mg AmB/kg. The control group was injected with PBS. The blood samples (~0.2 mL) were collected by the mandibular vein puncture at 48 h and 72 h after injection and were allowed to coagulate at 4° C. and then centrifuged for 10 min at 5000 rpm to collect the serum. Kidney and liver biochemical parameters were performed as per the manufacturer's guidelines to analyse the nephrotoxicity and hepatotoxicity investigations including Creatinine (Cr), Blood urea nitrogen (BUN), Alanine aminotransferase (ALT) and Aspartate aminotransferase (AST). The concentrations were calculate based on the regression calibration curves of each kit.

Statistical Analysis

All data expressed as mean±standard deviation (SD). The difference among the groups was evaluated by two-way analysis of variance (ANOVA) followed by the Turkey-Kramer multiple comparison test for more than two groups, and student t-test for comparing two groups using Prism software (Graph Prism7.0 Software Inc. CA, USA). The differences were considered significant when $p<0.05$. Whereas $*p<0.05$ and $** p<0.001$ versus control group described in the legends.

Example 15: Optimization of AmB Lipidoids Encapsulates and Stability Evaluation

Figure 18:
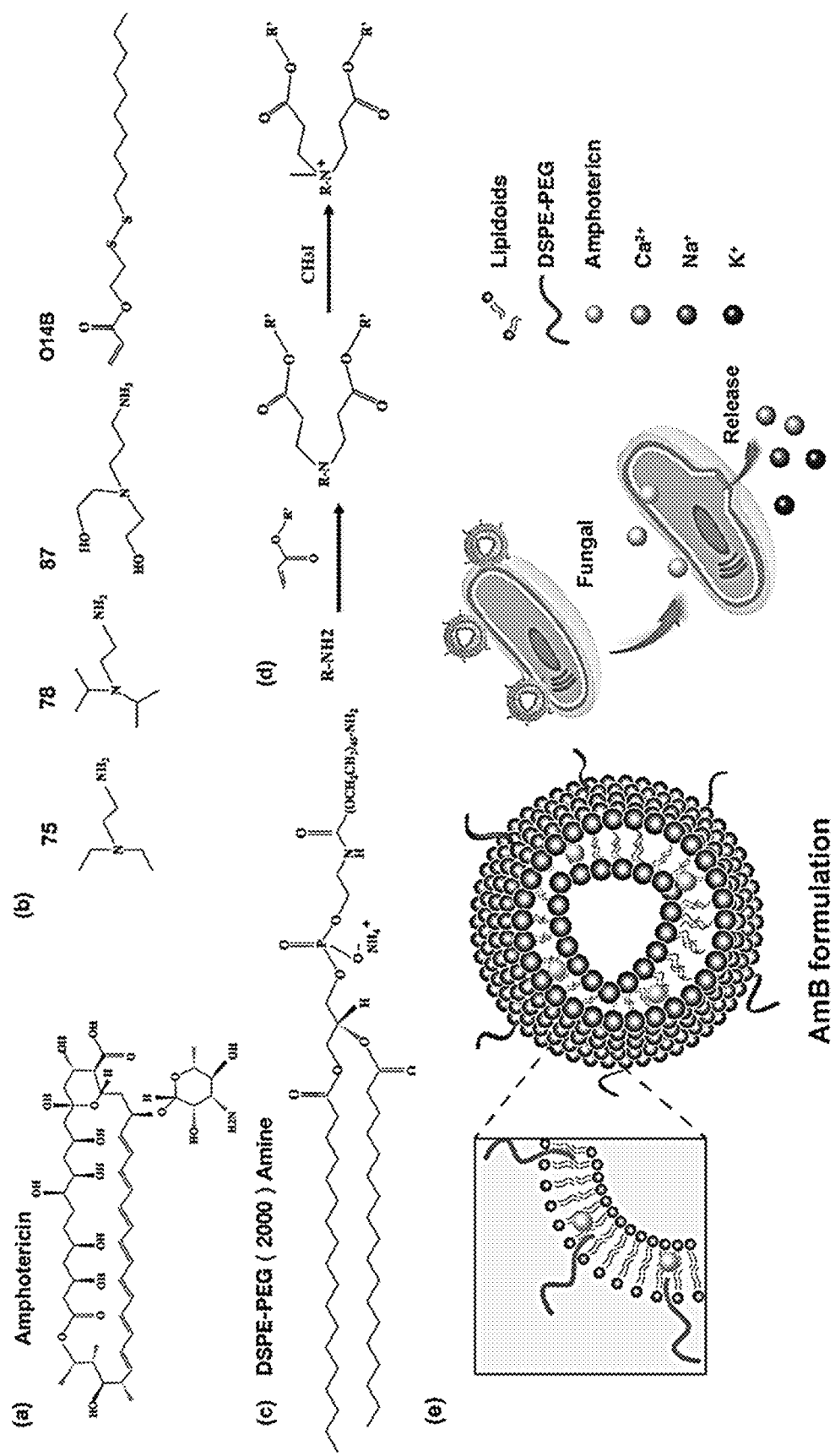
FIG. 18 is a schematic presentation showing (a) Encapsulation of AmB into synthetic cationic lipidoids nanoparticles and effect on fungus cells. (d) The quaternized lipidoids were combinatorial synthesized of the amine and alkyl-epoxide molecules, lipidoids are named as follows (Carbon numbers of tail)-(Amine number)

AmB is poorly soluble in aqueous and organic solvents. Its water solubility at physiological pH is less than 1 mg/L. The amphipathic property rendered a challenge for efficient and economical deliver. The amphipathic characteristic rises from the apolar and polar sides of the lactone ring, while the amphoteric property is due to the presence of ionizable carboxyl and amine groups (FIG. 18a). AmB was first formulated with different lipidoids 75-O14B, 78-O14B or 87-O14B, opaque suspensions were obtained, but all precipitated in less than 1 week as show in FIG. 2. The particle sizes increased dramatically and the PDI increase to more than 0.7 at the end of 2 weeks. As we all know, the particle size plays an important role in pharmacokinetics and toxicity. Because particle size larger than 100 nm in diameter is easily interacts with plasma proteins, then can be easily recognized by RES and eliminated more rapidly from blood such as Amphocil®. However, too small particle size could increase glomerular filtration and drug renal excretion such as Fungizone®. The optimizable size of nanoparticle is 50-100 nm.

Figure 19:
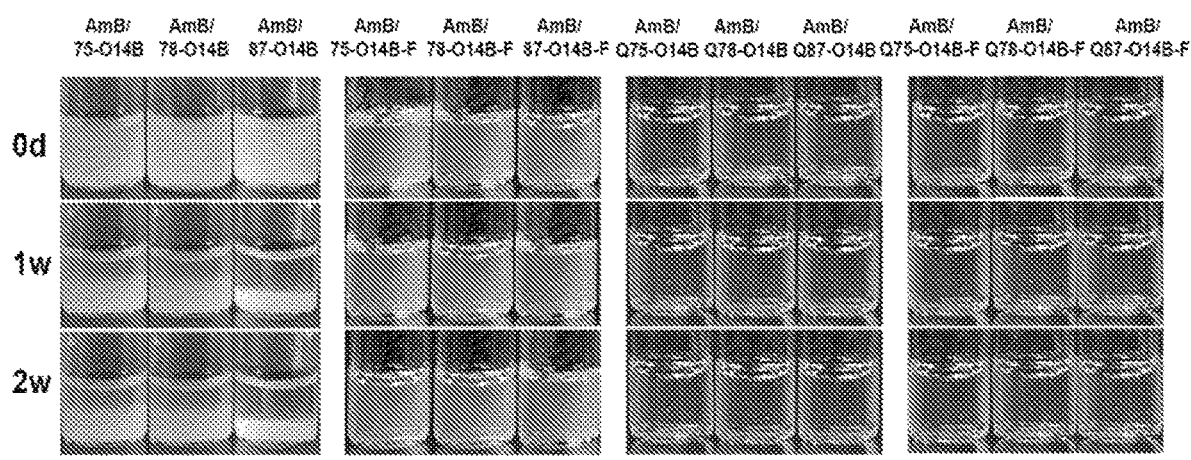
FIG. 19 shows the visual stability states after preparation: AmB/(75-O4B, 78-O14B, 87-O14B) encapsulates demonstrated opaque suspension and all precipitated within 1 week, AmB/(75-O14B, 78-O14B, 87-O14B)—F encapsulates demonstrated translucent solutions after preparation and not homogenize at the end of 2 week, AmB/(Q75-O14B, Q78-O14B, Q87-O14B) and AmB/(Q75-O14B, Q78-O14B, Q87-O14B)-F encapsulates exhibit homogenous transparent yellow solutions and stable in the following 2 weeks.
Figure 20:
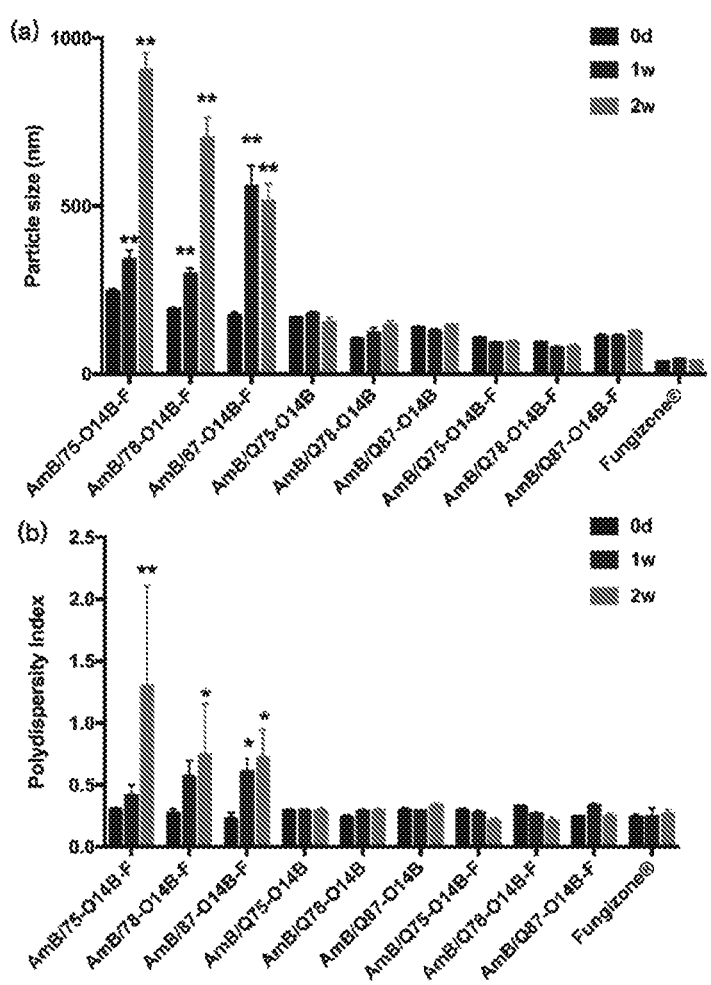
FIG. 20 shows (a) Hydrodynamic sizes of AmB encapsulates and Fungizone® after preparation and in following 2 weeks (n=9), (b) Polydispersity indexes of AmB encapsulates after preparation and in following 2 weeks determined by DLS(n=9). *p<0.05 and ** p<0.001 vs the particle size and PDI after preparation.

To increase the solubility and stability, AmB was either formulated with DSPE-PEG or encapsulated in QLDs. As a result, the nanoparticles demonstrated better drug solubility with more clearly yellowish color translucent solutions, but still a little cloudy when formulated with DSPE-PEG2000 (FIG. 19). The particle sizes increased to 500-900 nm and PDI increased to more than 0.5 at the end of 2 weeks (FIGS. 20a and 20b). However, when AmB was loaded by QLDs, homogenous transparent yellow solutions were obtained and remained stable in the following 2 weeks (FIG. 2). The particle sizes were decreased to 100-160 nm, but still a little higher than the optimizable size of nanoparticles (FIGS. 20a and 20b). Therefore, we further formulated DSPE-PEG with QLDs to encapsulate AmB. The particle sizes of AmB/Q75-O14B-F and AmB/Q78-O14B-F decreased to 70-100 nm (FIG. 20a). Although the particle size of AmB/Q87-O14B-F was a little high (110-120 nm), but it still decreased as compared to AmB/Q87-O14B. The quaternized liposomal vesicles either formulated with DSPE-PEG or not were all homogeneous and similar in nature with regards to particle size and PDI after preparation even following 2 weeks period (FIG. 20b).

QLDs and DSPE-PEG enable the formation of stable AmB encapsulates and facilitate produce smaller condensed structure, in which AmB was intercalated between the lipid bilayer (FIG. 18a). The stability of liposome depended on the nature of the phospholipid molecules contained in their structure. QLDs having two quaternized amine heads characterized by its higher solubility, easier and economic combinatorial synthesis as well as higher delivery efficiencies, which make the QLDs attractive. PEG is biocompatible, but a large amount is needed for the water-soluble AmB complex. QLDs increased the AmB solubility property and decreased the amount of DSPE-PEG with 1:6.8 PEG-to-lipidoid molar ratio. The lipidoids were quaternized by being dissolved in THF and reacting with excessive amount of methyl iodide overnight at room temperature in the dark. The precipitations were filtered, washed with diethyl ether then dried in vacuum (FIG. 18a). Another superior aspect of AmB encapsulates described here is less-cost excipients and easier preparation as compared to Ambisome®. Ambisome® is formulated with injectable good manufacturing practice (GMP)-grade cholesterol because of the agents of bovine spongiform encephalopathy/transmissible spongiform encephalopathy and the related analysis procedure, which make the final product expensive.

Example 16: Drug Loading Content

AmB dissolved in DMSO exhibited three main spectrophotometric peaks in the UV range consistent as previously reported. AmB concentrations were measured by absorbance of properly diluted ratio at 392 nm and calculated by calibration curve with correlation coefficient equivalent to 0.9985. The DLC of AmB encapsulates were 38.9-49.9% indicating excellent association of AmB with the liposomes as show in FIG. 21a. AmB/Q78-O14B-F showed the highest DLC about 49.9% among these encapsulates. The DLC efficiency depending on the polarity and partition coefficient determined its localization in liposomal membrane. Because the AmB is amphipathic, it resides in the acyl hydrocarbon chain, adjacent to the water-lipid interface (FIG. 18a).

Example 17: In Vitro Antifungal Activity

Figure 21:
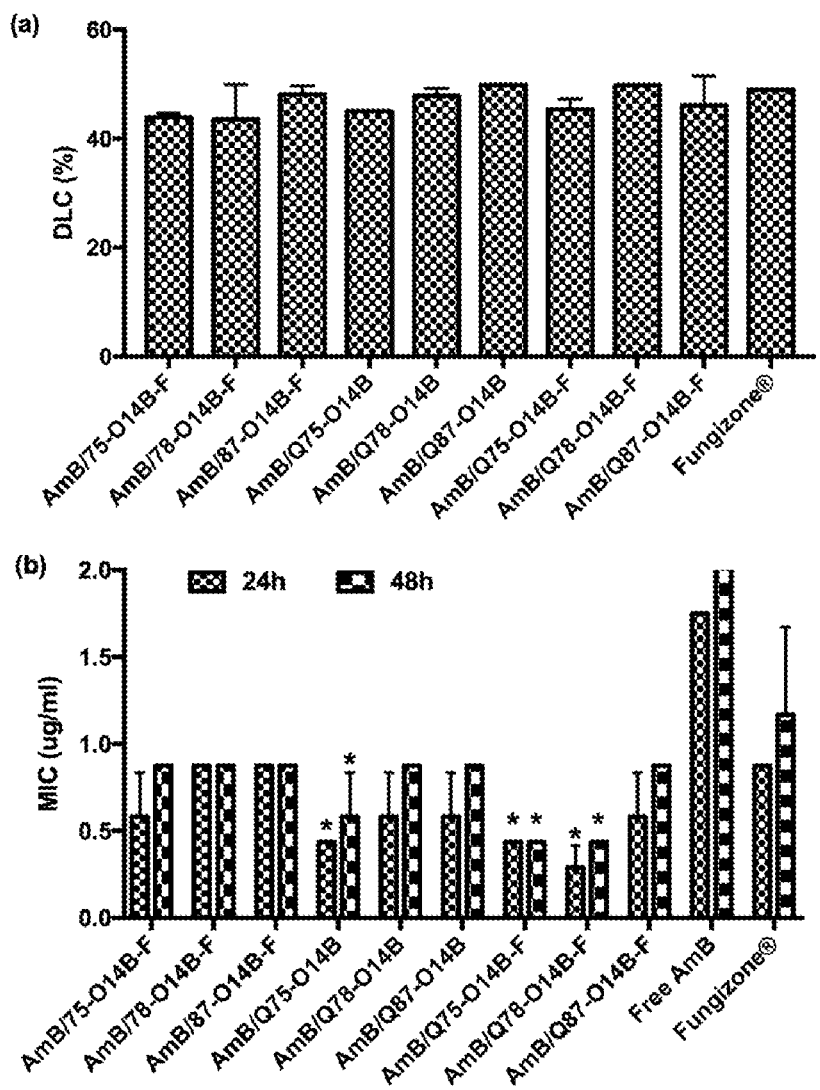
FIG. 21 shows (a) The DLC of AmB encapsulates and Fungizone® (n=3). (b) The MIC of different AmB encapsulates, free AmB and Fungizone® against Candida. albicans(SC5314) after 24 h and 48 h incubation from range of 14.0 to 0.109375 μg/mL (n=9), *P<0.05 vs Fungizone®.

AmB has high affinity to ergosterol in fungal cell membrane, leading to the pore formation, intercellular ion leakage and ultimately fungal cell death. The MIC test with 24 and 48 h incubation showed the lower MIC for the all AmB encapsulates when compared to free AmB and Fungizone® against yeast strains C. albicans (SC5314) (FIG. 21b). The MIC of Fungizone® was 0.875 µg/mL and free AmB was 1.75 µg/mL after 48 h incubation against C. albicans (FIG. 21b), consistent with the results obtained by Radwan. Among the all AmB encapsulates, AmB/Q78-O14B-F present the lowest MIC (0.29±0.13 µg/mL), which was almost 6-fold lower than free AmB, 3-fold lower than Fungizone® as shown in FIG. 21b ($p<0.05$). The structure characteristic of the quaternary amino group may contribute to the higher antifungal efficacy by increasing AmB concentrations in fungal cell membranes and the synergistic antifungal effect with AmB.

Example 18: Hemolysis Test from Human Erytrocytes (RBCs)

Figure 22:
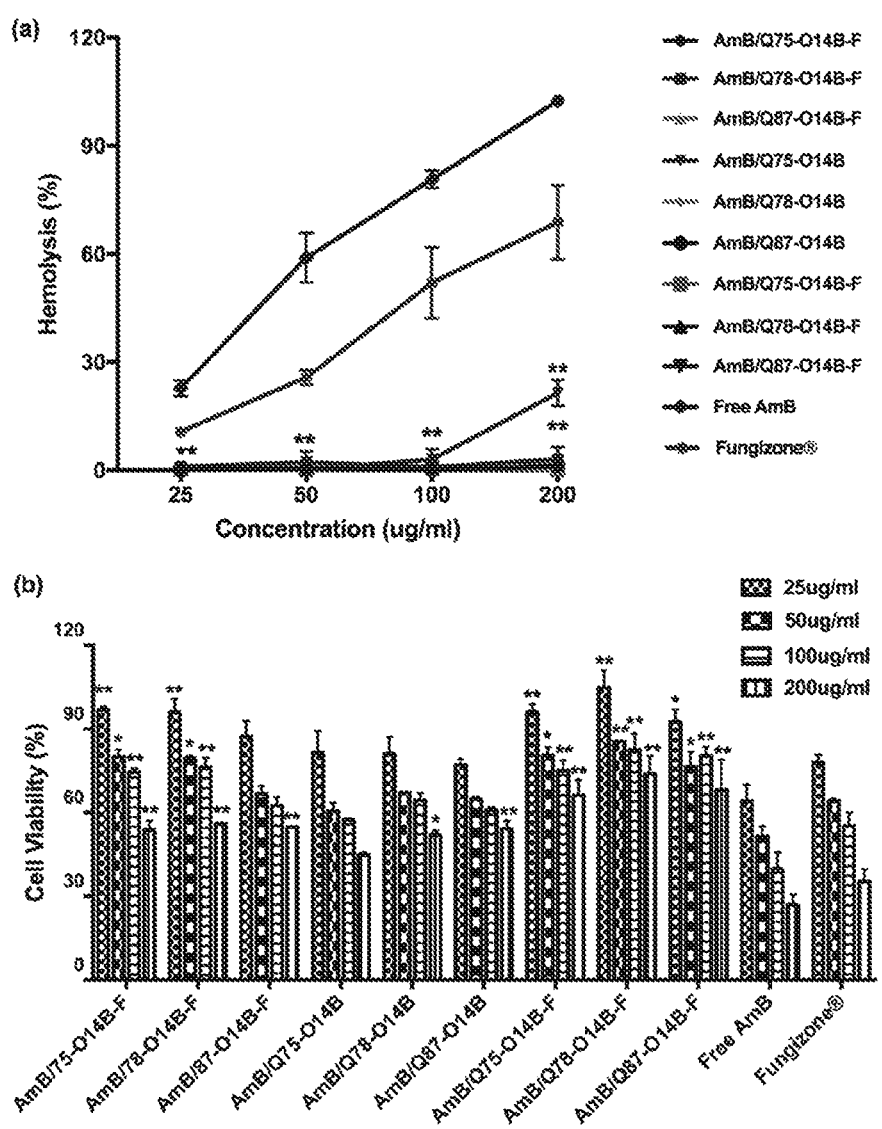
FIG. 22 shows (a) Hemolysis of human RBCs by AmB encapsulates, free AmB and Fungizone® at equivalent of AmB concentrations (25, 50, 100, 200 μg/mL) after 1 h incubation at 37° C.(n=9). (b) In vitro MTT test of different AmB encapsulates, free AmB and Fungizone® towards HEK293 cell line at equivalent of AmB concentrations (25, 50, 100, 200 μg/mL) after 24 h incubation. All data present as mean±SD (n=9), *p<0.05 and **p<0.001 vs Fungizone®

To evaluate the toxicity of AmB encapsulates, hemolysis induced by different concentrations of AmB were compared with free AmB and Fungizone®. Free AmB exhibited almost 80.69±2.39% and 102.47±1.04% of hemolysis at 100 and 200 µg AmB/mL, respectively (FIG. 22a). Fungizone® showed almost 52.05±9.83% and 68.84±10.28% of hemolysis at the same concentration of AmB. The hemolytic properties of AmB encapsulates were little affected up to 200 µg AmB/mL except AmB/Q75-O14B-F encapsulates which exhibit 21.39±3.58% at 200 µg AmB/mL as shown in FIG. 22a ($p<0.05$). Therefore, AmB encapsulates were less hematotoxic than Fungizone®, because AmB released from bilayer unilamellar was lower than from micellar formulation. The micelles of Fungizone® are a relatively weak barrier compared to lipid bilayers and the drug in Fungizone® is more available than AmB encapsulates, resulting in faster leakage of hemoglobin and potassium. Another reason for increased of hemolysis for Fungizone® is that the component of sodium deoxycholate which acts as a surfactant can induce hemolysis itself.

Example 19: In Vitro Toxicity in Mammalian Cells

FIG. 22b showed the cell viabilities of AmB encapsulates, Fungizone® and free AmB at concentrations ranging from 25 to 200 µg AmB/mL. Free AmB and Fungizone® showed obvious cytotoxicity to HEK293 only after 24 h incubation even at low concentration. After formulated with the QLDs, the cell viabilities of AmB/(Q75-O14B, Q78-O14B, Q87-O14B) encapsulates were slight decreased compared to AmB/(75-O14B, 78-O14B 87-O14B)—F encapsulates. Simultaneously, the cell viability of all AmB nanoparticles dramatically increased when compared to Fungizone® and free AmB ($p<0.05$). After formulated with DSPE-PEG, the cell viabilities of AmB/(Q75-O14B, Q78-O14B, Q87-O14B)—F encapsulates remained at 70-80% up to 200 µg AmB/mL. This perhaps contributed to biocompatible and relatively nontoxic DSPE-PEG which is capable of interacting with the positive amino group of AmB to form an ionic complex in the bilayers. Another reason is that QLDs effectively encapsulated AmB resulting in slow and sustained AmB release and reducing the toxicity.

Based on the results from the in vitro evaluation, the AmB/Q78-O14B-F demonstrating minimally toxicity, MIC and most stability was finally screened to be the most effective delivery system for further analysis in vivo.

Example 20: Pharmacokinetics Analysis Studies

Pharmacokinetics impact the accumulation of the drug in the tissues. AmB/Q78-O14B-F and Fungizone® were intravenously injected into rats at a dose of 2 mg AmB/kg body weight for comparison of their pharmacokinetic profiles. The estimated plasma concentration-versus-time profiles were shown in FIG. 23a and corresponding mean pharmacokinetic parameters were summarized in Table 1.

The results demonstrated that plasma concentration profiles of both AmB/Q78-O14B-F and Fungizone® showed a rapid initial distributive phase. Meanwhile, AmB/Q78-O14B-F yielded higher maximal plasma concentration (Cmax) for AmB than Fungizone® (25.13±7.05 and 2.66±0.81 µg/mL, respectively, $p<0.05$) (Table 1). The AmB concentration of Fungizone® could not detectable in all rats at 24 h and in one rat at 12 h. The AmB was still detectable at 24 h (0.74±0.12 µg/mL) after administration and remain above the MIC (0.39±0.13 µg/mL). AmB would show fungistatic activity if the concentration is less than 0.5 to 1-fold MIC and perform strong fungicidal activity when its concentration is more than 0.5 to 1 time of the MIC. The results indicated that AmB/Q78-O14B-F still have fungicidal activity after 24 h administration beneficial for blood-borne infection such as disseminated candidiasis.

Moreover, AmB/Q78-O14B-F showed higher AUC (46.58±6.28 mg*h/L) over 4-fold against that of Fungizone® (10.98±5.02 mg*h/L) and the smaller volume of distribution (Vd) (177.08±46.05 L/kg) almost half against that of Fungizone® (296.86±12.02 I/kg) ($p<0.05$) (Table 1). The pharmacokinetic behavior of AmB/Q78-O14B-F seems to be similar to Ambisome® which also exhibits a high Cmax, AUC, slow CI and small Vd. One explanation is that amino group of AmB, with its positive charge forms an ionic complex with QLDs. This mechanism thereby promotes the retention of AmB within the liposomal bilayer and released it slowly, resulting in a longer circulation in blood. Another reason is DSPE-PEG possesses properties of its biocompatibility and varied conformational flexibility which prolongs blood circulation time by being attaching on the surface of anionic lipids and thus further facilitates the retention of AmB within bilayer.

It is very important to avoid the uptake by RES and prolong the plasma circulation time to improve the distribution and effect when the infected target is a tissue except for liver and spleen. Fungizone® displayed low AUC, Cmax, large CI and wide Vd (Table 1) consistent with previously reported results. The low AmB plasma concentration of Fungizone® could be explained by the fast release of AmB from micellar formulation of Fungizone® and high uptake of AmB by RES of the liver and spleen. We also observed an interesting phenomenon that Fungizone® displayed a second peak in plasma levels 4 h after administration which have already been reported respectively before by Swenson and Serrano (FIG. 6a). This may be related to the redistribution from the tissues such as liver.

TABLE 1

Pharmacokinetic parameters of AmB after intravenous injection of AmB/Q78-O14B-F and Fungizone ® in rats at a dose of 2 mg AmB/kg.

| Parameters | Fungizone ® | AmB/Q78-O14B-F |
|---|---|---|
| Dose (mg/kg) | 2 | 2 |
| $AUC_{0-24}$ (mg*h/L) | 10.98 ± 5.02 | 46.58 ± 6.28* |
| MRT (h) | 27.92 ± 32.0 | 21.87 ± 5.48 |
| $C_{max}$ (mg/L) | 2.66 ± 0.81 | 25.13 ± 7.05** |
| $T_{1/2}$ (h) | 19.11 ± 22.94 | 21.14 ± 6.91 |
| CL (L/Kg/h) | 19.04 ± 12.02 | 5.93 ± 0.98* |
| Vd (L/Kg) | 296.86 ± 159.06 | 177.08 ± 46.5* |

Note.
All data represent as mean ± SD(n = 3).
Abbreviations:
AUC Area under the concentration time curve;
MRT Mean Residence Time,
Cmax Maximal plasma concentration,
$T_{1/2}$ half-life,
CL clearance,
V volume of distribution,
*p <0.05 and
**p <0.001 vs Fungizone ®.

Example 21: Tissue Biodistribution Test

Once the nanoparticles leave blood circulation, it is very important to know where the drug goes and how long it remains in a particular tissue, because tissues are also the primary site of systemic fungal infection. The results of tissues distribution after 48 h and 72 h intravenous administration were shown in FIG. 23b-23e. All the mice were alive when administrated with AmB/Q78-O14B-F at a single dose of equivalent of AmB 5 mg/kg and 2 mg/kg. Each group has one deceased mouse when administrated with the dose equivalent to AmB 10 mg/kg of AmB/Q78-O14B-F and 2 mg/kg of Fungizone®

Figure 23:
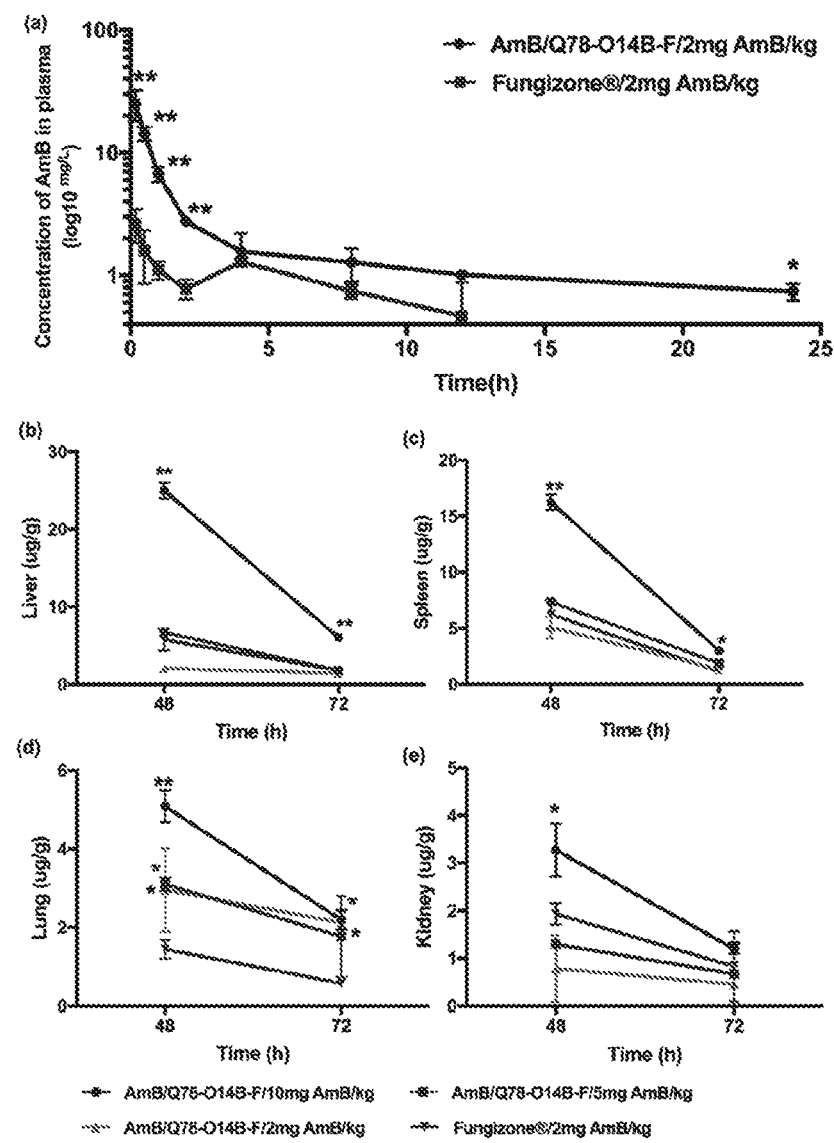
FIG. 23 shows (a) Plasma concentrations of AmB after intravenous injection of AmB/Q78-O14B-F and Fungizone® at a dose of 2 mg AmB/kg to SD rats; (b-e) The AmB concentrations in mice tissues after 48 h and 72 h intravenous treatment of AmB/Q78-O14B-F (10 mg, 5 mg, 2 mg AmB/kg, respectively) and Fungizone® (2 mg AmB/kg) by HPLC, (b) Liver, (c) Spleen, (d) Lung, (e) Kidney, *p<0.05 and **p<0.001 vs Fungizone®.

The results indicated that AmB/Q78-O14B-F exhibited lower concentrations in liver (2.07±0.30 µg/g) and spleen (5.10±0.97 µg/g) compared to that of Fungizone® (5.80±1.43 µg/mL in liver and 6.25±1.30 µg/mL in spleen) after 48 h injection at a single dose of 2 mg AmB/kg (FIGS. 23b and 23c). Because AmB/Q78-O14B-F avoided been immediate recognized by RES leading to prolonged circulation in plasma. The recognition of particle is mediate by opsonization in blood, depending on the distance between the particle and opsonins. When the distance is short like Fungizone®, opsonins bind to the surface of the particle then are recognizable by RES. Furthermore, the AmB concentration of AmB/Q78-O14B-F decline to the equivalent level in liver (1.46±0.06 g/g) and spleen (1.37±0.06 µg/g) in comparison to Fungizone® (1.80±0.10 and 1.23±0.14 µg/mL, respectively) after 72 h injection, and still remain above the MIC (FIGS. 23b and 23c). The long-term tissue retention suggests that the drug could be given intermittently, instead of daily, without losing efficacy and this would reduce the cost and possible toxic side-effects. Unfortunately, AmB/Q78-O14B-F exhibited none AmB distribution in brain tissue, which was not beneficial for the intracranial fungal infection such as cryptococcal meningitis.

We noticed that the AmB concentrations were low in kidneys (48 h, 0.79-0.70 µg/g, 72 h, 0.45±0.39 µg/g) as compared with Fungizone® (48 h, 1.93±0.23 µg/g; 72 h, 0.83±0.74 g/g)(FIG. 23e), indicating reduced distributions of AmB to kidneys. The explanation is that liposome is large enough to avoid glomerular filtration and drug renal excretion and led to reduced nephrotoxicity of AmB encapsulates.

There was another superior attribute of this nanoparticle that AmB/Q78-O14B-F accumulates in the lungs at higher concentrations than Fungizone® (2.96±1.06 vs 1.45±0.24 µg/g, respectively, p<0.05) (FIG. 23d). After 72 h injection, the concentration in lung of AmB encapsulates was 2.12±0.27 g/g, however, low AmB concentrations were detectable in the lungs of Fungizone® treated mice (p<0.05) (FIG. 23d). It is beneficial for pulmonary fungal infection when the target of AmB/Q78-O14B-F is lung site such as invasive aspergillosis. Unfortunately, AmB/Q78-O14B-F did not exhibit any distribution in brain tissues, which was not beneficial for the intracranial fungal infection such as cryptococcal meningitis.

An increase in the dose-dependent response was noted in the tissues of AmB/Q78-O14B-F treated mice (FIG. 23b-23e). When the injection dose was increased to 5 mg AmB/Kg, higher concentrations were detected in all organ tissues of mice. All mice were survived in the experiment, no toxicities were identified in subsequent in vivo toxicity test. However, one mouse died in 12 h when the dose of AmB/Q78-O14B-F was increased to 10 mg AmB/kg. It means the toxicity increased when higher concentration of AmB accumulated in the tissues post administration. Low concentrations of AmB were found in heart tissues after 48 h administration at a dose of 10 mg AmB/kg. One mouse succumbed to Fungizone® at the single dose of 2 mg Amb/kg intravenous administration. These results indicated AmB/Q78-O14B-F have wider and safer therapeutic window as compared with Fungizone®, which was confirmed in following in vivo toxicity test.

Example 22: In Vivo Toxicity Tests

Figure 24:
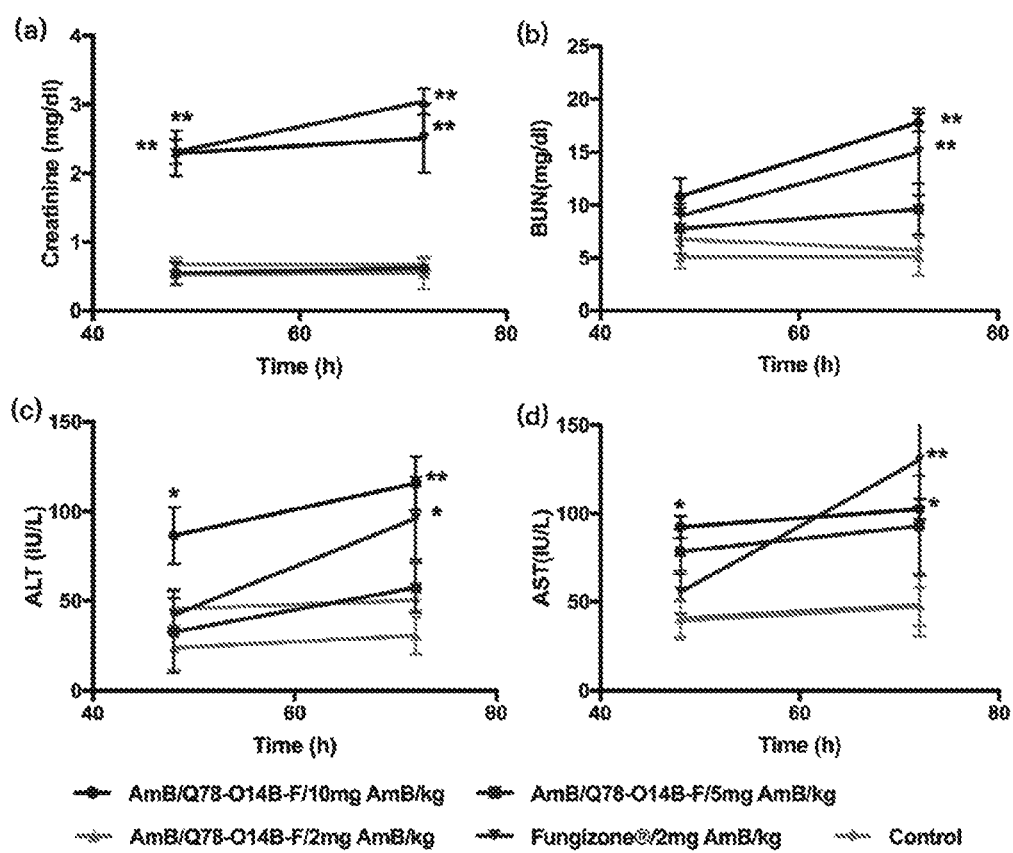
FIG. 24 shows the In vivo toxicity of (a) Creatinine, (b) BUN, (c) ALT, (d) AST level in healthy BALB/c mice 48 h and 72 h after intravenous administrated with AmB/Q78-O14B-F at dose of 10 mg, 5 mg and 2 mg AmB/kg and Fungizone® at dose of 2 mg AmB/kg (n=3), *p<0.05 and **p<0.001 vs Fungizone®.

In vivo toxicity evaluations, the results suggested AmB/Q78-O14B-F did not affect liver (ALT and AST) and kidney (Cr and BUN) functions at the dose of either 2 mg or 5 mg AmB/kg treated mice compared to that of the control group (FIG. 24). The results were consistent with the reduction of AmB concentration accumulation in kidneys of 2 mg or 5 mg AmB/kg of AmB/Q78-O14B-F treated mice (FIG. 23e). Thus, glomerular filtration is reduced and nephrotoxicity is minimized. However, AmB/Q78-O14B-F increased the Cr and BUN level or the liver enzymes AST and ALT when the dose was elevated to 10 mg AmB/kg and all have significant differences compared with that of the control group (p<0.05) (FIG. 24).

The hepatotoxicity and nephrotoxicity may relate to the AmB retention in kidney and liver after increasing dose administration. In comparison, Fungizone® induced significant increases in Cr, BUN, ALT and AST after 72 h administration at similar dose of 2 mg AmB/kg when compared to AmB/Q78-O14B-F (p<0.05) (FIG. 24). The findings demonstrated that AmB/Q78-O14B-F present a substantial reduction in toxicity and an increase in the therapeutic window of AmB in comparison to Fungizone®.

Example 23: Lipids with Fluorine Chains

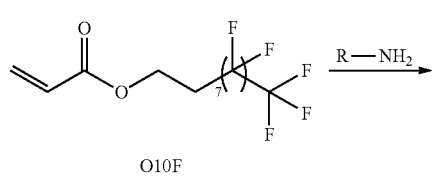

O10F

-continued

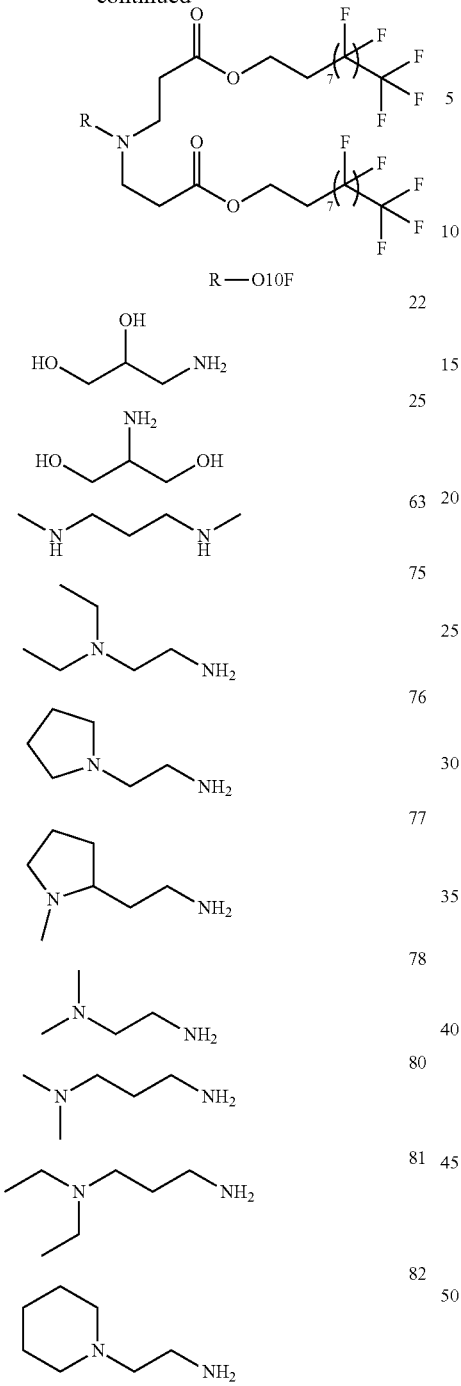

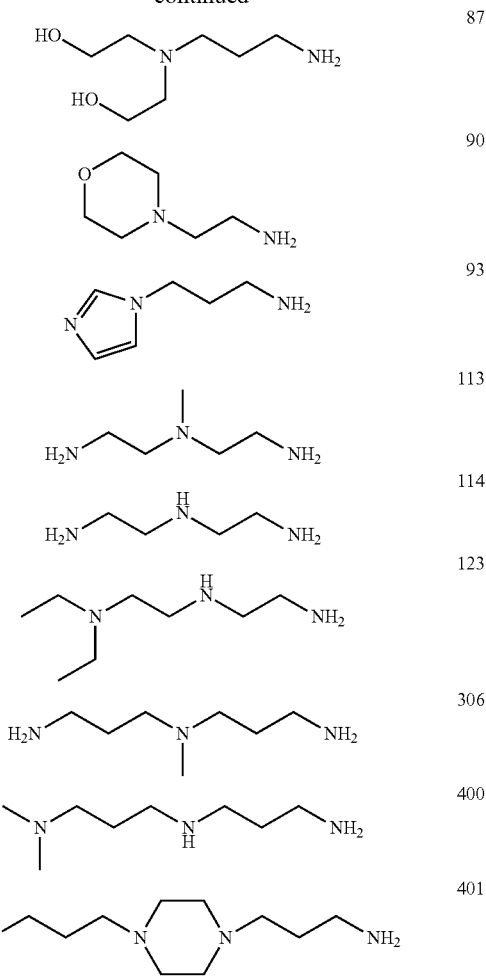

Synthesis

A fluorine-containing tail (2.5 equiv.) was mixed with an amine head (1 equiv.) in a clean glass vial. The mixture was kept under 70 C with continuous stirring for 48 h. The reaction was then stopped, and the crude product was purified via silica gel column chromatography, using methanol and dichloromethane as the mobile phase.

Assay

Figure 25:
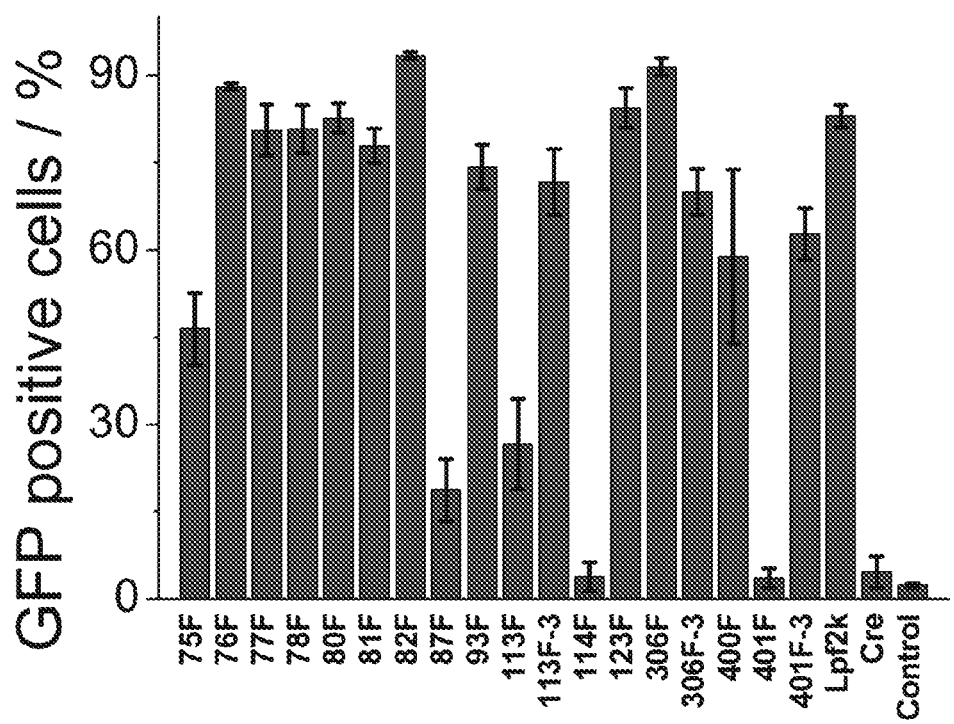
FIG. 25 is a bar graph showing the percentage of GFP positive cells (GFP+) as a function of the fluorine-containing lipidoid used for protein delivery.
Figure 26:
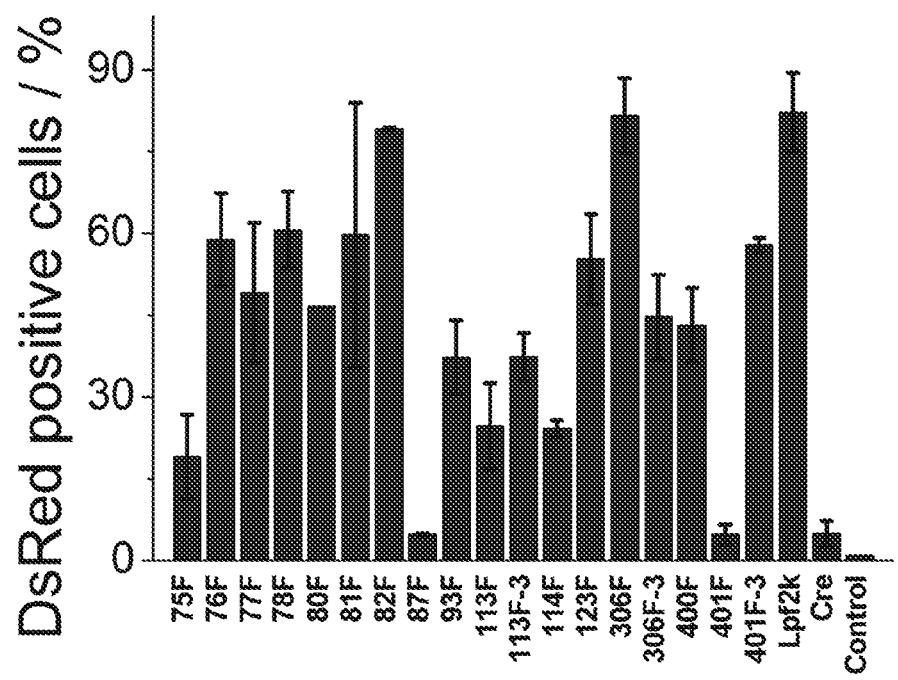
FIG. 26 is a bar graph showing the percentage of DsRed positive cells as a function of the fluorine-containing lipidoid used for protein delivery.

The results of the percentage of GFP positive and DsRed positive cells for the above different lipids with fluorine chain are summarized in a bar graph in FIG. 25 and FIG. 26.

Example 24: New Library 1—Amine 200 with Different Hydrophobic Tails

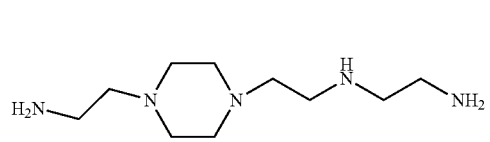

Molecular Weight: 215.35

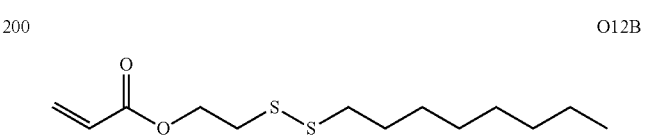

Molecular Weight: 276.45

-continued

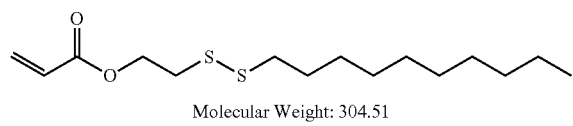
O14B
Molecular Weight: 304.51

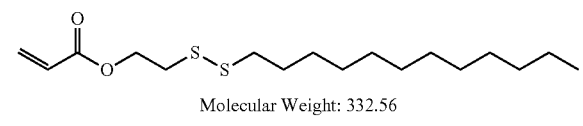
O16B
Molecular Weight: 332.56

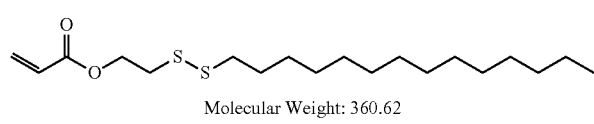
O18B
Molecular Weight: 360.62

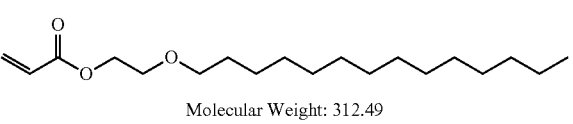
O14
Molecular Weight: 312.49

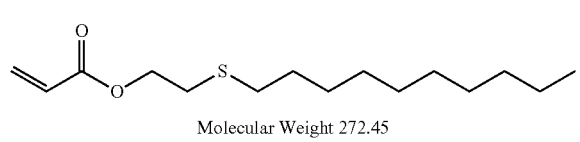
S10
Molecular Weight 272.45

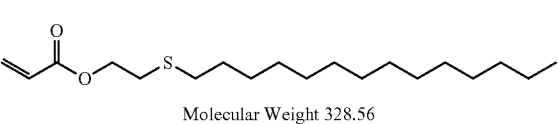
S14
Molecular Weight 328.56

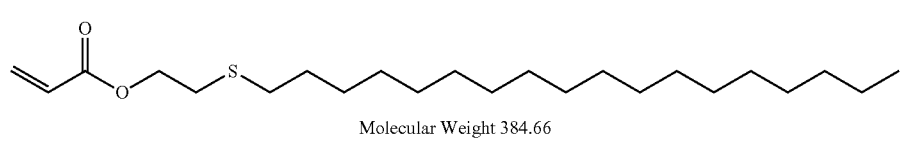
S18
Molecular Weight 384.66

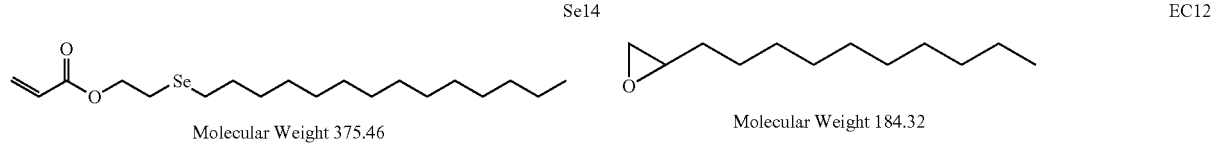
Se14
Molecular Weight 375.46

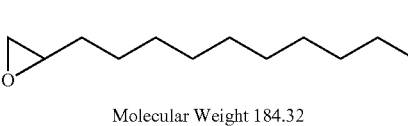
EC12
Molecular Weight 184.32

Figure 27:
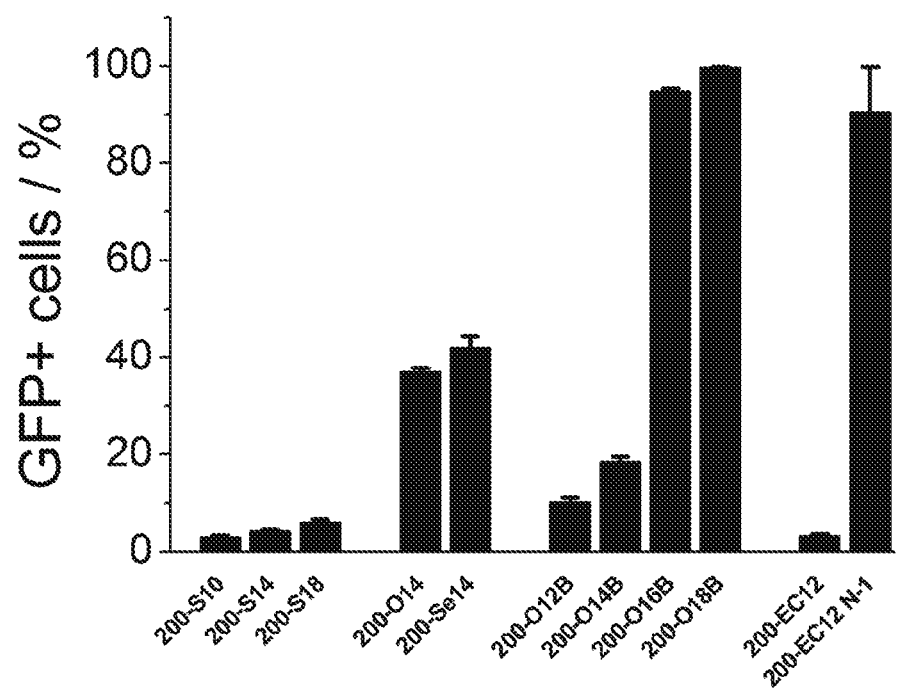
FIG. 27 is a bar graph showing the percentage of GFP+ cells as a function of the lipidoid (derived from lipids with different hydrophobic tails and synthesized from amine 200) used for protein delivery.

The results of the percentage of GFP+ cells for the above lipids with different hydrophobic tails (synthesized from amine 200) are summarized in a bar graph in FIG. 27.

Example 25: New Library 2—Cyclic Amine Analogues

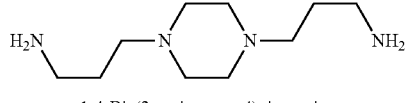
1,4-Bis(3-aminopropyl)piperazine

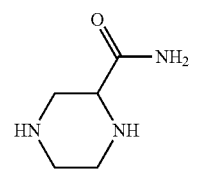
piperazine-2-carboxamide

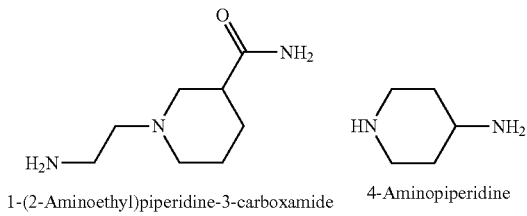
1-(2-Aminoethyl)piperidine-3-carboxamide    4-Aminopiperidine

-continued

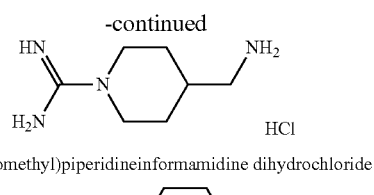
4-(aminomethyl)piperidineinformamidine dihydrochloride

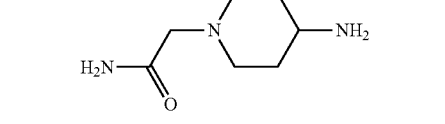
2-(4-aminopiperidin-1-yl)acetamide

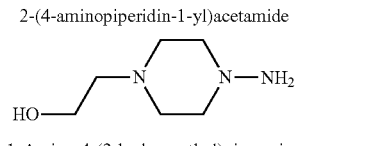
1-Amino-4-(2-hydroxyethyl)piperazine

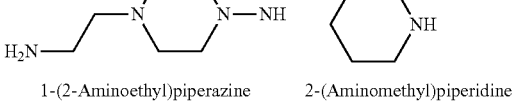
1-(2-Aminoethyl)piperazine    2-(Aminomethyl)piperidine

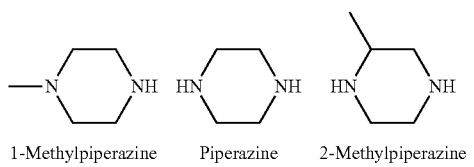
1-Methylpiperazine    Piperazine    2-Methylpiperazine

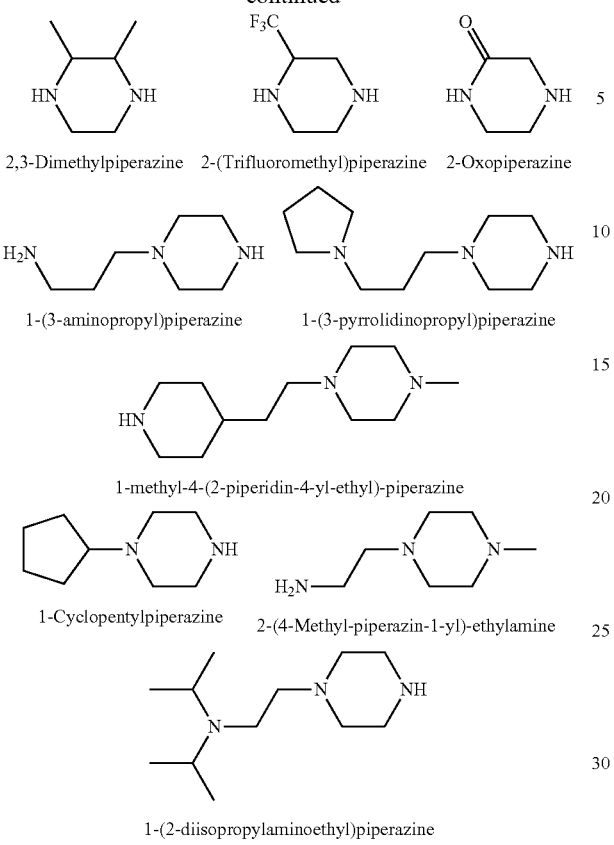

Figure 28:
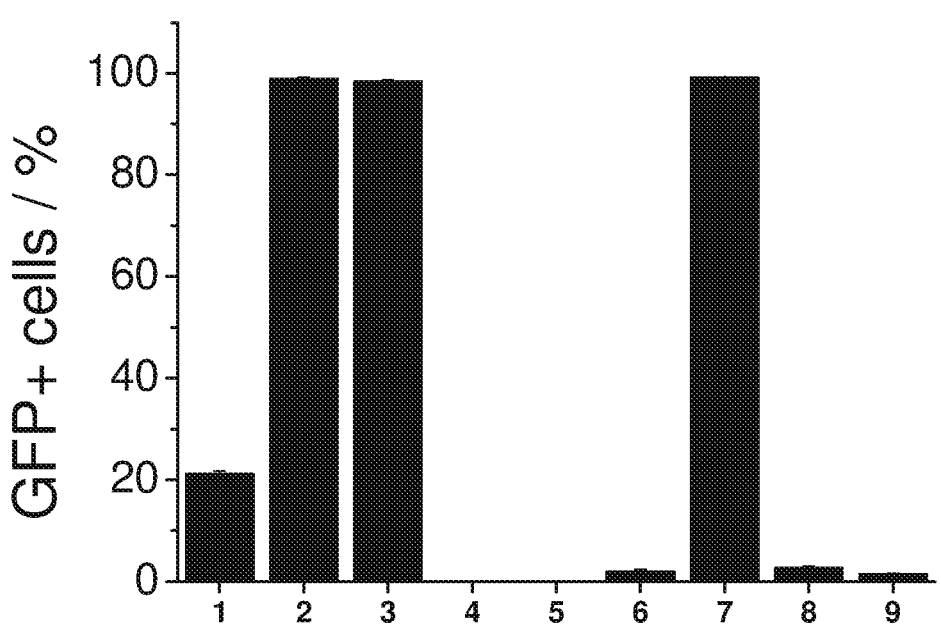

2,3-Dimethylpiperazine   2-(Trifluoromethyl)piperazine   2-Oxopiperazine 1-(3-aminopropyl)piperazine   1-(3-pyrrolidinopropyl)piperazine 1-methyl-4-(2-piperidin-4-yl-ethyl)-piperazine 1-Cyclopentylpiperazine   2-(4-Methyl-piperazin-1-yl)-ethylamine 1-(2-diisopropylaminoethyl)piperazine The results of the percentage of GFP+ cells for lipids synthesized from different cyclic amine analogues are summarized in a bar graph in FIG. 28.

Example 26: New Library 3—Imidazole Containing Amine Analogues

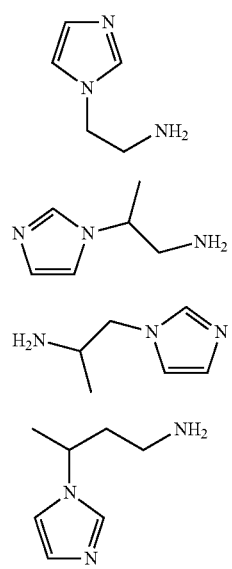

9310

9311

9312

9313

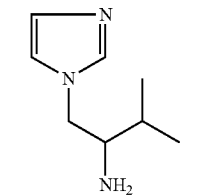

9314

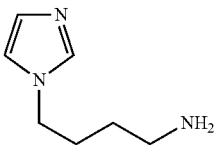

9315

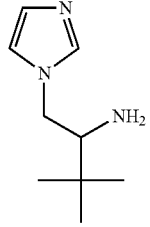

9316

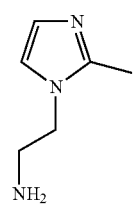

9321

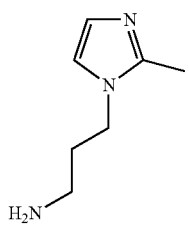

9322

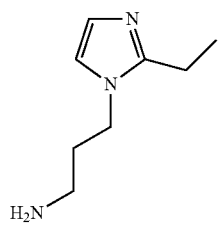

9323

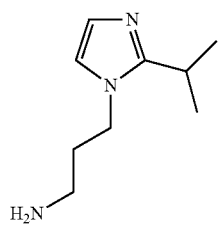

9324

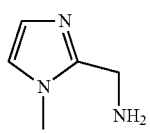

9331

-continued

9332
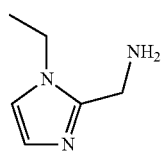

9333
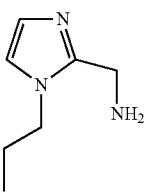

9334
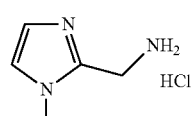

9341
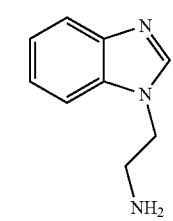

9351
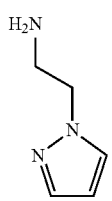

9352
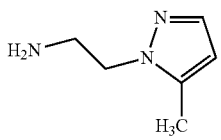

9361
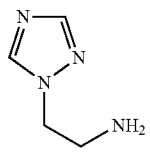

Figure 29:
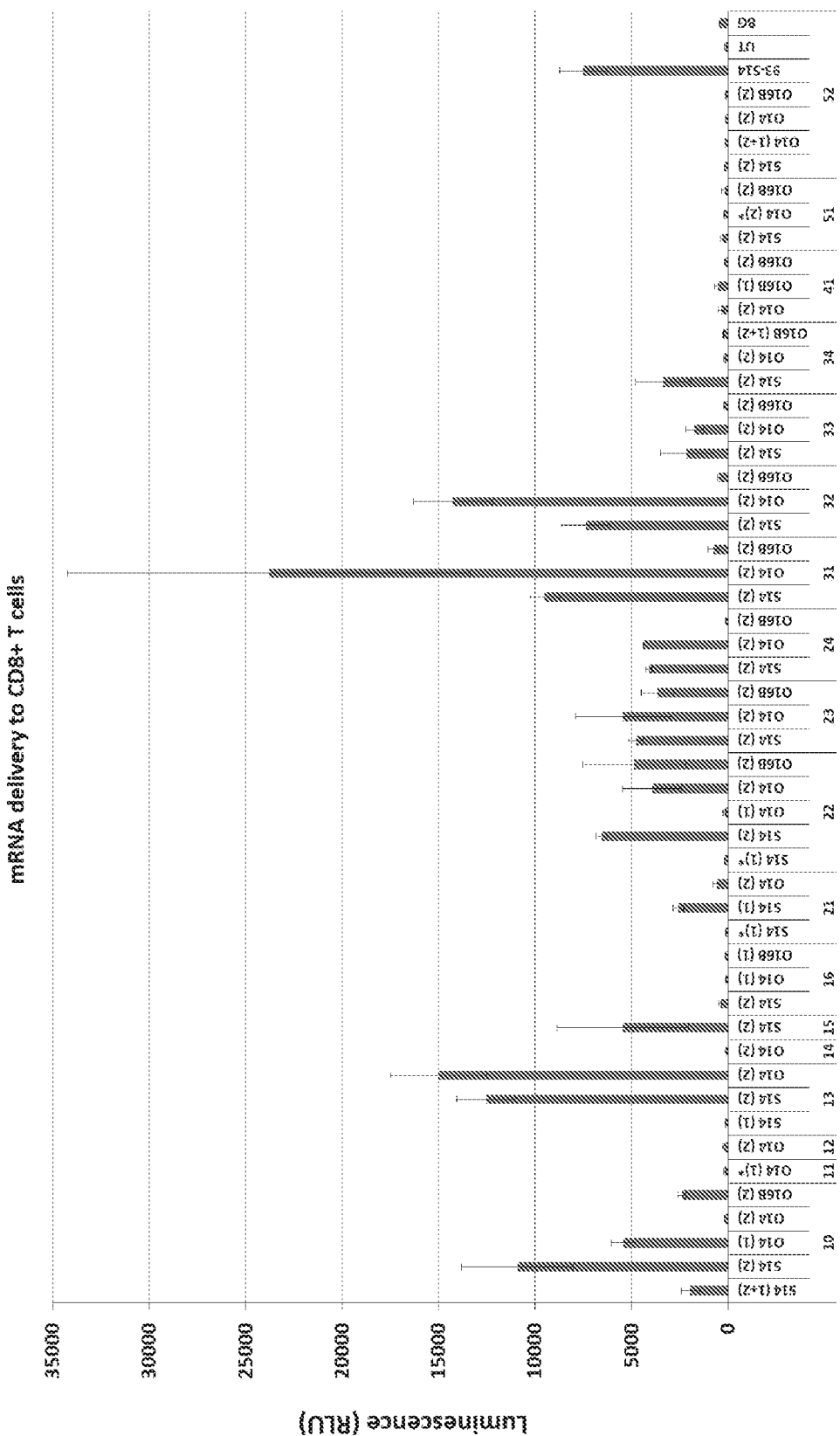
FIG. 29 is a bar graph showing the observed luminescence stemming from mRNA delivery to CD8+ T cells as a function of the lipidoid (derived from lipids synthesized from different imidazole-containing amine analogues).

The results of the efficiency of mRNA delivery to CD8+ T cells for the above lipids synthesized from different imidazole-containing amine analogues are summarized in a bar graph in FIG. 29.

Additional Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims. It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A compound having a structure represented by Formula (I):

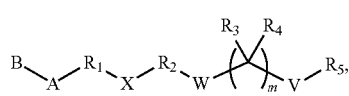

(I)

or a pharmaceutically acceptable salt thereof,
wherein
A, a hydrophilic head, is selected from:

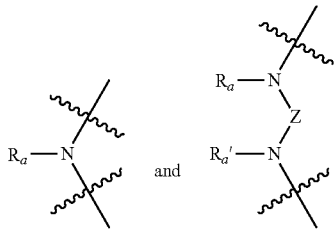

wherein:
$R_a$ and $R_a'$ are each independently selected from H, $C_1$-$C_{20}$ alkyl, $C_3$-$C_{20}$ cycloalkyl, $C_1$-$C_{20}$ heteroalkyl, $C_1$-$C_{20}$ heterocycloalkyl, $C_6$ monocyclic aryl, and 5-8 monocyclic heteroaryl; and
Z is selected from a $C_1$-$C_{20}$ bivalent aliphatic radical and a $C_1$-$C_{20}$ bivalent heteroaliphatic radical;
B is

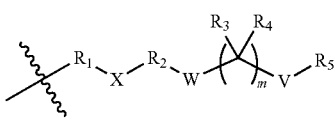

wherein
$R_1$ and $R_2$ are each independently at each occurrence a $C_1$-$C_{20}$ bivalent aliphatic radical;
$R_3$ and $R_4$ are each independently at each occurrence selected from H and $C_1$-$C_{10}$ alkyl; or, alternatively, $R_3$ and $R_4$, together with the atom to which they are attached, form $C_3$-$C_{10}$ cycloalkyl;
$R_5$ is independently at each occurrence selected from $C_1$-$C_{24}$ alkyl, $C_2$-$C_{24}$ alkenyl, $C_2$-$C_{24}$ alkynyl, $C_3$-$C_{24}$ cycloalkyl, $C_1$-$C_{24}$ heteroalkyl, $C_1$-$C_{24}$ heterocycloalkyl, aryl, and heteroaryl;
W is independently at each occurrence selected from O, S, and Se;
V is independently at each occurrence selected from a bond, O, S, and Se;
X is independently at each occurrence selected from

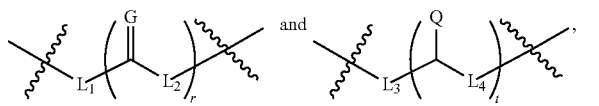

wherein:
  $L_1$, $L_2$, $L_3$, and $L_4$ are each independently at each occurrence selected from a bond, O, S, and $NR_c$;
  G is independently at each occurrence selected from O, S, and $NR_d$;
  Q is independently at each occurrence selected from $OR_f$, $SR_g$, and $NR_hR_i$;
  r and t are each independently at each occurrence an integer from 1 to 6;
  wherein $R_c$, $R_d$, $R_f$, $R_g$, $R_h$, and $R_i$ are each independently at each occurrence selected from H, $C_1$-$C_{10}$ alkyl, $C_1$-$C_{10}$ heteroalkyl, aryl, and heteroaryl; and
m is 1; and
at least one of W and V is Se.

2. The compound or the pharmaceutically acceptable salt thereof of claim 1, wherein one and only one of W and V is Se.

3. The compound or the pharmaceutically acceptable salt thereof of claim 1, wherein W is Se; and V is a bond.

4. The compound or the pharmaceutically acceptable salt thereof of claim 1, wherein W is at each occurrence Se.

5. The compound or the pharmaceutically acceptable salt thereof of claim 4, wherein V is at each occurrence a bond.

6. The compound or the pharmaceutically acceptable salt thereof of claim 1, wherein, in B, X is selected from

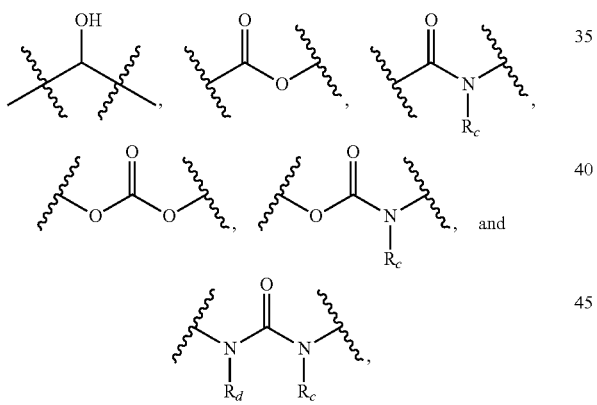

wherein $R_c$ and $R_d$ are each independently at each occurrence selected from H, $C_1$-$C_{10}$ alkyl, $C_1$-$C_{10}$ heteroalkyl, aryl, and heteroaryl.

7. The compound or the pharmaceutically acceptable salt thereof of claim 6, wherein $R_c$ and $R_d$ are each independently at each occurrence selected from H and $C_1$-$C_{10}$ alkyl.

8. The compound or the pharmaceutically acceptable salt thereof of claim 1, wherein $R_1$ and $R_2$ are each independently at each occurrence a $C_1$-$C_4$ bivalent aliphatic radical.

9. The compound or the pharmaceutically acceptable salt thereof of claim 1, wherein $R_3$ and $R_4$ are each independently at each occurrence selected from H and $C_1$-$C_4$ alkyl.

10. The compound or the pharmaceutically acceptable salt thereof of claim 1, wherein $R_5$ is $C_1$-$C_{20}$ alkyl.

11. The compound or the pharmaceutically acceptable salt thereof of claim 1, wherein A is an amino moiety formed from one of the following amines:

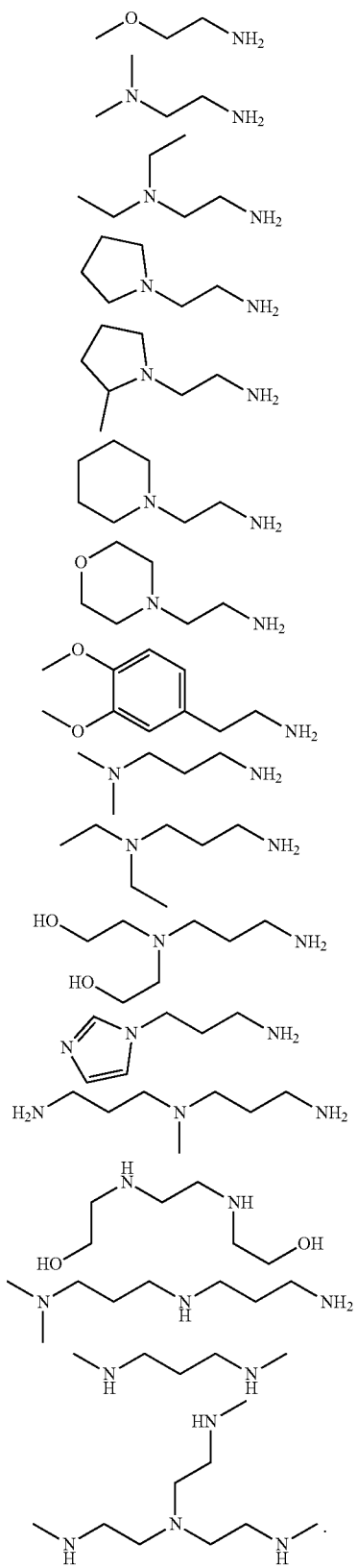

12. The compound or the pharmaceutically acceptable salt thereof of claim 1, wherein A is an amino moiety formed from one of the following amines:

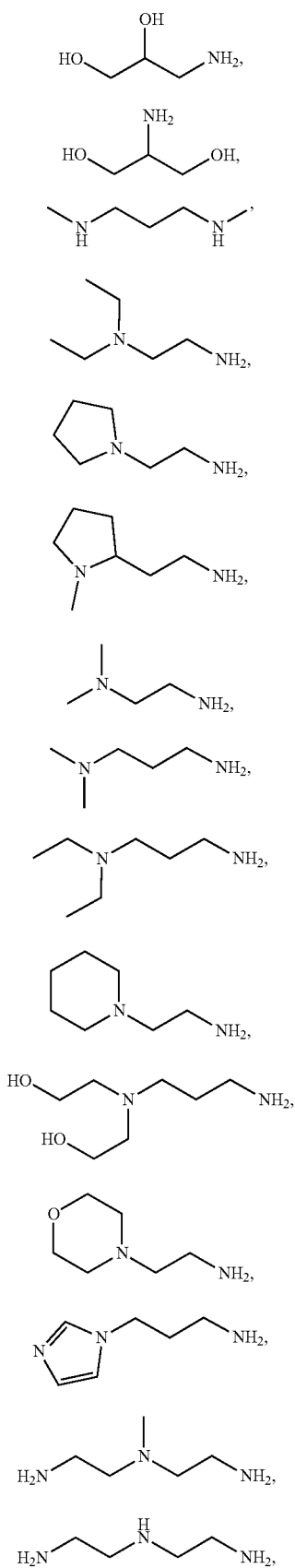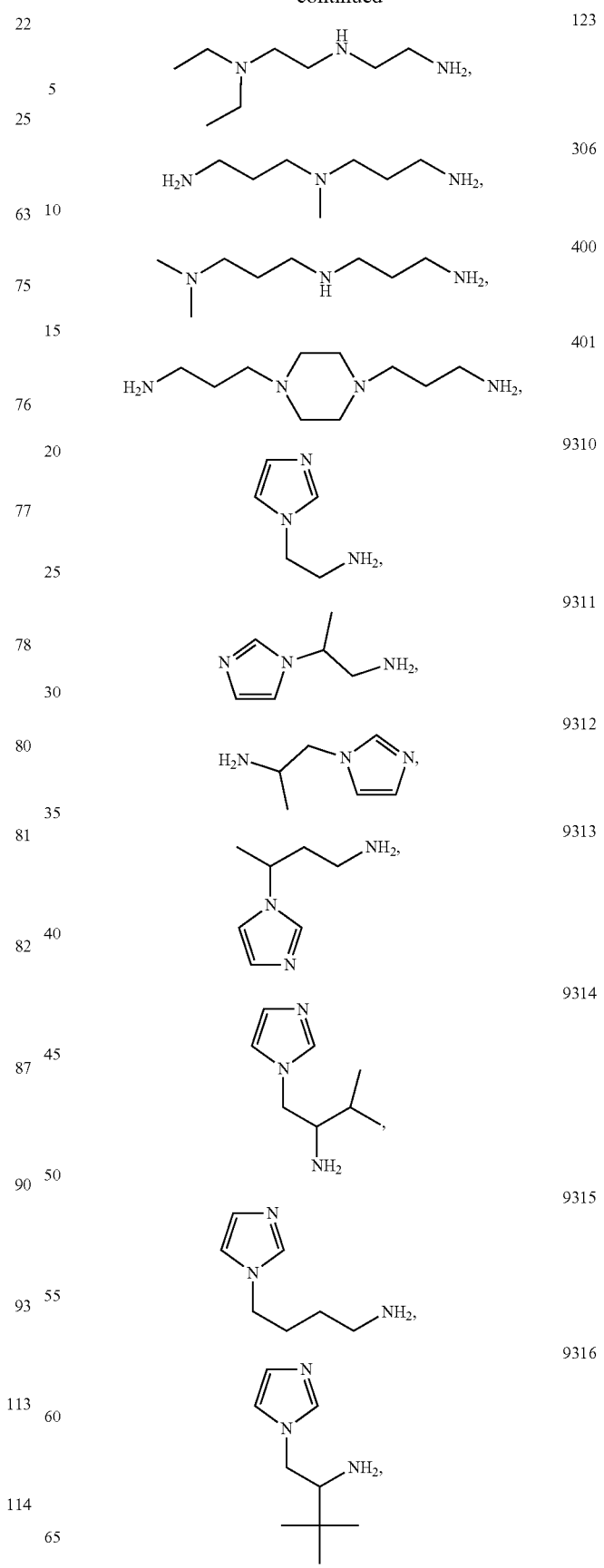

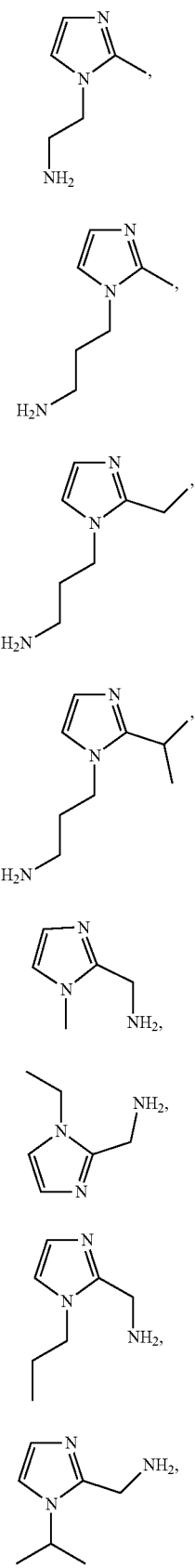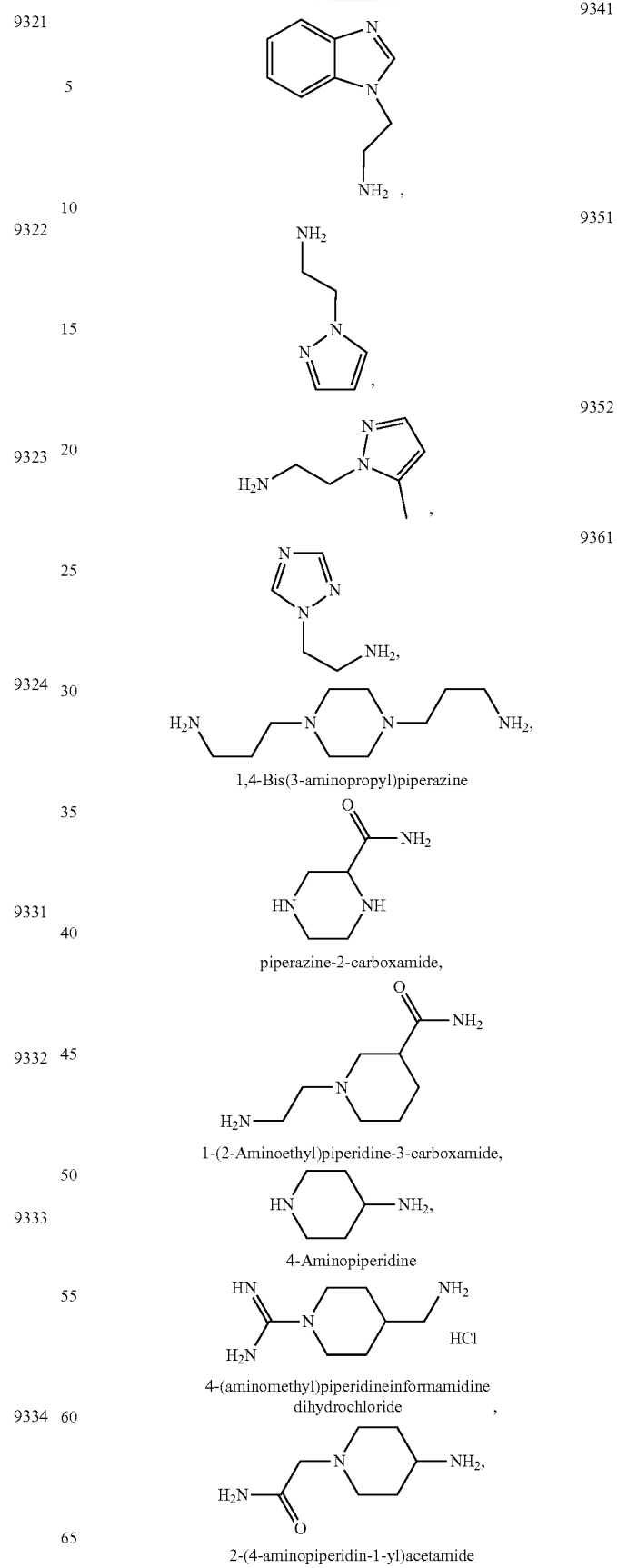

-continued

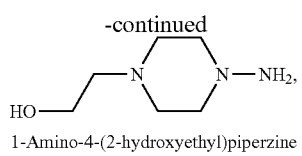
1-Amino-4-(2-hydroxyethyl)piperzine

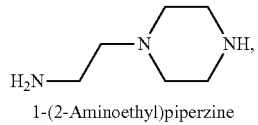
1-(2-Aminoethyl)piperzine

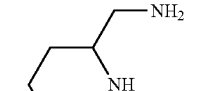
2-(Aminoethyl)piperidine,

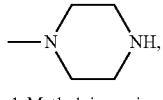
1-Methylpiperazine

Piperazine

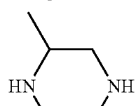
2-Methylpiperazine,

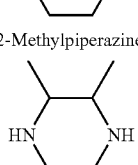
2,3-Dimethylpiperazine,

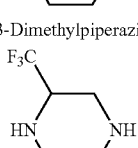
2-(Trifluoromethyl)piperazine,

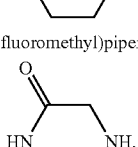
2-Oxopiperazine

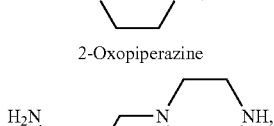
1-(3-aminopropyl)piperazine

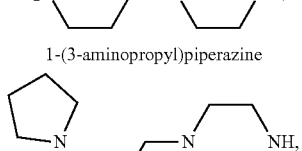
1-(3-pyrrolidinopropyl)piperazine

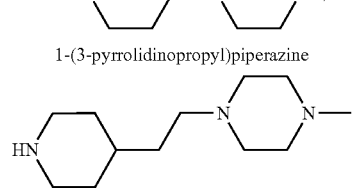
1-methyl-4-(2-piperidin-4-yl-ethyl)-piperazine,

-continued

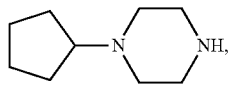
1-Cyclopentylpiperazine

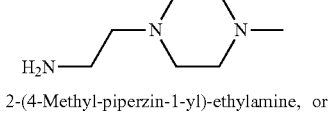
2-(4-Methyl-piperzin-1-yl)-ethylamine, or

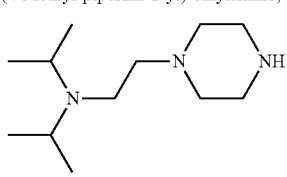
1-(2-diisopropylaminoethyl)piperazine.

13. A pharmaceutical composition, comprising the compound or the pharmaceutically acceptable salt thereof of claim 1; and a therapeutic agent.

14. The pharmaceutical composition of claim 13, wherein the therapeutic agent comprises a protein or a nucleic acid.

15. The compound or the pharmaceutically acceptable salt thereof of claim 1, wherein A is an amino moiety formed from one of the following amines:

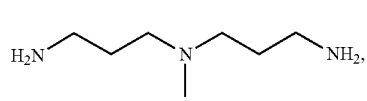
306

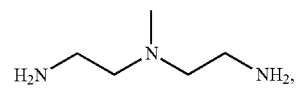
113

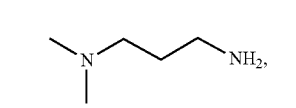
80

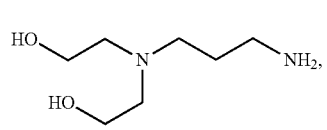
87

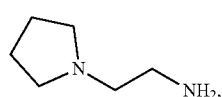
76

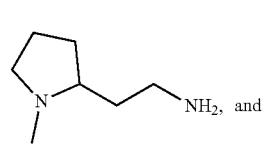
77

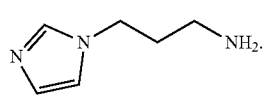
93

16. The compound or the pharmaceutically acceptable salt thereof of claim 1, wherein the compound is

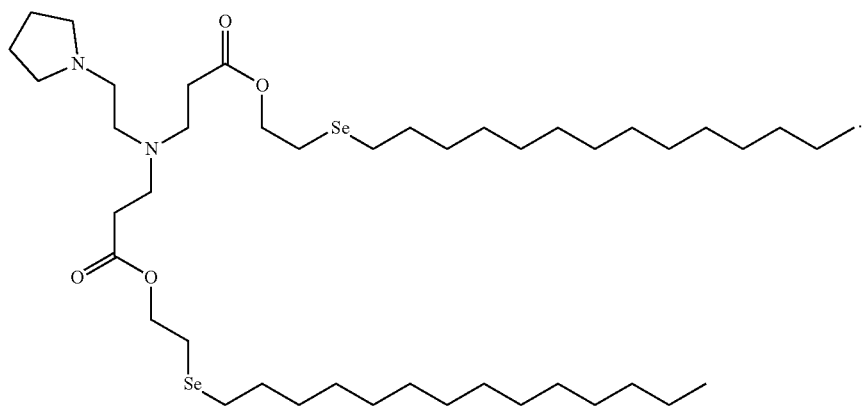 [SMILES: CCCCCCCCCCCCCC[Se]CCOC(=O)CCN(CCC(=O)OCC[Se]CCCCCCCCCCCCCC)CCN1CCCC1]
* * * * *